(12) United States Patent
Kim et al.

(10) Patent No.: US 11,214,594 B2
(45) Date of Patent: Jan. 4, 2022

(54) ANTIMICROBIAL PEPTIDE HAVING SYNERGISTIC ANTIBACTERIAL EFFECT WITH ANTIBIOTICS ON MULTIDRUG RESISTANT BACTERIA, AND USE THEREOF

(71) Applicant: KONKUK UNIVERSITY INDUSTRIAL COOPERATION CORP, Seoul (KR)

(72) Inventors: Yangmee Kim, Seoul (KR); Dasom Jeon, Incheon (KR)

(73) Assignee: KONKUK UNIVERSITY INDUSTRIAL COOPERATION CORP., Seoul (KR)

(*) Notice: Subject to any disclaimer, the term of this patent is extended or adjusted under 35 U.S.C. 154(b) by 121 days.

(21) Appl. No.: 16/311,028

(22) PCT Filed: Jun. 23, 2017

(86) PCT No.: PCT/KR2017/006650
§ 371 (c)(1),
(2) Date: Feb. 22, 2019

(87) PCT Pub. No.: WO2017/222335
PCT Pub. Date: Dec. 28, 2017

(65) Prior Publication Data
US 2020/0040035 A1 Feb. 6, 2020

(30) Foreign Application Priority Data

| Jun. 23, 2016 | (KR) | 10-2016-0078630 |
| Sep. 20, 2016 | (KR) | 10-2016-0120307 |
| May 10, 2017 | (KR) | 10-2017-0058124 |
| May 10, 2017 | (KR) | 10-2017-0058131 |
| May 10, 2017 | (KR) | 10-2017-0058137 |

(51) Int. Cl.
| A61K 38/05 | (2006.01) |
| C07K 7/08 | (2006.01) |
| A23K 20/147 | (2016.01) |
| A23K 20/195 | (2016.01) |
| A23L 33/18 | (2016.01) |
| A61K 38/10 | (2006.01) |
| A61K 45/06 | (2006.01) |

(52) U.S. Cl.
CPC .............. C07K 7/08 (2013.01); A23K 20/147 (2016.05); A23K 20/195 (2016.05); A23L 33/18 (2016.08); A61K 38/10 (2013.01); A61K 45/06 (2013.01); A23V 2002/00 (2013.01)

(58) Field of Classification Search
None
See application file for complete search history.

(56) References Cited

U.S. PATENT DOCUMENTS

2010/0316643 A1 12/2010 Eckert et al.

FOREIGN PATENT DOCUMENTS

| KR | 2003-0024961 | 3/2003 |
| KR | 2010-0100246 | 9/2010 |
| KR | 10-1150281 | 5/2012 |
| KR | 2014-0018689 | 2/2014 |
| KR | 2015-0042447 | 4/2015 |

OTHER PUBLICATIONS

Shin, 2015, Biochemistry, 54, 3921-3931 (Year: 2015).*
https://peptidenexus.com/aminoacid (Author: Nosov), 7 pages, Mar. 16, 2016 (Year: 2016).*
Shin, Biochemistry 2015, 54, 3921-3931 (Year: 2015).*
International Search Report and Written Opinion issued in International Patent Application No. PCT/KR2017/006650, dated Oct. 30, 2017.
Kim et al., "Structure and Function of Papiliocin with Antimicrobial and Anti-Inflammatory Activities Isolated from the Swallowtail Butterfly, Papilio xuthus" Journal of Biological Chemistry, 2011, 286(48):41296-41311.
Lee et al., "Functional Roles of Aromatic Residues and Helices of Papiliocin in its Antimicrobial and Antiinflammatory Activities" Scientific Reports, 2015, 5:12048, 17 Pages.
Oh et al., "Role of the Hinge Region and the Tryptophan Residue in the Synthetic Antimicrobial Peptides, Cecropin A(1-8)-Magainin 2(1-12) and Their Analogues on Their antibiotic Activities and Structures" Biochemistry, 2000, 39:11855-11864.
Shin et al., "Peptoid-Substituted Hybrid Antimicrobial Peptide Derived from Papiliocin and Magainin 2 with Enhanced Bacterial Selectivity and Anti-inflammatory activity" Biochemistry, 2015, 54:3921-3931.

* cited by examiner

Primary Examiner — Satyanarayana R Gudibande
(74) Attorney, Agent, or Firm — Norton Rose Fulbright US LLP

(57) ABSTRACT

The present invention relates to an antimicrobial peptide having an improved antibacterial effect through glutamic acid substitution and, more specifically, to a use of the antimicrobial peptide as an active ingredient in an antibacterial pharmaceutical composition, a food additive, a feed additive, an antiseptic composition, and an antibacterial quasi-drug composition. Not only does the antimicrobial peptide of the present invention exhibit significant antibacterial activity against gram-negative bacteria, but it also exhibits a significant synergistic effect when combinedly treated with antibiotics which have strong antibacterial activity only against gram-positive bacteria and has no or low antibacterial activity against gram-negative bacteria, thereby exhibiting excellent antibacterial effects on gram-positive bacteria, E. coli and Acinetobacter bacteria among gram-negative bacteria, and antibiotic-resistant strains thereof.

13 Claims, 4 Drawing Sheets
Specification includes a Sequence Listing.

ANTIMICROBIAL PEPTIDE HAVING SYNERGISTIC ANTIBACTERIAL EFFECT WITH ANTIBIOTICS ON MULTIDRUG RESISTANT BACTERIA, AND USE THEREOF

CROSS-REFERENCE TO RELATED APPLICATIONS

The present application is a national phase application under 35 U.S.C. § 371 of International Application No. PCT/KR2017/006650, filed Jun. 23, 2017, which claims priority to and the benefit of Korean Patent Application Nos. 10-2016-0078630; 10-2016-0120307; 10-2017-0058124; 10-2017-0058131; and 10-2017-0058137 filed in the Korean Intellectual Property Office on Jun. 23, 2016; Sep. 20, 2016; May 10, 2017; May 10, 2017; and May 10, 2017, respectively, the entire contents of which are incorporated herein by reference.

FIELD OF THE DISCLOSURE

The present invention relates to an antimicrobial peptide having antibacterial activity against gram-negative multidrug resistant bacteria, and provides an antimicrobial peptide having an improved antibacterial effect through substitution of amino acid residues. More specifically, the present invention relates to a use of the antimicrobial peptide as an active ingredient in an antibacterial pharmaceutical composition, a food additive, a feed additive, an antiseptic composition, and an antibacterial quasi-drug composition.

DESCRIPTION OF RELATED ART

Bacterial infection is one of the most common and fatal causes of human diseases. Since penicillin, a number of antibiotics have been developed and have been used for extermination of bacteria invading from the outside in living organisms. However, strains resistant to these antibiotics have recently emerged, and are regarded as a major problem. Bacterial species such as *Enterococcus faecalis, Mycobacterium tuberculosis* and *Pseudomonas aeruginosa*, which can pose life threats, have developed resistance to all the antibiotics known so far (Stuart B. Levy, *Scientific American*, (1988): 46-53).

Tolerance to antibiotics is a phenomenon distinguished from resistance to antibiotics, and the phenomenon was first discovered in *Pneumococcus* sp. in the 1970s and provided an important clue for the mechanism of action of penicillin (Tomasz et al., *Nature,* 227, (1970): 138-140). Conventional chemical antibiotics such as penicillin and cephalosporin exhibit an antibiotic action by synthesis inhibition of cell walls or proteins of microorganisms. However, although the species showing tolerance stop growing in the presence of antibiotics at a typical concentration, they are not killed as a result thereof. Tolerance occurs because when antibiotics inhibit a cell wall synthetase, the activity of autolytic enzymes of bacteria such as autolysin does not occur, and this fact exhibits a result that penicillin kills bacteria by activating endogenous hydrolytic enzymes and the bacteria also survive even during the treatment with antibiotics by suppressing the activity of the bacteria. Accordingly, there is an urgent need for the development of antibiotics with a new mechanism of action that can exterminate these resistant strains, and antimicrobial peptides showing antibiotic mechanisms differently from conventional antibiotics have attracted attention as a new concept of next-generation antibiotics (Zasloff M. *Curr Opin Immunol* 4 (1992): 3-7; Boman, H. G., Cell, 65.205 (1991); Boman, H. G. *J Intern Med.* 254.3 (2003): 197-215; Hancock, R. E., & Scott, M. G., *Proc. Natl. Acad. Sci. U.S.A.* 97 (2000): 8856-8861; Zasloff, M., *Nature* 415 (2002): 389-395).

Recently, *P. aeruginosa* and *A. baumannii*, which are gram-negative bacteria among multi-drug resistant bacteria and belong to bacterial species in which acquired tolerance occurs most frequently due to endogenous reasons, are known as bacterial species in which an antibiotic resistance problem is serious. In *P. aeruginosa* and *A. baumannii*, multi-drug resistance refers to the strains' resistance to all three series of drugs such as aminoglycoside, fluoroquinolone, and carbapenem, and the common feature of these multi-drug resistant strains is that carbapenem has been almost the only effective antibiotic, and that more and more strains resistant even to carbapenem have arisen for about 10 years, leading to major restrictions on antibiotic treatment. *Pseudomonas* or *Pseudomonas aeruginosa* is a gram-negative bacterium and a common infectious pathogen, and it can naturally and easily acquire resistance to antibiotics due to low susceptibility to antibiotics, is a causative bacterium of respiratory infection, burn infection, pneumonia in a patient with cystic fibrosis, and urinary tract infection where an artificial respirator is being used, is present in a focus of infection such as an artificial ventilator, a suction catheter, and stagnant contaminated water, spreads directly or indirectly to the patient and stays, and is known to show a high mortality in patients with a progressive disease due to difficulty of treatment.

*Acinetobacter baumannii* is a gram-negative aerobic coccobacillus and has been an important cause of hospital infection in many hospitals, and particularly recently, infection by multi-drug resistant *Acinetobacter baumannii* (MRAB) showing resistance to aminoglycoside, cephalosporin, fluoroquinolone, beta-lactamase inhibitors, and carbapenem has been increasing. In 2010, the case in which 46 people were infected with *Acinetobacter baumannii* and 10 of the patients died aroused awareness about MRAB, which is strongly resistant to antibiotics and has been rapidly increasing worldwide for the recent 10 years, and is spurring the development of an antibiotic. *Acinetobacter baumannii* itself is commonly present in water or soil or even in the human skin, and a healthy person is not taken ill even when infected with *Acinetobacter baumannii*. However, when people with reduced immunity are infected, they may die of pneumonia or sepsis, and the infection case has begun to increase in the US, Europe, and the like since the 1990s, and from the 2000s, a type of *Acinetobacter baumannii* against which almost all the antibiotics are ineffective appeared. Typically, multi-drug resistant *Acinetobacter baumannii* (MDRAB) refers to a strain that is resistant to all three series of drugs such as aminoglycoside, fluoroquinolone, and carbapenem and is sensitive to only colistin or the like, and *Acinetobacter baumannii* may further exhibit sensitivity to tigecycline. For *Acinetobacter baumannii* which is a major causative bacterium of medical-related infections, carbapenem has been almost the only effective antibiotic, but more and more strains resistant even to carbapenem have arisen for about 10 years, and this has led to major restrictions on the treatment of infective symptoms. Recently, the resistance rate of *P. aeruginosa* is about 20%, whereas the resistance rate of *Acinetobacter baumannii* has been rapidly increased and has surpassed 50% in most university hospitals. An increase in resistance rate to carbapenem has led to an increase in *Acinetobacter baumannii*, and in a survey of health-related infection rates in intensive care units nationwide in 2010, *Acinetobacter baumannii* took the third place among causative bacteria in terms of frequency, following Methicillin-resistant *Staphylococcus aureus* (MRSA) and *Enterococcus* sp. and surpassing *P. aeruginosa*. Accordingly, there is an urgent need for the development of a therapeutic agent because *Acinetobacter baumannii* has a high frequency and a high fatality among causative bacteria of infection in severe patients in Korea.

In a broad sense, an antigen-antibody reaction called an immune response has played a major role in biological defense for vertebrate animals including humans. However, insects and amphibians protect themselves by strengthening the innate immune mechanism, which is different from the acquired immune mechanism such as the antigen-antibody reaction. As described above, innate immunity plays a role as an important defense system against early infection not only in insects and amphibians but also in vertebrate animals including humans. A very important means of the innate immune mechanism is to acquire an antibacterial peptide having bactericidal and inactivating effects on various microorganisms. Peptides or proteins with antimicrobial action, especially antibacterial peptides, are likely to be used as antibiotics for controlling the disease of livestock and humans and infection of various pathogens. Recently, as the antibiotic resistance problem has become serious, interests in a new drug candidate substance using these antimicrobial peptides have been increasing. Since antimicrobial peptides have antibacterial activity targeting bacterial membranes, the peptides are seen to have characteristics of maintaining activity even against strains resistant to existing antibiotics. Therefore, various naturally occurring antimicrobial peptides are attracting attention as biological resources important for exploring novel antibiotics capable of replacing existing antibiotics threatened by the appearance of resistant strains.

Insect antibacterial proteins and peptides discovered so far include about 200 types isolated from insects since the first report of cecropin in cecropia moths by the Dr. Boman's research team, and these proteins and peptides can be largely classified into cecropins, defensins, and peptides abundant of proline and glycine amino acids, according to the structure and size.

Cecropins are basic proteins consisting of 31 to 39 amino acids, and a new antibacterial peptide (papiliocin) from larvae of the tiger swallowtail butterfly that has been recently patented by the present research team has an α-helix-hinge-α-helix structure including an amphipathic helical structure at the N-terminus and a hydrophobic helix at the C-terminus, and has excellent antibacterial activity and excellent anti-inflammatory activity against various pathogens (Kim et al., J Biol Chem. 2011, 286.48: 41296-41311). In particular, it has been known that the region having the helix structure at the N-terminus plays an important role in antibacterial activity, and it has been disclosed that the antibacterial peptide has been confirmed to have excellent antibacterial ability and excellent anti-inflammatory activity against resistant strains (Kim et al., J Biol Chem. 2011, 286.48: 41296-41311 and Lee et al., Scientific Reports, 2015, 5:12048). Magainin (Magainin 2, MA) is an amphiphilic peptide derived from amphibians and has antibacterial activity against various bacteria, and the present research team discovered the three-dimensional structure of a CA-MA peptide produced by binding a peptide at the N-terminus of cecropin to a peptide at the N-terminus of magainin, and confirmed that the structure has excellent antibacterial and anticancer activity (Oh et al., Biochemistry. 2000 Oct. 3; 39(39):11855-64).

In addition, a PapMA-1 hybrid peptide produced by linking 8 residues in the N-terminal region of papiliocin to 9 residues at the N-terminus of magainin was designed and synthesized, and it was reported that the PapMA-1 has excellent antibacterial activity against gram-negative bacteria and gram-positive bacteria (Shin et al. Biochemistry. 2015 Jun. 30; 54(25):3921-31).

SUMMARY OF THE INVENTION

As a result of continuously conducting a study related to a peptide synthesized by linking papiliocin to magainin, the present inventors designed peptides PapMA-2 to PapMA-24 by substituting amino acid residues in the parent antimicrobial peptide (PapMA-1) such that the antibacterial activity is enhanced. Together with this, the present inventors confirmed that the antimicrobial peptide designed in the present invention exhibits significant antibacterial activity against gram-negative bacteria and exhibits a significant synergistic effect during combined treatment with a conventional antibiotic, and thus exhibits excellent antibacterial effects on gram-negative bacteria as well as gram-positive bacteria, particularly *E. coli, Acinetobacter* bacteria and antibiotic-resistant strains thereof, thereby completing the present invention.

Thus, the present inventors prepared antimicrobial peptides PapMA-2, PapMA-3, and PapMA-4 using, as a template, a PapMA-1 antimicrobial peptide in which the residues in the N-terminal region of antimicrobial peptide papiliocin are conjugated with the residues in the N-terminal region of magainin and substituting alanine (A) which is the 15th amino acid with tryptophan (W); and substituting phenylalanine (F) which is the 18th amino acid with tryptophan in the sequence of PapMA-1 such that PapMA-2, PapMA-3, and PapMA-4 have higher antibacterial activity against gram-negative bacteria than PapMA-1.

In addition, the present inventors designed antimicrobial peptides PapMA-5 to PapMA-10 based on the peptides PapMa-1 to PapMA-4, by substituting the 11th amino acid with lysine; and substituting the 15th amino acid with phenylalanine or lysine.

In addition, the present inventors designed antimicrobial peptides PapMA-11 to PapMA-14 based on the peptides PapMA-1 to PapMA-10, by substituting serine (S) which is the 14th amino acid with glutamic acid (E).

In addition, the present inventors designed antimicrobial peptides PapMA-15 to PapMA-20 based on the peptides PapMA-2 to PapMA-14, by substituting proline (P) which is the 9th amino acid with D-lysine (k); and/or substituting glutamic acid (E) which is the 14th amino acid with L-lysine (K).

Furthermore, the present inventors designed antimicrobial peptides PapMA-21 to PapMA-24 based on the peptides PapMA-1 to PapMA-20, by substituting proline (P) or D-lysine (k) which is the 9th amino acid with D-leucine (l).

The present inventors confirmed that the antimicrobial peptide could exhibit excellent antibacterial effects on *E. coli, Acinetobacter* bacteria, and antibiotic-resistant strains thereof, which are gram-negative bacteria, and could exhibit a significant synergistic antibacterial activity when administered with an antibiotic, thereby completing the present invention.

Accordingly, an object of the present invention is to provide a novel antimicrobial peptide which exhibits antibacterial activity against gram-positive bacteria, gram-negative bacteria, or multi-drug resistant strains thereof.

In addition, another object of the present invention is to provide an antibacterial composition containing the antimicrobial peptide as an active ingredient.

Furthermore, still another object of the present invention is to provide an antibacterial composition exhibiting an excellent synergistic antibacterial activity against gram-negative multi-drug resistant bacteria by administering the antimicrobial peptide in combination with an antibiotic.

To achieve the objects, the present invention provides an antimicrobial peptide consisting of amino acid sequences obtained by subjecting a peptide consisting of an amino acid sequence represented by SEQ ID No. 1 to one or more substitutions selected from the group consisting of the following (i) to (v):

(i) substitution of proline (P) which is the 9th amino acid with D-lysine (k) or D-leucine (l);

(ii) substitution of phenylalanine (F) which is the 11th amino acid with leucine (L);

(iii) substitution of serine (S) which is the 14th amino acid with glutamic acid (E) or L-lysine (K);

(iv) substitution of alanine (A) which is the 15th amino acid with tryptophan (W), phenylalanine (F), or leucine (L); and (v) substitution of phenylalanine (F) which is the 18th amino acid with tryptophan (W).

Further, the present invention provides a novel synthetic peptide consisting of any one amino acid sequence selected from the group consisting of SEQ ID Nos. 2 to 24.

In a preferred embodiment of the present invention, the antimicrobial peptide may consist of an amino acid sequence in which either one or both of the 15th amino acid, alanine (A), and the 18th amino acid, phenylalanine (F), of a peptide consisting of an amino acid sequence represented by SEQ ID No. 1 have been substituted with tryptophan (W), in which case the antimicrobial peptide may consist of any one of amino acid sequences represented by SEQ ID Nos. 2 to 4.

In a preferred embodiment of the present invention, the antimicrobial peptide may consist of an amino acid sequence obtained by subjecting any one amino acid sequence selected from the group consisting of SEQ ID Nos. 1 to 4 to at least one substitution selected from the group consisting of substitution of phenylalanine (F) which is the 11th amino acid with leucine (L); and substitution of alanine (A) or tryptophan (W) which is the 15th amino acid with phenylalanine (F) or leucine (L), in which case the amino acid sequence may consist of any one of amino acid sequences represented by SEQ ID Nos. 5 to 10.

In a preferred embodiment of the present invention, the antimicrobial peptide may consist of an amino acid sequence obtained by subjecting any one amino acid sequence selected from the group consisting of SEQ ID Nos. 1 to 10 to the substitution of serine (S) which is the 14th amino acid with glutamic acid (E), in which case the amino acid sequence may consist of any one amino acid sequence selected from the group consisting of SEQ ID Nos. 11 to 14.

In a preferred embodiment of the present invention, the antimicrobial peptide may consist of an amino acid sequence obtained by subjecting any one amino acid sequence selected from the group consisting of SEQ ID Nos. 2 to 14 to at least one substitution selected from the group consisting of substitution of proline (P) which is the 9th amino acid with D-lysine (k); and substitution of glutamic acid (E) which is the 14th amino acid with L-lysine (K), in which case the amino acid sequence may consist of any one of amino acid sequences represented by SEQ ID Nos. 15 to 20.

In a preferred embodiment of the present invention, the antimicrobial peptide may consist of an amino acid sequence in which the 9th amino acid, proline (P) or D-lysine (k), of any one amino acid sequence selected from the group consisting of SEQ ID Nos. 1 to 20 has been substituted with D-leucine (l), in which case the amino acid sequence may consist of any one amino acid sequence selected from the group consisting of SEQ ID Nos. 21 to 24.

In addition, the present invention provides an antibacterial pharmaceutical composition containing, as an active ingredient, an antimicrobial peptide consisting of amino acid sequences obtained by subjecting a peptide consisting of an amino acid sequence represented by SEQ ID No. 1 to one or more substitutions selected from the group consisting of the following (i) to (v):

(i) substitution of proline (P) which is the 9th amino acid with D-lysine (k) or D-leucine (l);

(ii) substitution of phenylalanine (F) which is the 11th amino acid with leucine (L);

(iii) substitution of serine (S) which is the 14th amino acid with glutamic acid (E) or L-lysine (K);

(iv) substitution of alanine (A) which is the 15th amino acid with tryptophan (W), phenylalanine (F), or leucine (L); and (v) substitution of phenylalanine (F) which is the 18th amino acid with tryptophan (W).

Further, the present invention provides a food additive containing the antimicrobial peptide as an active ingredient.

In addition, the present invention provides a feed additive containing the antimicrobial peptide as an active ingredient.

Further, the present invention provides an antiseptic composition containing the antimicrobial peptide as an active ingredient.

In addition, the present invention provides an antibacterial quasi-drug composition containing the antimicrobial peptide as an active ingredient.

Furthermore, the present invention provides an antibacterial pharmaceutical composition containing, as active ingredients, an antimicrobial peptide consisting of amino acid sequences obtained by subjecting a peptide consisting of an amino acid sequence represented by SEQ ID No. 1 to one or more substitutions selected from the group consisting of the following (i) to (v); and an antibiotic:

(i) substitution of proline (P) which is the 9th amino acid with D-lysine (k) or D-leucine (l);

(ii) substitution of phenylalanine (F) which is the 11th amino acid with leucine (L);

(iii) substitution of serine (S) which is the 14th amino acid with glutamic acid (E) or L-lysine (K);

(iv) substitution of alanine (A) which is the 15th amino acid with tryptophan (W), phenylalanine (F), or leucine (L); and (v) substitution of phenylalanine (F) which is the 18th amino acid with tryptophan (W).

Further, the present invention provides a food additive containing, as active ingredients, the antimicrobial peptide; and an antibiotic.

In addition, the present invention provides a feed additive containing, as active ingredients, the antimicrobial peptide; and an antibiotic.

Further, the present invention provides an antiseptic composition containing, as active ingredients, the antimicrobial peptide; and an antibiotic.

In addition, the present invention provides an antibacterial quasi-drug composition containing, as active ingredients, the antimicrobial peptide; and an antibiotic.

In a preferred embodiment of the present invention, the antimicrobial peptide may consist of any one of amino acid sequences represented by SEQ ID Nos. 1 to 24.

In another preferred embodiment of the present invention, the antibiotics may be one or more selected from the group consisting of erythromycin, ampicillin, vancomycin, linezolid, methicillin, oxacillin, cefotaxime, rifampicin, amikacin, gentamicin, amikacin, kanamycin, Tobramycin, Neomycin, Ertapenem, Doripenem, imipenem/cilastatin, meropenem, ceftazidime, cefepime, ceftaroline, ceftobiprole, aztreonam, piperacillin, polymyxin B, colistin, ciprofloxacin, levofloxacin, moxifloxacin, gatifloxacin, tigecycline, a conjugate thereof, and derivatives thereof.

In still another preferred embodiment of the present invention, the antibacterial pharmaceutical composition may be an antibacterial pharmaceutical composition having antibacterial activity against gram-positive bacteria, gram-negative bacteria, and antibiotic-resistant strains thereof.

In yet another preferred embodiment of the present invention, the gram-positive bacteria may be one or more selected from the group consisting of *Bacillus subtilis, Staphylococcus aureus* and *Staphylococcus epidermidis*.

In still yet another preferred embodiment of the present invention, the gram-negative bacteria may be one or more selected from the group consisting of *Escherichia coli, Pseudomonas aeruginosa, Acinetobacter baumannii* and *Salmonella typhimurium*.

Therefore, the present invention provides an antimicrobial peptide PapMA-1 which is a papiliocin hybrid peptide derivative prepared by linking residues in an N-terminal region of antibacterial peptide papiliocin (Pap) isolated from larvae of the tiger swallowtail butterfly to N-terminal region residues of magainin (magainin 2, MA), and also provides antimicrobial peptides PapMA-2 to PapMA-24 obtained by substituting amino acid residues of the peptide of PapMA-1 such that antibacterial activity can be enhanced.

The antimicrobial peptide of the present invention may have enhanced antibacterial effect as compared to that of a parent peptide, through substitution of amino acid residues. Accordingly, not only does the antimicrobial peptide of the present invention exhibit significant antibacterial activity against gram-negative bacteria, but it also exhibits a significant synergistic effect when combinedly treated with has antibiotics which have strong antibacterial activity only against gram-positive bacteria and has no or low antibacterial activity against gram-negative bacteria, thereby exhibiting excellent antibacterial effects on gram-positive bacteria, gram-negative bacteria, and antibiotic-resistant strains thereof. Therefore, an antibacterial composition containing the antimicrobial peptide of the present invention and an antibacterial composition containing a combination of the antimicrobial peptide of the present invention and antibiotics can be provided as an antibacterial pharmaceutical composition, a food additive, a feed additive, an antiseptic composition, and a quasi-drug composition, and they can exhibit enhanced antibacterial activity despite containing a small concentration of chemical antibiotics.

DETAILED DESCRIPTION OF THE INVENTION

Figure 1:
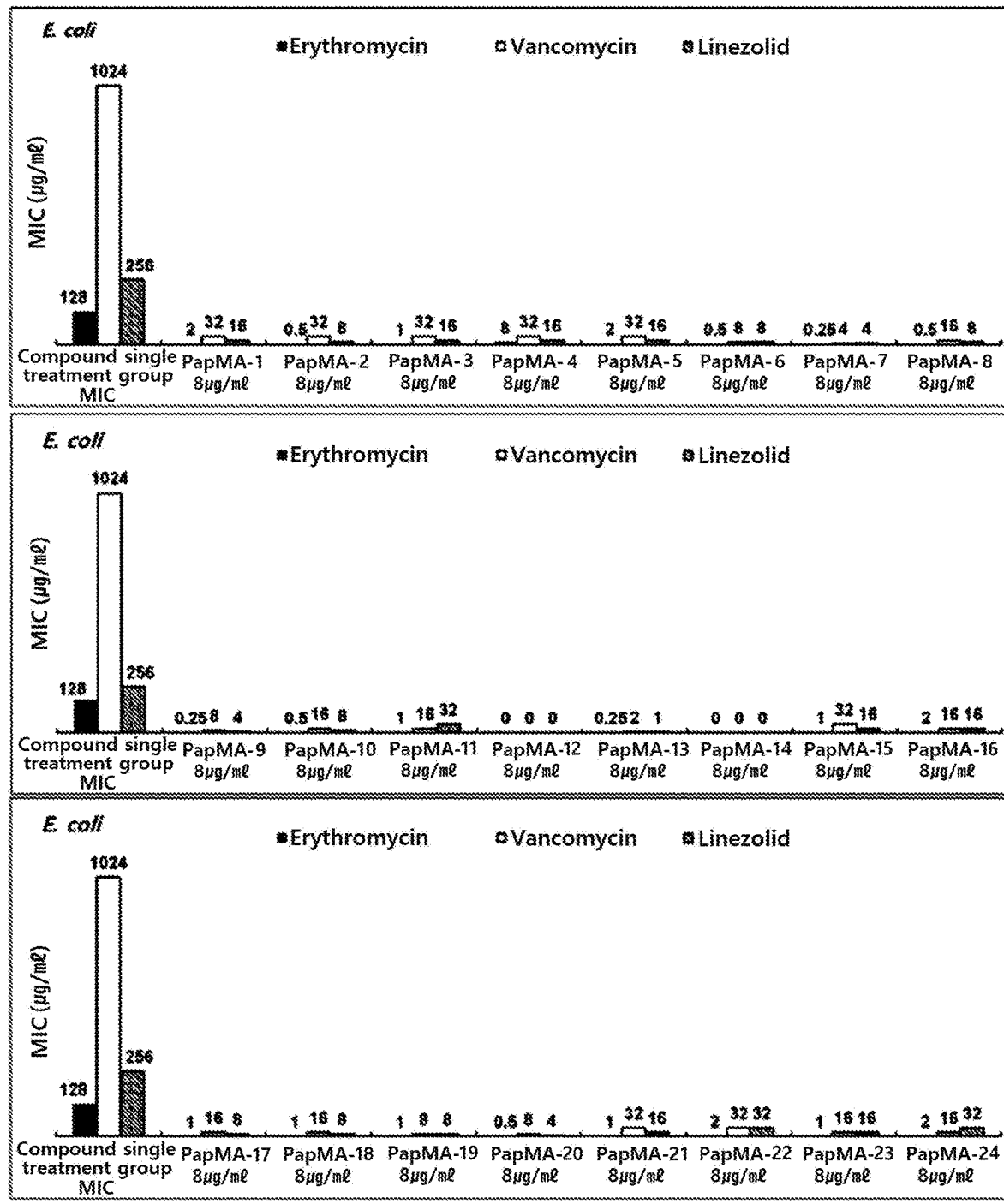
FIG. 1 is a view confirming a synergistic antibacterial activity of PapMA-1 to PapMA-24 (8 μg/ml) and commercially available antibiotics against *E. coli*.

Hereinafter, the present invention will be described in detail.

It is continuously required to develop an antibiotic material exhibiting antibacterial activity against multi-drug resistant bacteria having resistance against antibiotics, and the designing of relevant antibacterial peptides have been reported, but there is a need for further studies on an antimicrobial peptide capable of exhibiting a synergistic effect during combined treatment with a conventional antibiotic.

Since not only does the antimicrobial peptide of the present invention exhibit significant antibacterial activity against gram-negative bacteria, but it also exhibits antibacterial activity with excellent antibacterial effects on gram-negative bacteria such as *E. coli* and *Acinetobacter* bacteria, and antibiotic-resistant strains thereof during combined treatment with antibiotics exhibiting effective antibacterial activity only against gram-positive bacteria, the antimicrobial peptide of the present invention can exhibit excellent antibacterial effects on *E. coli* and *Acinetobacter* bacteria and multi-drug resistant strains thereof, and thus is effective even with a small amount of antibiotics being administered.

Therefore, the present invention provides a novel synthetic peptide consisting of amino acid sequences obtained by subjecting a peptide consisting of an amino acid sequence represented by SEQ ID No. 1 to one or more substitutions selected from the group consisting of the following (i) to (v):

(i) substitution of proline (P) which is the 9th amino acid with D-lysine (k) or D-leucine (l);

(ii) substitution of phenylalanine (F) which is the 11th amino acid with leucine (L);

(iii) substitution of serine (S) which is the 14th amino acid with glutamic acid (E) or L-lysine (K);

(iv) substitution of alanine (A) which is the 15th amino acid with tryptophan (W), phenylalanine (F), or leucine (L); and (v) substitution of phenylalanine (F) which is the 18th amino acid with tryptophan (W).

Further, the present invention provides an antimicrobial peptide consisting of amino acid sequences obtained by subjecting a peptide consisting of an amino acid sequence represented by SEQ ID No. 1 to one or more substitutions selected from the group consisting of the following (i) to (v):

(i) substitution of proline (P) which is the 9th amino acid with D-lysine (k) or D-leucine (l);

(ii) substitution of phenylalanine (F) which is the 11th amino acid with leucine (L);

(iii) substitution of serine (S) which is the 14th amino acid with glutamic acid (E) or L-lysine (K);

(iv) substitution of alanine (A) which is the 15th amino acid with tryptophan (W), phenylalanine (F), or leucine (L); and (v) substitution of phenylalanine (F) which is the 18th amino acid with tryptophan (W).

In addition, the present invention provides a novel synthetic peptide consisting of any one amino acid sequence selected from the group consisting of SEQ ID Nos. 2 to 24.

The "peptide consisting of an amino acid sequence represented by SEQ ID No. 1" of the present invention is PapMA-1, which is a synthetic peptide consisting of 18 residues prepared by linking a peptide with 9 residues in the 4th to 12th positions of the N-terminal of magainin (magainin 2, MA) to 8 residues in the 1st to 8th positions of the N-terminal region of papiliocin (Pap) through proline (Shin et al. Biochemistry. 2015 Jun. 30; 54(25):3921-31). From the "peptide consisting of the amino acid sequence represented by SEQ ID No. 1", alanine (A) which is the 15th amino acid can be substituted with tryptophan (W); and/or phenylalanine (F) which is the 18th amino acid can be substituted with tryptophan (W), and it is preferred that the peptide of the present invention is an antimicrobial peptide of an amino acid sequence represented by any one of SEQ ID Nos. 2 to 4.

In the sequence of the "antimicrobial peptide", by "substituting alanine (A) and/or phenylalanine (F) with tryptophan (W)", the sequence can be optimized so as to exhibit increased antibacterial activity or, when combinedly treated with a conventional antibiotic, to exhibit an enhanced synergistic effect compared to a peptide consisting of an amino acid sequence of SEQ ID No. 1.

More specifically, among the antimicrobial peptides, an antimicrobial peptide consisting of an amino acid sequence represented by SEQ ID No. 2 is PapMA-2, and it is a sequence obtained by substituting the 18th amino acid, phenylalanine, of the amino acid represented by SEQ ID No. 1 with tryptophan.

An antimicrobial peptide consisting of an amino acid sequence represented by SEQ ID No. 3 is PapMA-3, and it is a sequence obtained by substituting the 15th amino acid, alanine, of the amino acid sequence represented by SEQ ID No. 1 with tryptophan.

An antimicrobial peptide consisting of an amino acid sequence represented by SEQ ID No. 4 is PapMA-4, and it is a sequence obtained by substituting the 15th amino acid, alanine, and the 18th amino acid, phenylalanine, of the amino acid sequence represented by SEQ ID No. 1 with tryptophan.

Further, the antimicrobial peptide of the present invention may be obtained by subjecting the peptide consisting of the "amino acid sequences represented by SEQ ID Nos. 1 to 4" to substitution of the 11th amino acid, phenylalanine (F), with leucine (L); and/or substitution of the 15th amino acid, alanine (A) or tryptophan (W), with phenylalanine (F) or leucine (L), and it is preferred that the antimicrobial peptide of the present invention is an antimicrobial peptide of an amino acid sequence represented by any one of SEQ ID Nos. 5 to 10.

In the sequence of the "peptide" of the present invention, through a step of "substitution with phenylalanine or leucine", the sequence can be optimized so as to exhibit increased antibacterial activity or, when combinedly treated with a conventional antibiotic, to exhibit an enhanced synergistic effect compared to a peptide consisting of amino acid sequences of SEQ ID Nos. 1 to 4. When the hydrophobicity, amount of alpha-helical structure, and cationicity of an antibacterial peptide having an amphoteric structure are increased, it is known that the antibacterial activity is increased due to high interaction with a biomembrane, and the antibacterial activity of the peptide may be increased by optimizing these conditions (Lee et al., Scientific Reports, 2015, 5:12048). The present invention has been made in an effort to increase antibacterial activity and a synergistic effect with conventional antibiotics by substituting with hydrophobic residues. Phenylalanine is an amino acid having the highest hydrophobicity among aromatic amino acids, and leucine and isoleucine are amino acids having the highest hydrophobicity among aliphatic amino acids. Since isoleucine has an economic problem due to a very high price of D-amino acid, leucine has been frequently used in the optimization of peptides. Therefore, in the present invention, antibacterial activity can be increased by substituting the position of alanine, which is the 15th residue and having low hydrophobicity among aliphatic hydrophobic amino acids. Further, antibacterial activity and a synergistic effect with conventional antibiotics can be increased by substituting phenylalanine, which is an aromatic hydrophobic amino acid and the 11th amino acid of the peptide, with leucine, which is an aliphatic amino acid having high hydrophobicity.

More specifically, among the novel antimicrobial peptides of the present invention, an antimicrobial peptide consisting of an amino acid sequence represented by SEQ ID No. 5 is PapMA-5, and it is a sequence in which alanine which is the 15th residue in the amino acid sequence of SEQ ID No. 1 has been substituted with phenylalanine (F).

An antimicrobial peptide consisting of an amino acid sequence represented by SEQ ID No. 6 is PapMA-6, and it is a sequence in which alanine (A) which is the 15th residue in the amino acid sequence of SEQ ID No. 1 has been substituted with leucine (L).

An antimicrobial peptide consisting of an amino acid sequence represented by SEQ ID No. 7 is PapMA-7, and it is a sequence in which in the amino acid sequence of SEQ ID No. 1, phenylalanine (F) which is the 11th residue is substituted with leucine (L); and alanine (A) which is the 15th residue is substituted with phenylalanine (F).

An antimicrobial peptide consisting of an amino acid sequence represented by SEQ ID No. 8 is PapMA-8, and it is a sequence in which in the amino acid sequence of SEQ ID No. 1, phenylalanine (F) which is the 11th residue is substituted with leucine (L); and alanine (A) which is the 15th residue is substituted with leucine (L).

An antimicrobial peptide consisting of an amino acid sequence represented by SEQ ID No. 9 is PapMA-9, and is a sequence in which phenylalanine (F) which is the 11th residue in the amino acid sequence of SEQ ID No. 2 is substituted with leucine (L).

An antimicrobial peptide consisting of an amino acid sequence represented by SEQ ID No. 10 is PapMA-10, and is a sequence in which in the amino acid sequence of SEQ ID No. 2, phenylalanine (F) which is the 11th residue is substituted with leucine (L); and alanine (A) which is the 15th residue is substituted with leucine (L).

From the peptide consisting of the amino acid sequences represented by SEQ ID Nos. 1 to 10, serine (S) which is the 14th amino acid can be substituted with glutamic acid (E); and preferably, it is preferred that the antimicrobial peptide of the present invention is an antimicrobial peptide of an amino acid sequence represented by any one of SEQ ID Nos. 11 to 14.

In the sequence of the antimicrobial peptide, by substituting serine (S) with glutamic acid (E), the antimicrobial peptide of the present invention can exhibit increased antibacterial activity compared to a peptide consisting of any one amino acid sequence of SEQ ID Nos. 1 to 10, or the sequence can be optimized so as to have a higher synergistic effect during the combined treatment with a conventional antibiotic.

In the present invention, it is characterized in that the overall electric charge of the peptide is lowered by substituting serine, a polar amino acid and the 14th residue, with glutamic acid which is a negatively-charged (acidic) amino acid. Specifically, it is preferred that the total electric charge of PapMA-1 which is a parent peptide is +8, whereas the total electric charge of the antimicrobial peptide (PapMA-11 to PapMA-14) is +7.

Specifically, the antimicrobial peptide of the present invention preferably consists of any one amino acid sequence selected from the group consisting of SEQ ID Nos. 11 to 14, but is not limited thereto.

More specifically, among the antimicrobial peptides, an antimicrobial peptide consisting of an amino acid sequence represented by SEQ ID No. 11 is PapMA-11, and it is a sequence in which serine which is the 14th amino acid is substituted with glutamic acid from the amino acid sequence represented by SEQ ID No. 1.

An antimicrobial peptide consisting of an amino acid sequence represented by SEQ ID No. 12 is PapMA-12, and it is a sequence in which serine which is the 14th amino acid is substituted with glutamic acid from the amino acid sequence represented by SEQ ID No. 7.

An antimicrobial peptide consisting of an amino acid sequence represented by SEQ ID No. 13 is PapMA-13, and it is a sequence in which serine which is the 14th amino acid is substituted with glutamic acid from the amino acid sequence represented by SEQ ID No. 9.

An antimicrobial peptide consisting of an amino acid sequence represented by SEQ ID No. 14 is PapMA-14, and is a sequence in which serine which is the 14th amino acid is substituted with glutamic acid from the amino acid sequence represented by SEQ ID No. 2. From the peptide consisting of the amino acid sequences represented by SEQ ID Nos. 1 to 14, proline (P) which is the 9th amino acid can be substituted with D-lysine (k); and/or glutamic acid (E) which is the 14th amino acid can be substituted with L-lysine (K), and preferably, it is preferred that the peptide of the present invention is an antimicrobial peptide of an amino acid sequence represented by any one of SEQ ID Nos. 15 to 20.

In the sequence of the antimicrobial peptide, by substituting proline (P) and/or glutamic acid (E) with D-lysine (k) and/or L-lysine (K), the antimicrobial peptide of the present invention can exhibit increase antibacterial activity compared to a peptide consisting of any one amino acid sequence of SEQ ID Nos. 1 to 14, or the sequence can be optimized so as to have a higher synergistic effect during the combined treatment with a conventional antibiotic.

In the present invention, it is characterized in that electric charge of a bent portion was increased by substituting proline, a polar residue and the 9th amino acid, with L-lysine (k); and/or substituting glutamic acid, a negatively-charged (acidic) residue and the 14th amino acid, with D-lysine (k), a positively-charged (basic) residue. It is preferred that these characteristics occur from the fact that the cationicity is further increased as the 9th amino acid, proline, which induces the bent structure is substituted with D-lysine. Specifically, it is preferred that the total electric charge of PapMA-1 which is a parent peptide is +8, whereas the total electric charge of the antimicrobial peptide (PapMA-15 to PapMA-20) is +8 to +10.

Specifically, the antimicrobial peptide of the present invention preferably consists of any one amino acid sequence selected from the group consisting of SEQ ID Nos. 15 to 20, but is not limited thereto.

More specifically, among the antimicrobial peptides, an antimicrobial peptide consisting of an amino acid sequence represented by SEQ ID No. 15 is PapMA-15, and it is a sequence in which proline which is the 9th amino acid is substituted with D-lysine (k) from the amino acid sequence represented by SEQ ID No. 7.

An antimicrobial peptide consisting of an amino acid sequence represented by SEQ ID No. 16 is PapMA-16, and it is a sequence in which proline which is the 9th amino acid is substituted with D-lysine (k) from the amino acid sequence represented by SEQ ID No. 9.

An antimicrobial peptide consisting of an amino acid sequence represented by SEQ ID No. 17 is PapMA-17, and it is a sequence in which proline which is the 9th amino acid and glutamic acid which is the 14th amino acid are substituted with D-lysine (k) and L-lysine (K), respectively from the amino acid sequence represented by SEQ ID No. 12.

An antimicrobial peptide consisting of an amino acid sequence represented by SEQ ID No. 18 is PapMA-18, and it is a sequence in which proline which is the 9th amino acid and glutamic acid which is the 14th amino acid are substituted with D-lysine (k) and L-lysine (K), respectively from the amino acid sequence represented by SEQ ID No. 13.

An antimicrobial peptide consisting of an amino acid sequence represented by SEQ ID No. 19 is PapMA-19, and it is a sequence in which proline which is the 9th amino acid is substituted with D-lysine (k) from the amino acid sequence represented by SEQ ID No. 12.

An antimicrobial peptide consisting of an amino acid sequence represented by SEQ ID No. 20 is PapMA-20, and it is a sequence in which proline which is the 9th amino acid is substituted with D-lysine (k) from the amino acid sequence represented by SEQ ID No. 13.

From the peptide consisting of the amino acid sequences represented by SEQ ID Nos. 1 to 20, proline (P) or D-lysine (k) which is the 9th amino acid can be substituted with D-leucine (l); and preferably, it is preferred that the antimicrobial peptide of the present invention is an antimicrobial peptide of an amino acid sequence represented by any one of SEQ ID Nos. 21 to 24.

In the sequence of the antimicrobial peptide, by substituting proline (P) or D-lysine (k) with D-leucine (l), the antimicrobial peptide of the present invention can exhibit increased antibacterial activity compared to a peptide consisting of any one amino acid sequence of SEQ ID Nos. 1 to 20, or the sequence can be optimized so as to have a higher synergistic effect during the combined treatment with a conventional antibiotic.

In the present invention, it is characterized in that electric charge of a bent portion was increased by substituting proline, a polar residue and the 9th amino acid, or D-lysine (k), a positively-charged (basic) residue, with D-leucine (l), a non-polar residue. It is preferred that these characteristics occur from the fact that a bent structure is induced in the peptide by substituting proline, which is the 9th residue, is substituted with D-leucine so as to further increase hydrophobicity. The peptide can exhibit a bent structure or linear structure, depending on the 9th amino acid residue in the peptide sequence of the present invention.

From the viewpoint that the co-administration of the antimicrobial peptide of the present invention and conventional antibiotics could provide a synergistic effect, it is preferred that the structure of the antimicrobial peptide is not a linear structure, but a bent structure. For this purpose, it is preferred to design a peptide capable of further enhancing a synergistic effect by substituting the position of the 9th residue, proline, with D-leucine. It is preferred that the total electric charge of PapMA-17 and PapMA-18 which is a parent peptide is +10, whereas the total electric charge of PapMA-21 and PapMA-22 is reduced to +9, whereas the total electric charge of PapMA-19 and PapMA-20 is +8, whereas the total electric charge of PapMA-23 and PapMA-24 is reduced to +7.

Specifically, the antimicrobial peptide of the present invention preferably consists of any one amino acid sequence selected from the group consisting of SEQ ID Nos. 21 to 24, but is not limited thereto.

More specifically, among the antimicrobial peptides, an antimicrobial peptide consisting of an amino acid sequence represented by SEQ ID No. 21 is PapMA-21, and it is a sequence in which D-lysine which is the 9th amino acid is substituted with D-leucine from the amino acid sequence represented by SEQ ID No. 17.

An antimicrobial peptide consisting of an amino acid sequence represented by SEQ ID No. 22 is PapMA-22, and it is a sequence in which D-lysine which is the 9th amino acid is substituted with D-leucine from the amino acid sequence represented by SEQ ID No. 18.

An antimicrobial peptide consisting of an amino acid sequence represented by SEQ ID No. 23 is PapMA-23, and it is a sequence in which D-lysine which is the 9th amino acid is substituted with D-leucine from the amino acid sequence represented by SEQ ID No. 19.

An antimicrobial peptide consisting of an amino acid sequence represented by SEQ ID No. 24 is PapMA-24, and it is a sequence in which D-lysine which is the 9th amino acid is substituted with D-leucine from the amino acid sequence represented by SEQ ID No. 20.

However, the antimicrobial peptide of the present invention is not limited to the amino acid sequences of SEQ ID Nos. 1 to 24, and may include functional equivalents of the amino acid sequences of SEQ ID Nos. 1 to 24.

The functional equivalent refers to a peptide which has a sequence homology of at least 70% or more, preferably 80% or more, more preferably 90% or more, and even more preferably 95% or more with the amino acid sequence of the novel antimicrobial peptide due to the addition, substitution or deletion of an amino acid the novel peptide, and exhibits physiological activity substantially equivalent to that of the novel antimicrobial peptide.

The novel antimicrobial peptide of the present invention is a synthetic peptide, and as a method for the synthesis, it is preferred that the novel antimicrobial peptide is synthesized by a typical chemical peptide synthesis method in the art (W. H. Freeman and Co., Proteins; structures and molecular principles (1983)), and specifically, it is more preferred that the novel antimicrobial peptide is synthesized by a solution-phase peptide synthesis method, a solid-phase peptide synthesis method, a fragment condensation method, and an F-moc or T-BOC chemical method, and more specifically, it is most preferred that the novel antimicrobial peptide is synthesized by a solution-phase peptide synthesis method (Merrifield, R B., *J. Am. Chem. Soc.*, 85.2149: 196), but the synthesis method is not limited thereto. The novel antimicrobial peptide of the present invention preferably has antibacterial activity against gram-positive bacteria, gram-negative bacteria, and antibiotic-resistant strains thereof, but is not limited thereto. Specifically, it is preferred that the gram-positive bacteria are all the gram-positive bacteria known in the art as being gram-positive bacteria, including *Staphylococcus* sp., *Listeria* sp., *Streptococcus* sp., *Corynebacterium* sp., *Lactobacillus* sp., *Clostridium* sp., *Enterococcus* sp., *Erysipelothrix* sp., and *Bacillus* sp., and it is more preferred that the gram-positive bacteria are *Bacillus subtilis*, *Staphylococcus aureus* or *Staphylococcus epidermidis*, but the gram-positive bacteria are not limited thereto. It is preferred that the gram-negative bacteria are all the gram-negative bacteria known in the art as being gram-negative bacteria, including *Escherichia* sp., *Pseudomonas* sp., *Salmonella* sp., *Leptospira* sp., and *Rickettsia* sp., it is more preferred that the gram-negative bacteria are *Escherichia coli*, *Pseudomonas aeruginosa*, *Acinetobacter baumannii* or *Salmonella typhimurium*, and specifically, it is most preferred that the gram-negative bacteria are any one of *Escherichia coli* or *Acinetobacter baumannii*, but the gram-negative bacteria are not limited thereto.

In specific examples of the present invention, the present inventors prepared derivative peptides represented by SEQ ID Nos. 2 to 4, by substituting alanine which is the 15th amino acid and/or phenylalanine which is 18th amino acid with tryptophan in PapMA-1 which is a papiliocin hybrid peptide prepared by linking residues of the N-terminal region of magainin (magainin 2, MA) to the N-terminal region of an antibacterial peptide papiliocin (Pap) isolated from larvae of the tiger swallowtail butterfly, and named the derivative peptides PapMA-2, PapMA-3, and PapMA-4 (Table 1).

Further, the present inventors designed antimicrobial peptides PapMA-5 to PapMA-10 by substituting phenylalanine (F) which is the 11th amino acid with leucine (L); and/or substituting alanine (A) or tryptophan (W) which is the 15th amino acid with phenylalanine (F) or leucine (L) from the peptides PapMA-1 to PapMA-4 (Table 1).

In addition, the present inventors designed antimicrobial peptides PapMA-11 to PapMA-14 by substituting serine (S) which is the 14th amino acid with glutamic acid (E) from the peptides PapMA-1 to PapMA-10 (Table 1).

Further, the present inventors designed antimicrobial peptides PapMA-15 to PapMA-20 by substituting proline (P) which is the 9th amino acid with D-lysine (k); and/or substituting glutamic acid (E) which is the 14th amino acid with L-lysine (K) from the peptides PapMA-2 to PapMA-14 (Table 1).

In addition, the present inventors designed antimicrobial peptides PapMA-21 to PapMA-24 by substituting proline (P) or D-lysine (k) which is the 9th amino acid with D-leucine (l) from the peptides PapMA-1 to PapMA-20 (Table 1).

Further, as a result of identifying antibacterial activity which PapMA-1 to PapMA-24 exhibit, the present inventors confirmed that all of PapMA-1 to PapMA-24 exhibit high antibacterial activity against gram-negative bacteria (Tables 3 to 7). In addition, the present inventors confirmed that erythromycin, vancomycin, and linezolid have antibacterial activity against gram-positive bacteria, and have very low antibacterial activity against gram-negative bacteria (Table 8).

Figure 2:
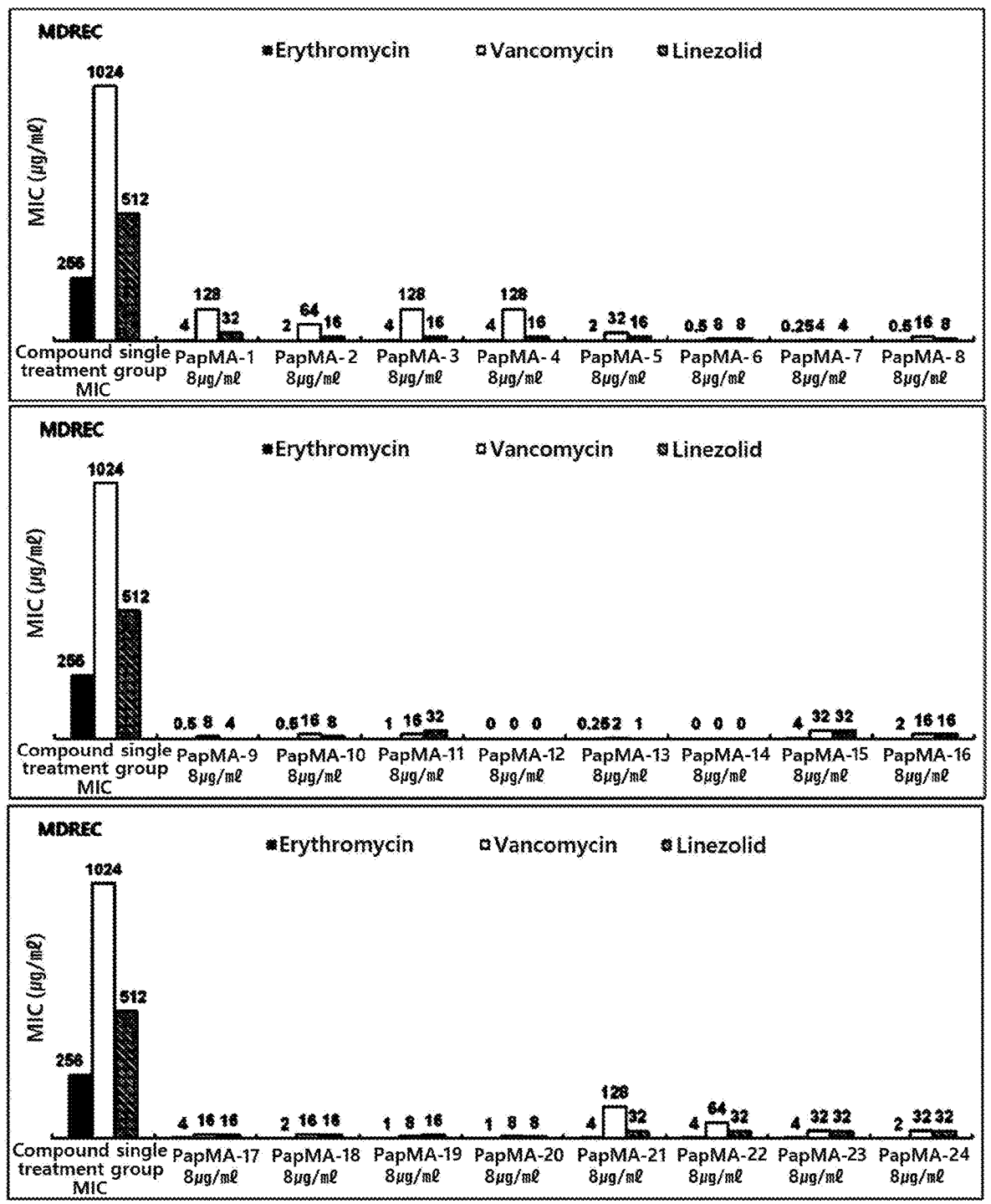
FIG. 2 is a view confirming a synergistic antibacterial activity of PapMA-1 to PapMA-24 (8 μg/ml) and commercially available antibiotics against MDREC, which is a resistant *E. coli* strain.
Figure 3:
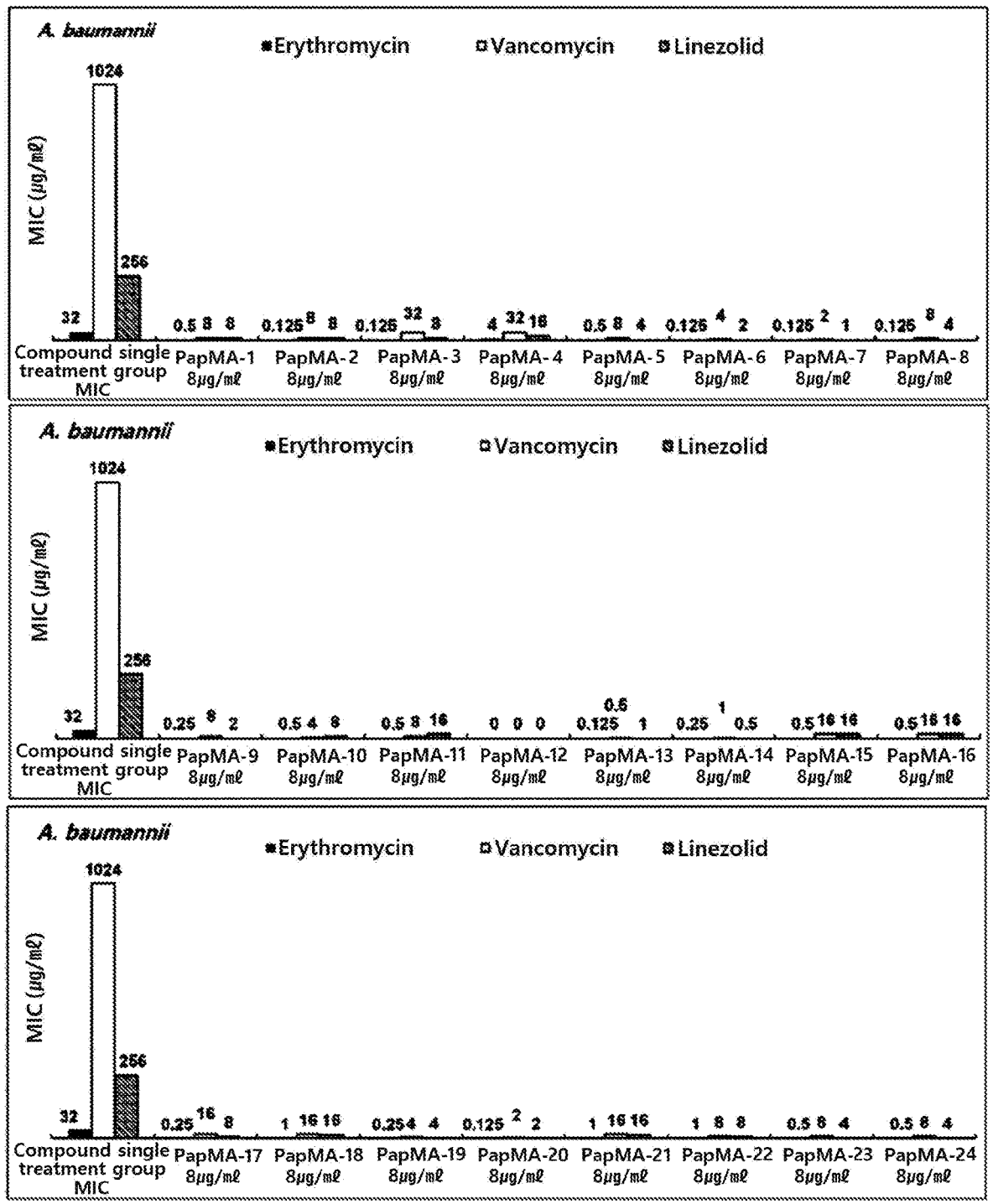
FIG. 3 is a view confirming a synergistic antibacterial activity of PapMA-1 to PapMA-24 (8 μg/ml) and commercially available antibiotics against *A. baumannii* bacteria.
Figure 4:
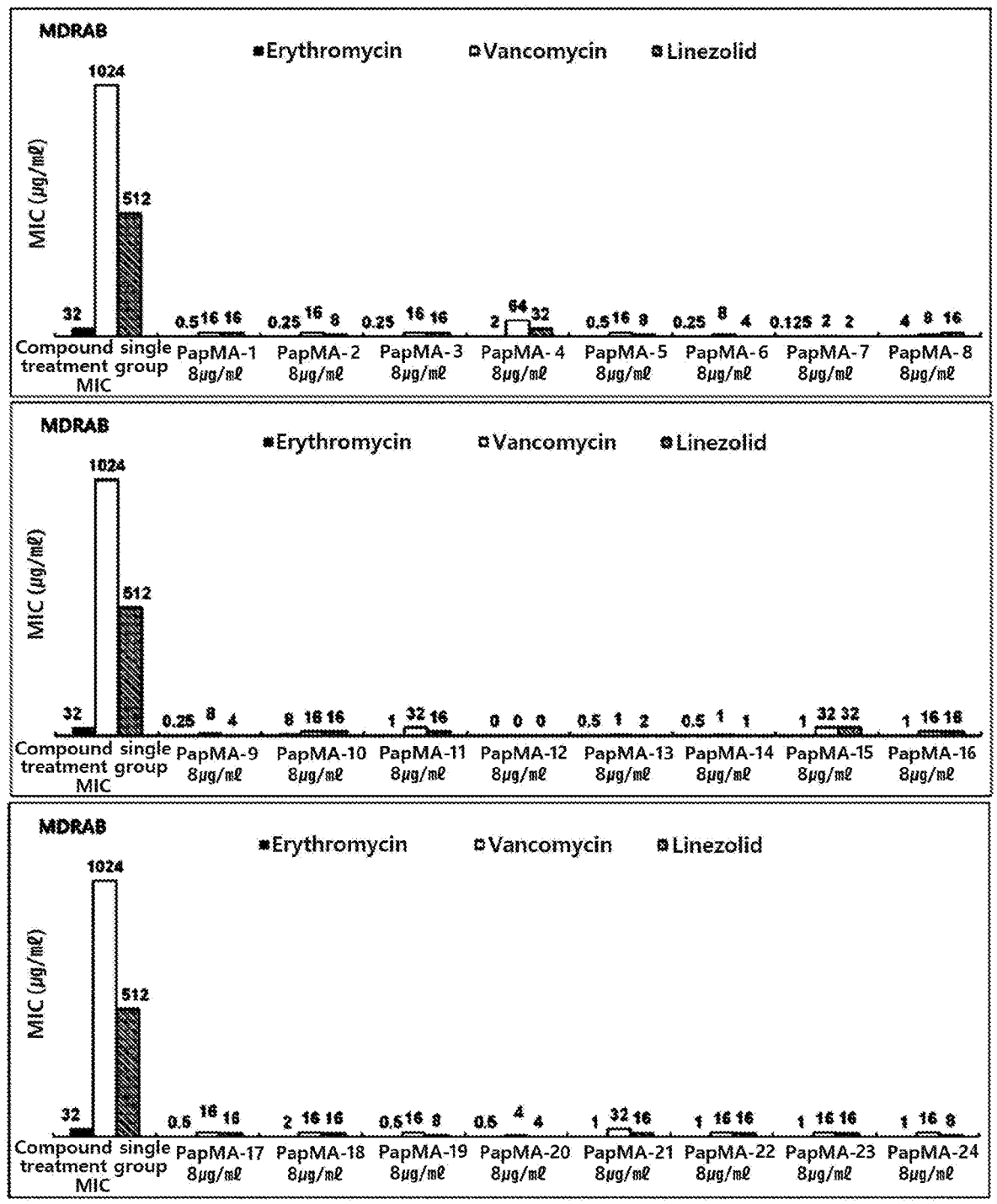
FIG. 4 is a view confirming a synergistic antibacterial activity of PapMA-1 to PapMA-24 (8 μg/ml) and commercially available antibiotics against MDRAB, which is a resistant *A. baumannii* bacterial strain.

Further, as a result of administering PapMA-1 to PapMA-24 together with erythromycin, vancomycin, or linezolid to gram-negative bacteria and antibiotic-resistant strains thereof in order to confirm whether PapMA-1 to PapMA-24 can exhibit a synergistic effect with a conventional antibiotic, the present inventors confirmed that the combinatory administration provided significantly increased antibacterial activity as compared to the antibacterial activity during the treatment of the antibiotics alone (Tables 9 to 33), thereby confirming that the synthetic peptide of the present invention and antibiotics synergistically exhibit significantly increased antibacterial activity (Tables 35 to 38, and FIGS. 1 to 4).

Therefore, PapMA-1 to PapMA-24 which are the antibacterial peptides of the present invention exhibit more significant antibacterial activity against gram-negative bacteria, and exhibit excellent synergistic antibacterial activity against gram-negative bacteria and antibiotic-resistant strains thereof when antibiotics which have significant antibacterial activity against gram-positive bacteria only and has low antibacterial activity against gram-negative bacteria is administered together with the antibacterial peptide of the present invention, so that the antibacterial peptide of the present invention or a combination containing the same together with the antibiotics can be usefully used as an active ingredient of an antibacterial composition.

In addition, the present invention provides an antibacterial pharmaceutical composition containing, as an active ingredient, an antimicrobial peptide consisting of amino acid sequences in which one or more substitutions selected from the group consisting of the following (i) to (v) are performed from a peptide consisting of an amino acid sequence represented by SEQ ID No. 1:

(i) substitution of proline (P) which is the 9th amino acid with D-lysine (k) or D-leucine (l);

(ii) substitution of phenylalanine (F) which is the 11th amino acid with leucine (L);

(iii) substitution of serine (S) which is the 14th amino acid with glutamic acid (E) or L-lysine (K);

(iv) substitution of alanine (A) which is the 15th amino acid with tryptophan (W), phenylalanine (F), or leucine (L); and (v) substitution of phenylalanine (F) which is the 18th amino acid with tryptophan (W).

Furthermore, the present invention provides an antibacterial pharmaceutical composition containing, as active ingredients, the antimicrobial peptide; and an antibiotic.

Further, the present invention provides an antibacterial adjuvant containing the antimicrobial peptide as an active ingredient.

In addition, the present invention provides an antibacterial adjuvant containing, as active ingredients, the antimicrobial peptide; and an antibiotic.

In the sequence of the antimicrobial peptide, by substituting alanine (A) and/or phenylalanine (F) with tryptophan (W), the sequence can be optimized so as to exhibit increased antibacterial activity compared to a peptide consisting of an amino acid sequence of SEQ ID No. 1, or have a higher synergistic effect during the combined treatment with a conventional antibiotic.

In the sequence of the antimicrobial peptide, by substituting phenylalanine (F) with leucine (L); and/or substituting alanine (A) or tryptophan (W) with phenylalanine (F) or leucine (L), the sequence can be optimized so as to exhibit increased antibacterial activity compared to a peptide consisting of amino acid sequences of SEQ ID Nos. 1 to 4, or have a higher synergistic effect during the combined treatment with a conventional antibiotic.

In the sequence of the antimicrobial peptide, by substituting serine (S) with glutamic acid (E), the antimicrobial peptide of the present invention can exhibit increased antibacterial activity compared to a peptide consisting of any one amino acid sequence of SEQ ID Nos. 1 to 10, or the sequence can be optimized so as to have a higher synergistic effect during the combined treatment with a conventional antibiotic.

In the sequence of the antimicrobial peptide, by substituting proline (P) and/or glutamic acid (E) with D-lysine (k) and/or L-lysine (K), the antimicrobial peptide of the present invention can exhibit increased antibacterial activity compared to a peptide consisting of any one amino acid sequence of SEQ ID Nos. 1 to 14, or the sequence can be optimized so as to have a higher synergistic effect during the combined treatment with a conventional antibiotic.

In the sequence of the antimicrobial peptide, by substituting proline (P) or D-lysine (k) with D-leucine (l), the antimicrobial peptide of the present invention can exhibit increased antibacterial activity compared to a peptide consisting of any one amino acid sequence of SEQ ID Nos. 1 to 20, or the sequence can be optimized so as to have a higher synergistic effect during the combined treatment with a conventional antibiotic.

Specifically, the antimicrobial peptide of the present invention preferably consists of any one amino acid sequence selected from the group consisting of SEQ ID Nos. 1 to 24, but is not limited thereto.

As the antibiotics of the present invention, any antibiotics known in the art as having antibacterial activity against gram-positive bacteria and having low or no antibacterial activity against gram-negative bacteria may be used. Specifically, the antibiotics of the present invention are preferably one or more selected from the group consisting of erythromycin, ampicillin, vancomycin, linezolid, methicillin, oxacillin, cefotaxime, rifampicin, amikacin, gentamicin, amikacin, kanamycin, tobramycin, neomycin, ertapenem, doripenem, imipenem/cilastatin, meropenem, ceftazidime, cefepime, ceftaroline, ceftobiprole, aztreonam, piperacillin, polymyxin B, colistin, ciprofloxacin, levofloxacin, moxifloxacin, gatifloxacin, tigecycline, a conjugate thereof, and derivatives thereof, and more specifically, the antibiotics of the present invention are more preferably one or more selected from the group consisting of erythromycin, vancomycin, and linezolid, but is not limited thereto.

The "antibacterial pharmaceutical composition" of the present invention does not have antibacterial activity against gram-positive bacteria, gram-negative bacteria, and antibiotic-resistant strains thereof, and specifically, the antibacterial pharmaceutical composition of the present invention preferably exhibits antibacterial activity against pathogens as follows, but is not limited thereto: *Acinetobacter baumannii, Actinomyces* sp. (for example, *Actinomyces israelii* and *Actinomyces naeslundii*), *Aeromonas* sp. (for example, *Aeromonas hydrophila, Aeromonas veronii biovar sobria* (*Aeromonas sobria*) and *Aeromonas caviae*), *Anaplasma phagocytophilum, Alcaligenes xylosoxidans, Actinobacillus actinomycetemcomitans, Bacillus* sp. (for example, *Bacillus anthracis, Bacillus cereus, Bacillus subtilis, Bacillus thuringiensis,* and *Bacillus stearothermophilus, Bacteroides* sp. (for example, *Bacteroides fragilis*), *Bartonella* sp. (for example, *Bartonella bacilliformis* and *Bartonella henselae*), *Bifidobacterium* sp., *Bordetella* sp. (for example, *Bordetella pertussis, Bordetella parapertussis* and *Bordetella bronchiseptica*), *Borrelia* sp. (for example, *Borrelia recurrentis* and *Borrelia burgdorferi*), *Brucella* sp. (for example, *Brucella abortus, Brucella canis, Brucella melintensis* and *Brucella suis*), *Burkholderia* sp. (for example, *Burkholderia pseudomallei* and *Burkholderia cepacia*), *Campylobacter* sp. (for example, *Campylobacter jejuni, Campylobacter coli, Campylobacter lari* and *Campylobacter fetus*), *Capnocytophaga* sp., *Cardiobacterium hominis, Chlamydia trachomatis, Chlamydophila pneumonia, Chlamydophila psittaci, Citrobacter* sp. *Coxiella burnetii, Corynebacterium* sp. (for example, *Corynebacterium diphtheria, Corynebacterium jeikeum* and *Corynebacterium*), *Clostridium* sp. (for example, *Clostridium perfringens, Clostridium difficile, Clostridium botulinum* and *Clostridium tetani*), *Eikenella corrodens, Enterobacter* sp. (for example, *Enterobacter aerogenes, Enterobacter agglomerans, Enterobacter cloacae* and *Escherichia coli* including opportunistically infectious *Escherichia coli* such as enterotoxigenic *E. Coli*, enteroinvasive *E. Coli*, enteropathogenic *E. Coli*, enterohemorrhagic *E. Coli*, enteroaggregative *E. Coli* and Uropathogenic *E. coli*), *Enterococcus* sp. (for example, *Enterococcus faecalis* and *Enterococcus faecium*), *Ehrlichia* sp. (for example, *Ehrlichia chafeensia* and *Ehrlichia canis*), *Erysipelothrix rhusiopathiae*, *Eubacterium* sp., *Francisella tularensis*, *Fusobacterium nucleatum*, *Gardnerella vaginalis*, *Gemella morbillorum*, *Haemophilus* sp. (for example, *Haemophilus influenzae*, *Haemophilus ducreyi*, *Haemophilus aegyptius*, *Haemophilus parainfluenzae*, *Haemophilus haemolyticus* and *Haemophilus parahaemolyticus*), *Helicobacter* sp. (for example, *Helicobacter pylori*, *Helicobacter cinaedi* and *Helicobacter fennelliae*), *Kingella kingii*, *Klebsiella* sp. (for example, *Klebsiella pneumoniae*, *Klebsiella granulomatis* and *Klebsiella oxytoca*), *Lactobacillus* sp., *Listeria monocytogenes*, *Leptospira* interrogans, Legionella pneumophila, *Leptospira interrogans*, *Peptostreptococcus* sp., *Moraxella catarrhalis*, *Morganella* sp., *Mobiluncus* sp., *Micrococcus* sp., *Mycobacterium* sp. (for example, *Mycobacterium leprae*, *Mycobacterium intracellulare*, *Mycobacterium avium*, *Mycobacterium bovis* and *Mycobacterium marinum*), *Mycoplasm* sp. (for example, *Mycoplasma pneumoniae*, *Mycoplasma hominis* and *Mycoplasma genitalium*), *Nocardia* sp. (for example, *Nocardia asteroides*, *Nocardia cyriacigeorgica* and *Nocardia brasiliensis*), *Neisseria* sp. (for example, *Neisseria gonorrhoeae* and *Neisseria meningitidis*), *Pasteurella multocida*, *Plesiomonas shigelloides*, *Prevotella* sp., *Porphyromonas* sp., *Prevotella melaninogenica*, *Proteus* sp. (for example, *Proteus vulgaris* and *Proteus mirabilis*), *Providencia* sp. (for example, *Providencia alcalifaciens*, *Providencia rettgeri* and *Providencia stuartii*), *Pseudomonas aeruginosa*, *Propionibacterium acnes*, *Rhodococcus equi*, *Salmonella* sp. (for example, *Salmonella enterica*, *Salmonella typhi*, *Salmonella paratyphi*, *Salmonella enteritidis*, *Salmonella cholerasuis* and *Salmonella typhimurium*, *Serratia* sp. (for example, *Serratia marcesans* and *Serratia liquifaciens*), *Shigella* sp. (for example, *Shigella dysenteriae*, *Shigella flexneri*, *Shigella boydii* and *Shigella sonnei*), *Staphylococcus* sp. (for example, *Staphylococcus aureus*, *Staphylococcus epidermidis*, *Staphylococcus hemolyticus*, and *Staphylococcus saprophyticus*), *Streptococcus* sp. (for example, *Streptococcus pneumoniae*, Spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, Tetracycline-resistant serotype 19F *Streptococcus pneumoniae*, penicillin-resistant serotype 19F *Streptococcus pneumoniae* and trimethoprim-resistant serotype 23F *Streptococcus pneumoniae*, chloramphenicol-resistant serotype 4 *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae* or trimethoprim-resistant serotype 23F *Streptococcus pneumoniae*, *Streptococcus agalactiae*, *Streptococcus mutans*, *Streptococcus pyogenes*, Group A streptococci, *Streptococcus pyogenes*, Group B streptococci, *Streptococcus agalactiae*, Group C streptococci, *Streptococcus anginosus*, *Streptococcus equismilis*, Group D streptococci, *Streptococcus bovis*, Group F streptococci and *Streptococcus anginosus*, Group G streptococci, *Spirillum minus*, *Streptobacillus moniliformi*, *Treponema* sp. (for example, *Treponema carateum*, *Treponema petenue*, *Treponema pallidum* and *Treponema endemicum*), *Tropheryma whippelii*, *Ureaplasma urealyticum*, *Veillonella* sp., *Vibrio* sp. (for example, *Vibrio cholerae*, *Vibrio parahemolyticus*, *Vibrio vulnificus*, *Vibrio parahaemolyticus*, *Vibrio vulnificus*, *Vibrio alginolyticus*, *Vibrio mimicus*, *Vibrio hollisae*, *Vibrio fluvialis*, *Vibrio metchnikovii*, *Vibrio damsela* and *Vibrio furnisii*), *Yersinia* sp. (for example, *Yersinia enterocolitica* and *Yersinia pestis*) and *Xanthomonas maltophilia*.

It is preferred that the gram-positive bacteria are all the gram-positive bacteria known in the art as being gram-positive bacteria, including *Staphylococcus* sp., *Listeria* sp., *Streptococcus* sp., *Corynebacterium* sp., *Lactobacillus* sp., *Clostridium* sp., *Enterococcus* sp., *Erysipelothrix* sp., and *Bacillus* genus, and it is more preferred that the gram-positive bacteria are *Bacillus subtilis*, *Staphylococcus aureus* or *Staphylococcus epidermidis*, but the gram-positive bacteria are not limited thereto, and preferably, the gram-positive bacteria may include antibiotic-resistant strains thereof.

It is preferred that the gram-negative bacteria are all the gram-negative bacteria known in the art as being gram-negative bacteria, including *Escherichia* sp., *Pseudomonas* sp., *Salmonella* sp., *Leptospira* sp., and *Rickettsia* sp., and it is more preferred that the gram-negative bacteria are *Escherichia coli*, *Pseudomonas aeruginosa*, *Acinetobacter baumannii* or *Salmonella typhimurium*, and specifically, it is most preferred that the gram-negative bacteria are either *Escherichia coli* or *Acinetobacter baumannii*, but the gram-negative bacteria are not limited thereto, and preferably, the gram-negative bacteria may include antibiotic-resistant strains thereof.

Since the antimicrobial peptide of the present invention exhibits a significant synergistic antibacterial effect on gram-negative bacteria and antibiotic-resistant strains thereof during the combined treatment with an existing antibiotic, a combination of the antimicrobial peptide and the antibiotics of the present invention may be usefully used as an active ingredient of an antibacterial pharmaceutical composition.

The antibacterial pharmaceutical composition of the present invention can be non-orally administered, and may be used in the form of a general medicinal preparation. The parenteral administration may mean the administration via an administration route other than an oral route, such as rectal, venous, peritoneal, muscular, arterial, transdermal, nasal, inhalation, ocular, and subcutaneous routes. When the antibacterial pharmaceutical composition of the present invention is used as a medicine, it may further contain one or more active ingredients exhibiting the same or similar function.

That is, the antibacterial pharmaceutical composition of the present invention may be actually administered as various parenteral dosage forms, and during the formulation, the antibacterial pharmaceutical composition of the present invention is prepared by using a commonly used diluent or excipient, such as a filler, an extender, a binder, a wetting agent, a disintegrant, and a surfactant. Examples of a preparation for parenteral administration include an aqueous sterile solution, a non-aqueous solvent, a suspension solvent, an emulsion, a freeze-dried preparation, a suppository, or the like. As the non-aqueous solvent and the suspension solvent, it is possible to use propylene glycol, polyethylene glycol, a vegetable oil such as olive oil, an injectable ester such as ethyl oleate, and the like. As a base of the suppository, it is possible to use Witepsol, Macrogol, Tween 61, cacao butter, laurin fat, glycerogelatin, and the like.

Further, the antibacterial pharmaceutical composition of the present invention can be used in combination with various pharmaceutically acceptable carriers such as physiological saline or organic solvent, and carbohydrates such as glucose, sucrose or dextran, antioxidants such as ascorbic acid or glutathione, chelating agents, low molecular proteins or other stabilizers can be used as a medicine in order to enhance stability or absorptiveness.

An effective dose of the antibacterial pharmaceutical composition of the present invention is 0.01 to 100 mg/kg, preferably 0.1 to 10 mg/kg, and the antibacterial pharmaceutical composition of the present invention can be administered once to three times daily.

In the pharmaceutical composition of the present invention, a total effective amount of an antimicrobial peptide or a combination of the antimicrobial peptide and antibiotics may be administered as a single dose to a patient in the form of a bolus or by infusion and the like for a relatively short period of time, and may be administered by a fractionated treatment protocol in which it is administered as multiple doses for a long period of time. For the concentration, an effective dose of a patient is determined in consideration of the administration route of a drug and number of treatments and various factors such as age and health status of a patient, so that in consideration of these circumstances, a person with ordinary skill in the art will be able to determine appropriately an effective dose according to the specific use as the pharmaceutical composition of the present invention.

When antibiotics are administered, the antibacterial adjuvant of the present invention may be administered concurrently with the antibiotic, before treatment with the antibiotic, or after treatment with the antibiotic, and it may be used as an adjuvant for enhancing the antibacterial activity of the antibiotic. The adjuvant preferably has a synergistic effect on antibacterial activity with antibiotics and preferably increases antibacterial activity of the antibiotics against gram-negative bacteria and antibiotic-resistant strains thereof.

In addition, the present invention provides a food additive containing, as an active ingredient, an antimicrobial peptide consisting of amino acid sequences in which one or more substitutions selected from the group consisting of the following (i) to (v) are performed from a peptide consisting of an amino acid sequence represented by SEQ ID No. 1:

(i) substitution of proline (P) which is the 9th amino acid with D-lysine (k) or D-leucine (l);

(ii) substitution of phenylalanine (F) which is the 11th amino acid with leucine (L);

(iii) substitution of serine (S) which is the 14th amino acid with glutamic acid (E) or L-lysine (K);

(iv) substitution of alanine (A) which is the 15th amino acid with tryptophan (W), phenylalanine (F), or leucine (L); and (v) substitution of phenylalanine (F) which is the 18th amino acid with tryptophan (W).

Furthermore, the present invention provides a food additive containing, as active ingredients, the antimicrobial peptide; and an antibiotic.

In the food additive of the present invention, the antimicrobial peptide preferably consists of any one amino acid sequence selected from the group consisting of SEQ ID Nos. 1 to 24, but is not limited thereto, and may be a derivative thereof and a functional equivalent thereof.

Since the antimicrobial peptide of the present invention exhibits a significant synergistic antibacterial effect on gram-negative bacteria and antibiotic-resistant strains thereof during the combined treatment with an existing antibiotic, the antimicrobial peptide or the combination of the antimicrobial peptide and the antibiotics of the present invention can be usefully used as an active ingredient of a food additive.

When the antimicrobial peptide or the combination of the antimicrobial peptide and the antibiotics of the present invention is used as a food additive, the antimicrobial peptide, or the combination of the antimicrobial peptide and the antibiotics may be added as is or may be used together with other food ingredients, and may be used appropriately according to a typical method. A mixture amount of the active ingredient may be determined appropriately according to the use thereof. In general, the antimicrobial peptide or the combination of the antimicrobial peptide and the antibiotics of the present invention is added in an amount of 15 parts by weight or less, preferably 10 parts by weight or less based on the raw material. However, in the case of intake for a long period of time, the amount may be equal to or less than the above range, and the active ingredient may also be used in an amount equal to or more than the above range because there is no problem in terms of safety.

The type of food is not particularly limited. Examples of food to which the material may be added include meats, sausage, bread, chocolate, candies, snacks, confectioneries, pizza, instant noodles, other noodles, gums, dairy products including ice creams, various soups, beverage, tea, drinks, alcoholic beverages, vitamin complexes, and the like, and include the entire class of foods in a typical sense.

In addition, the present invention provides a feed additive containing, as an active ingredient, an antimicrobial peptide consisting of amino acid sequences in which one or more substitutions selected from the group consisting of the following (i) to (v) are performed from a peptide consisting of an amino acid sequence represented by SEQ ID No. 1:

(i) substitution of proline (P) which is the 9th amino acid with D-lysine (k) or D-leucine (l);

(ii) substitution of phenylalanine (F) which is the 11th amino acid with leucine (L);

(iii) substitution of serine (S) which is the 14th amino acid with glutamic acid (E) or L-lysine (K);

(iv) substitution of alanine (A) which is the 15th amino acid with tryptophan (W), phenylalanine (F), or leucine (L); and (v) substitution of phenylalanine (F) which is the 18th amino acid with tryptophan (W).

Furthermore, the present invention provides a feed additive containing, as active ingredients, the antimicrobial peptide; and an antibiotic.

In the feed additive of the present invention, the antimicrobial peptide preferably consists of any one amino acid sequence selected from the group consisting of SEQ ID Nos. 1 to 24, but is not limited thereto, and it may be a derivative thereof and a functional equivalent thereof.

Since the antimicrobial peptide of the present invention exhibits a significant synergistic antibacterial effect on gram-negative bacteria and antibiotic-resistant strains thereof during the combined treatment with an existing antibiotic, the antimicrobial peptide or the combination of the antimicrobial peptide and the antibiotics of the present invention can be usefully used as an active ingredient of a feed additive.

The feed additive of the present invention has effects of improve the health condition of the cattle, improving the body weight gain and meat quality of livestock, and increasing the milk yield and immunity by replacing the existing antibiotics and inhibiting the growth of harmful food pathogens. The feed additive of the present invention may be prepared in the form of a fermented feed, a blended feed, a pellet, a silage, and the like.

The fermented feed can be prepared by adding various microorganism groups or enzymes in addition to the antimicrobial peptide or the combination of the antimicrobial peptide and the antibiotics of the present invention in order to ferment organic materials, and the blended feed can be prepared by mixing various types of general feeds with the combination of the peptide and the antibiotics of the present invention. The feed in the form of a pellet may be prepared by applying heat and pressure to the blended feed, and the like in a pellet machine, and the silage may be prepared by fermenting a green fodder with microorganisms. A wet fermented feed may be prepared by collecting and transporting organic materials such as food waste, mixing it with an excipient for adjusting a sterilization process and moisture at a predetermined ratio, and then fermenting the mixture at a temperature suitable for fermentation for 24 hours or more, and adjusting the moisture content so as to be about 70%. A fermented dry feed may be prepared by additionally subjecting the wet fermented feed to a drying process and adjusting the moisture content so as to be 30% to 40%.

Further, the present invention provides an antiseptic composition containing, as an active ingredient, an antimicrobial peptide consisting of amino acid sequences in which one or more substitutions selected from the group consisting of the following (i) to (v) are performed from a peptide consisting of an amino acid sequence represented by SEQ ID No. 1:

(i) substitution of proline (P) which is the 9th amino acid with D-lysine (k) or D-leucine (l);

(ii) substitution of phenylalanine (F) which is the 11th amino acid with leucine (L);

(iii) substitution of serine (S) which is the 14th amino acid with glutamic acid (E) or L-lysine (K);

(iv) substitution of alanine (A) which is the 15th amino acid with tryptophan (W), phenylalanine (F), or leucine (L); and (v) substitution of phenylalanine (F) which is the 18th amino acid with tryptophan (W).

Furthermore, the present invention provides an antiseptic composition containing, as active ingredients, the antimicrobial peptide; and an antibiotic.

In the antiseptic composition of the present invention, the antimicrobial peptide preferably consists of any one amino acid sequence selected from the group consisting of SEQ ID Nos. 1 to 24, but is not limited thereto, and it may be a derivative thereof and a functional equivalent thereof.

Examples of the antiseptic composition include a food preservative, a cosmetic preservative, a medical preservative, and the like. The food preservative, the cosmetic preservative, and the medical preservative are additives used for preventing deterioration, decay, discoloration, and chemical change of a medicine, include a sterilizer and an antioxidant, and also include a functional antibiotics which inhibit the growth of decayed microorganisms or sterilizes bacteria, and the like in food and medicine by inhibiting the proliferation of microorganisms such as bacteria, fungi, and yeasts. An ideal condition for the antiseptic composition is that it is non-toxic and produces an effect even in trace amount.

Further, the present invention provides an antibacterial quasi-drug containing, as an active ingredient, an antimicrobial peptide consisting of amino acid sequences in which one or more substitutions selected from the group consisting of the following (i) to (v) are performed from a peptide consisting of an amino acid sequence represented by SEQ ID No. 1:

(i) substitution of proline (P) which is the 9th amino acid with D-lysine (k) or D-leucine (l);

(ii) substitution of phenylalanine (F) which is the 11th amino acid with leucine (L);

(iii) substitution of serine (S) which is the 14th amino acid with glutamic acid (E) or L-lysine (K);

(iv) substitution of alanine (A) which is the 15th amino acid with tryptophan (W), phenylalanine (F), or leucine (L); and (v) substitution of phenylalanine (F) which is the 18th amino acid with tryptophan (W).

Furthermore, the present invention provides an antibacterial quasi-drug containing, as active ingredients, the antimicrobial peptide; and an antibiotic.

In the antibacterial quasi-drug of the present invention, the antimicrobial peptide preferably consists of any one amino acid sequence selected from the group consisting of SEQ ID Nos. 1 to 24, but is not limited thereto, and it may be a derivative thereof and a functional equivalent thereof.

Since the antimicrobial peptide of the present invention exhibits a significant synergistic antibacterial effect on gram-negative bacteria and antibiotic-resistant strains thereof during the combined treatment with an existing antibiotic, the antimicrobial peptide or the combination of the antimicrobial peptide and the antibiotics of the present invention can be usefully used as an active ingredient of a food additive.

When the composition of the present invention is used as a quasi-drug additive, the combination of the peptide and the antibiotics of the present invention may be added as is or may be used together with other quasi-drugs or quasi-drug ingredients, and may be used appropriately according to a typical method. A mixture amount of the active ingredient may be determined appropriately according to the use thereof.

The quasi-drug composition of the present invention is not limited to, but may be preferably disinfectant cleaner, shower foam, mouth wash, wet wipes, detergent soap, hand wash, humidifier filler, mask, ointment, patch, or filter filler.

EXAMPLES

<Example 1> Synthesis of Antimicrobial Peptide

In order to target a peptide exhibiting antibacterial activity against gram-negative bacteria and multi-drug resistant strains thereof, an antimicrobial peptide (PapMA-1) of an amino acid sequence represented by SEQ ID No. 1 was designed by designing a sequence in which an N-terminal residue of papiliocin which is an antimicrobial peptide was linked to an N-terminal residue of magainin (Shin et al. Biochemistry. 2015 Jun. 30; 54(25):3921-31).

From the antimicrobial peptide (PapMA-1) of the amino acid sequence represented by SEQ ID No. 1, antimicrobial peptides (PapMA-2 to PapMA-4) of amino acid sequences represented by SEQ ID Nos. 2 to 4 were designed by substituting alanine (A) which is the 15th amino acid with tryptophan (W); and/or substituting phenylalanine (F) which is the 18th amino acid with tryptophan (W).

And then, from the antimicrobial peptides of the amino acid sequences represented by SEQ ID Nos. 1 to 4, antimicrobial peptides (PapMA-5 to PapMA-10) of amino acid sequences represented by SEQ ID Nos. 5 to 10 were designed by substituting phenylalanine (F) which is the 11th amino acid with leucine (L); and/or substituting alanine (A) or tryptophan (W) which is the 15th amino acid with phenylalanine (F) or leucine (L).

Further, from the antimicrobial peptides of the amino acid sequences represented by SEQ ID Nos. 1 to 10, antimicrobial peptides (PapMA-11 to PapMA-14) represented by SEQ ID Nos. 11 to 14 were designed by substituting serine (S) which is the 14th amino acid with glutamic acid (E).

In addition, from the antimicrobial peptides of the amino acid sequences represented by SEQ ID Nos. 2 to 14, antimicrobial peptides (PapMA-15 to PapMA-20) represented by SEQ ID Nos. 15 to 20 were designed by substituting proline (P) with D-lysine (k); and/or substituting glutamic acid (E) which is the 14th amino acid with L-lysine (K).

Further, from the antimicrobial peptides of the amino acid sequences represented by SEQ ID Nos. 1 to 20, antimicrobial peptides (PapMA-21 to PapMA-24) represented by SEQ ID Nos. 21 to 24 were designed by substituting proline (P) or D-lysine (k) which is the 9th amino acid with D-leucine (l).

For the designed peptide sequences, peptides were synthesized by a solid-phase synthesis method using a method of synthesizing N-(9-fluorenyl)methoxycarbonyl (Fmoc), and were purified (*Biochimica et Biophysica Acta (BBA)-Biomembranes* 1798.10 (2010): 1913-1925). And then, the concentration of the synthesized peptide was quantified by using a UV spectrophotometer, and the purity (>98%) of the final peptide was analyzed by reverse-phase high performance liquid chromatography.

As a result, antibacterial peptides consisting of amino acid sequences of SEQ ID Nos. 1 to 24 were synthesized as shown in the following [Table 1].

TABLE 1

Sequence of peptide synthesized in the present invention

| Name of peptide | Amino acid sequence | SEQ ID No. | Net charge |
|---|---|---|---|
| PapMA-1 | RWK IFK KIP KFL HSA KKF-NH2 | SEQ ID No. 1 | +8 |
| PapMA-2 | RWK IFK KIP KFL HSA KK<u>W</u>-NH2 | SEQ ID No. 2 | +8 |
| PapMA-3 | RWK IFK KIP KFL HS<u>W</u> KKF-NH2 | SEQ ID No. 3 | +8 |
| PapMA-4 | RWK IFK KIP KFL HS<u>W</u> KK<u>W</u>-NH2 | SEQ ID No. 4 | +8 |
| PapMA-5 | RWK IFK KIP KFL HS<u>F</u> KKF-NH2 | SEQ ID No. 5 | +8 |
| PapMA-6 | RWK IFK KIP KFL HS<u>L</u> KKF-NH2 | SEQ ID No. 6 | +8 |
| PapMA-7 | RWK IFK KIP K<u>L</u>L HS<u>F</u> KKF-NH2 | SEQ ID No. 7 | +8 |
| PapMA-8 | RWK IFK KIP K<u>L</u>L HS<u>L</u> KKF-NH2 | SEQ ID No. 8 | +8 |
| PapMA-9 | RWK IFK KIP K<u>L</u>L HSA KK<u>W</u>-NH2 | SEQ ID No. 9 | +8 |
| PapMA-10 | RWK IFK KIP K<u>L</u>L HS<u>L</u> KK<u>W</u>-NH2 | SEQ ID No. 10 | +8 |
| PapMA-11 | RWK IFK KIP KFL H<u>EA</u> KKF-NH2 | SEQ ID No. 11 | +7 |
| PapMA-12 | RWK IFK KIP K<u>LL</u> H<u>EF</u> KKF-NH2 | SEQ ID No. 12 | +7 |
| PapMA-13 | RWK IFK KIP K<u>LL</u> H<u>EA</u> KK<u>W</u>-NH2 | SEQ ID No. 13 | +7 |
| PapMA-14 | RWK IFK KIP KFL H<u>EA</u> KK<u>W</u>-NH2 | SEQ ID No. 14 | +7 |
| PapMA-15 | RWK IFK KI<u>k</u> K<u>LL</u> HS<u>F</u> KKF-NH2 | SEQ ID No. 15 | +9 |
| PapMA-16 | RWK IFK KI<u>k</u> K<u>LL</u> HSA KK<u>W</u>-NH2 | SEQ ID No. 16 | +9 |
| PapMA-17 | RWK IFK KI<u>k</u> K<u>LL</u> H<u>KF</u> KKF-NH2 | SEQ ID No. 17 | +10 |
| PapMA-18 | RWK IFK KI<u>k</u> K<u>LL</u> H<u>KA</u> KK<u>W</u>-NH2 | SEQ ID No. 18 | +10 |
| PapMA-19 | RWK IFK KI<u>k</u> K<u>LL</u> H<u>EF</u> KKF-NH2 | SEQ ID No. 19 | +8 |
| PapMA-20 | RWK IFK KI<u>k</u> K<u>LL</u> H<u>EA</u> KK<u>W</u>-NH2 | SEQ ID No. 20 | +8 |
| PapMA-21 | RWK IFK KI<u>l</u> K<u>LL</u> H<u>KF</u> KKF-NH2 | SEQ ID No. 21 | +9 |
| PapMA-22 | RWK IFK KI<u>l</u> K<u>LL</u> H<u>KA</u> KK<u>W</u>-NH2 | SEQ ID No. 22 | +9 |
| PapMA-23 | RWK IFK KI<u>l</u> K<u>LL</u> H<u>EF</u> KKF-NH2 | SEQ ID No. 23 | +7 |
| PapMA-24 | RWK IFK KI<u>l</u> K<u>LL</u> H<u>EA</u> KK<u>W</u>-NH2 | SEQ ID No. 24 | +7 |

<Example 2> Identification of Antibacterial Activity of Antimicrobial Peptide

<2-1> Identification of Antibacterial Activity of Antimicrobial Peptide Against Gram-Positive Bacteria and Gram-Negative Bacteria In order to compare an antibacterial activity which the antimicrobial peptide of the present invention exhibited, an antibacterial activity which the antimicrobial peptide or an existing antibiotics exhibited against gram-negative bacteria and gram-positive bacteria was measured. For the antibacterial activity, a minimal inhibitory concentration (MIC) of a peptide in which fungus bodies were not split in an MH medium with sufficient nutrients was measured.

Specifically, the strains described in the following [Table 2] were purchased and diluted with an MH medium such that the number of bacteria was $2\times10^6$ colony-forming units (CFUs), 100 μl of each of the diluted strains was aliquoted into a 96-well microtiter plate, and then 100 μl of a peptide solution diluted with the MH medium (solution diluted stepwise at 2: 1) was added to each well. After the plate was incubated at 37° C. for 16 hours, the MIC of the peptide was determined by measuring the absorbance of each well at 620 nm using an ELISA reader (Bio-Tek Instruments). When the MIC value was found to be equal to or greater than the corresponding concentration, a subsequent experiment was performed by supposing the MIC at the corresponding concentration.

TABLE 2

| Classification | Strain name | Accession No. | Source |
|---|---|---|---|
| Gram-positive bacteria | Bacillus subtilis | KCTC 3068 | Korean Collection for Type Cultures |
| | Staphylococcus aureus | KCTC 1621 | |
| | Staphylococcus epidermidis | KCTC 1917 | |
| Gram-negative bacteria | Escherichia coli | KCTC 1682 | Korean Collection for Type Cultures |
| | Pseudomonas aeruginosa | KCTC 1637 | |
| | Acinetobacter baumannii | KCTC 2508 | |
| | Salmonella typhimurium | KCTC 1926 | |
| Antibiotic-resistant strain | MDREC | CCARM 1229 | Culture collection of antimicrobial resistant microbe |
| | MDREC | CCARM 1238 | |
| | MDRAB | CCARM 12035 | |
| | MDRAB | CCARM 12035 | |
| | MDRPA | CCARM 2002 | |
| | MDRPA | CCARM 2003 | |
| | MDRST | CCARM 8007 | |
| | MDRST | CCARM 8009 | |
| | MRSA | CCARM 3114 | |
| | MRSA | CCARM 3126 | |
| | MRSA | | |

Strains used in the present invention and sources thereof

As a result, as shown in the following [Table 3] to [Table 7], it was confirmed that the peptides of SEQ ID Nos. 1 to 24 had high antibacterial activity against all the gram-negative bacteria.

First, it could be seen that the peptides PapMA-2, PapMA-3 and PapMA-4 of SEQ ID Nos. 2 to 4 exhibited 4 times higher antibacterial activity than PapMA-1 which is a peptide parent against *A. baumannii* among gram-negative bacteria, and antibiotic-resistant strains thereof. In particular, PapMA-2, PapMA-3, and PapMA-4 peptides exhibited antibacterial activity comparable to papiliocin or melittin which is a comparative peptide known to have high antibacterial activity against gram-negative bacteria. It was confirmed that these peptides and an antimicrobial peptide papiliocin used as a comparative control selectively had very high antibacterial activity against all the gram-negative bacterial and very low antibacterial activity against gram-positive bacteria (Table 3).

TABLE 3

Minimal inhibitory concentration MIC (μg/ml)

| Target strain | PapMA-1 SEQ ID No. 1 | PapMA-2 SEQ ID No. 2 | PapMA-3 SEQ ID No. 3 | PapMA-4 SEQ ID No. 4 | Comparative peptide Papliocin SEQ ID No. 25 | Comparative peptide Melittin SEQ ID No. 27 |
|---|---|---|---|---|---|---|
| E. coli | 64 | 64 | 32 | 16 | 8 | 16 |
| MDREC 1229 | 64 | 64 | 32 | 32 | 8 | 16 |
| MDREC 1238 | 64 | 64 | 64 | 32 | 16 | 32 |
| P. aeruginosa | 16 | 16 | 16 | 16 | 16 | 8 |
| MDRPA 2002 | 16 | 16 | 16 | 16 | 16 | 16 |
| MDRPA 2003 | 32 | 16 | 16 | 16 | 16 | 16 |
| A. baumannii | 64 | 16 | 16 | 16 | 8 | 8 |
| MDRAB 12035 | 64 | 16 | 16 | 16 | 8 | 8 |
| MDRAB 12036 | 64 | 16 | 16 | 16 | 16 | 16 |
| S. typhimurium | 64 | 32 | 32 | 32 | 16 | 32 |
| MDRST 8007 | 64 | 32 | 32 | 32 | 16 | 32 |
| MDRST 8009 | 64 | 64 | 64 | 32 | 16 | 32 |
| B. subtilis | >128 | >128 | >128 | >128 | >128 | 32 |
| S. epidermidis | >128 | >128 | >128 | >128 | >128 | 16 |
| S. aureus | >128 | >128 | >128 | >128 | >128 | 8 |
| MRSA 3114 | >128 | >128 | >128 | >128 | >128 | 8 |
| MRSA 3126 | >128 | >128 | >128 | >128 | >128 | 16 |

Antibacterial Activity of PapMA-1 to PapMA-4 Peptides against Gram-Negative Bacteria, Gram-Positive Bacteria and Antibiotic-Resistant Strains Thereof As a result of identifying antibacterial activity for peptides PapMA-5 to PapMA-10, as shown in the following [Table 4], it was confirmed that the peptides of SEQ ID Nos. 5 to 10 had high antibacterial activity against all the gram-negative bacteria. It was confirmed that particularly, the PapMA-7, PapMA-8, PapMA-9 and PapMA-10 peptides of SEQ ID Nos. 7 to 10 had antibacterial activity at least twice as high as that of PapMA-1 against E. coli among gram-negative bacteria, and thus exhibited higher antibacterial activity than PapMa-1. It was confirmed that particularly, PapMA-7 and PapMA-8 peptides had the same or higher antibacterial activity against most of the gram-negative bacteria than PapMA-1, PapMA-2, PapMA-3, and PapMA-4. In addition, PapMA-6, PapMa-7 and PapMA-8 peptides exhibited significantly increased antibacterial activity against P. aeruginosa and S. typhimurium among gram-negative bacteria, thereby exhibiting comparable antibacterial activity to that of papiliocin or melittin which is a comparative peptide known to have high antibacterial activity against gram-negative bacteria (Table 4).

TABLE 4

Minimal inhibitory concentration MIC (μg/ml)

| Target strain | PapMA-1 SEQ ID No. 1 | PapMA-5 SEQ ID No. 5 | PapMA-6 SEQ ID No. 6 | PapMA-7 SEQ ID No. 7 | PapMA-8 SEQ ID No. 8 | PapMA-9 SEQ ID No. 9 | PapMA-10 SEQ ID No. 10 |
|---|---|---|---|---|---|---|---|
| E. coli | 64 | 64 | 64 | 32 | 32 | 32 | 32 |
| MDREC 1229 | 64 | 64 | 64 | 64 | 64 | 64 | 64 |
| MDREC 1238 | 64 | 64 | 64 | 64 | 64 | 64 | 64 |
| P. aeruginosa | 16 | 16 | 16 | 16 | 16 | 8 | 8 |
| MDRPA 2002 | 16 | 16 | 32 | 16 | 16 | 16 | 8 |
| MDRPA 2003 | 32 | 16 | 32 | 16 | 16 | 16 | 16 |
| A. baumannii | 64 | 64 | 32 | 16 | 32 | 32 | 16 |
| MDRAB 12035 | 64 | 64 | 64 | 32 | 64 | 64 | 32 |
| MDRAB 12036 | 64 | 64 | 64 | 32 | 64 | 64 | 32 |
| S. typhimurium | 64 | 64 | 16 | 16 | 32 | 32 | 16 |
| MDRST 8007 | 64 | 64 | 32 | 32 | 64 | 64 | 32 |
| MDRST 8009 | 64 | 64 | 64 | 32 | 64 | 64 | 32 |
| B. subtilis | >128 | >128 | >128 | >128 | >128 | >128 | >128 |
| S. epidermidis | >128 | >128 | >128 | >128 | >128 | >128 | >128 |
| S. aureus | >128 | >128 | >128 | >128 | >128 | >128 | >128 |
| MRSA 3114 | >128 | >128 | >128 | >128 | >128 | >128 | >128 |
| MRSA 3126 | >128 | >128 | >128 | >128 | >128 | >128 | >128 |

Antibacterial Activity of PapMA-5 to PapMA-10 Peptides against Gram-Negative Bacteria, Gram-Positive Bacteria and Antibiotic-Resistant Strains Thereof It was confirmed that the peptides of SEQ ID Nos. 11 to 14 had high antibacterial activity against all the gram-negative bacteria, as shown in the following [Table 5]. It was confirmed that the peptides of SEQ ID Nos. 11 to 14 exhibited significantly higher antibacterial activity against A. baumannii and S. typhimurium than the peptide of SEQ ID No. 1 (PapMA-1), and that PapMA-12, PapMA-13, and PapMA-14 exhibited antibacterial activity at least twice as high as that of PaPMA-1.

Together with this, the peptides of SEQ ID Nos. 11 to 14 exhibited excellent antibacterial activity even against multi-drug resistant bacteria, so that it was confirmed that PapMA-12, PapMA-13, and PapMA-14 exhibited twice to four times higher antibacterial activity than PapMA-1.

TABLE 5

| Target strain | Minimal inhibitory concentration MIC (µg/ml) | | | | |
|---|---|---|---|---|---|
| | PapMA-1 SEQ ID No. 1 | PapMA-11 SEQ ID No. 11 | PapMA-12 SEQ ID No. 12 | PapMA-13 SEQ ID No. 13 | PapMA-14 SEQ ID No. 14 |
| E. coli | 64 | 64 | 8 | 16 | 8 |
| MDREC 1229 | 64 | 64 | 16 | 16 | 16 |
| MDREC 1238 | 64 | 64 | 16 | 16 | 16 |
| P. aeruginosa | 16 | 128 | 64 | 128 | 64 |
| MDRPA 2002 | 16 | 128 | 64 | 128 | 64 |
| MDRPA 2003 | 32 | >128 | 64 | 128 | 64 |
| A. baumannii | 64 | 64 | 8 | 16 | 16 |
| MDRAB 12035 | 64 | 64 | 8 | 16 | 16 |
| MDRAB 12036 | 64 | 64 | 16 | 16 | 16 |
| S. typhimurium | 64 | 64 | 16 | 16 | 16 |
| MDRST 8007 | 64 | 64 | 16 | 16 | 16 |
| MDRST 8009 | 64 | 64 | 32 | 16 | 32 |
| B. subtilis | >128 | >128 | >128 | >128 | >128 |
| S. epidermidis | >128 | >128 | >128 | >128 | >128 |
| S. aureus | >128 | >128 | >128 | >128 | >128 |
| MRSA 3114 | >128 | >128 | >128 | >128 | >128 |
| MRSA 3126 | >128 | >128 | >128 | >128 | >128 |

Antibacterial Activity of PapMA-11 to PapMA-14 Peptides against Gram-Negative Bacteria, Gram-Positive Bacteria and Antibiotic-Resistant Starins Thereof Further, it was confirmed that the peptides of SEQ ID Nos. 15 to 20 had high antibacterial activity against all the gram-negative bacteria (Table 6). It was confirmed that the peptides of SEQ ID Nos. 15 to 20 exhibited significantly higher antibacterial activity against *A. baumannii* and *S. typhimurium* than the peptide of SEQ ID No. 1 (PapMA-1), and that PapMA-15, PapMA-17, PapMA-19, and PapMA-20 exhibited antibacterial activity at least twice as high as that of PaPMA-1.

Together with this, the peptides of SEQ ID Nos. 15 to 20 exhibited excellent antibacterial activity even against multi-drug resistant bacteria, so that it was confirmed that PapMA-15, PapMA-17, PapMA-19, and PapMA-20 exhibited twice to four times higher antibacterial activity than PapMA-1.

Finally, it was confirmed that the peptides of SEQ ID Nos. 21 to 24 had high antibacterial activity against all the gram-negative bacteria (Table 7). It was confirmed that the peptides of SEQ ID Nos. 21 to 24 exhibited significantly higher antibacterial activity against *A. baumannii* and *S. typhimurium* than the peptide of SEQ ID No. 1 (PapMA-1), and that PapMA-21, PapMA-22, PapMA-23, and PapMA-24 exhibited antibacterial activity at least twice as high as that of PaPMA-1.

Together with this, the peptides of SEQ ID Nos. 21 to 24 exhibited excellent antibacterial activity even against multi-drug resistant bacteria, so that it was confirmed that PapMA-21, PapMA-22, PapMA-23, and PapMA-24 exhibited twice to four times higher antibacterial activity than PapMA-1.

TABLE 6

| Target strain | Minimal inhibitory concentration MIC (µg/ml) | | | | | | |
|---|---|---|---|---|---|---|---|
| | PapMA-1 SEQ ID No. 1 | PapMA-15 SEQ ID No. 15 | PapMA-16 SEQ ID No. 16 | PapMA-17 SEQ ID No. 17 | PapMA-18 SEQ ID No. 18 | PapMA-19 SEQ ID No. 19 | PapMA-20 SEQ ID No. 20 |
| E. coli | 64 | 32 | 64 | 16 | 64 | 32 | 16 |
| MDREC 1229 | 64 | 32 | 64 | 16 | 64 | 32 | 16 |
| MDREC 1238 | 64 | 32 | 64 | 32 | 64 | 32 | 32 |
| P. aeruginosa | 16 | 32 | 64 | 16 | 32 | 64 | 64 |
| MDRPA 2002 | 16 | 32 | 64 | 16 | 32 | 64 | 64 |
| MDRPA 2003 | 32 | 32 | 64 | 16 | 64 | 64 | 64 |
| A. baumannii | 64 | 32 | 32 | 32 | 32 | 16 | 16 |
| MDRAB 12035 | 64 | 32 | 32 | 32 | 32 | 32 | 16 |
| MDRAB 12036 | 64 | 32 | 32 | 32 | 32 | 32 | 16 |
| S. typhimurium | 64 | 32 | 64 | 32 | 32 | 32 | 32 |
| MDRST 8007 | 64 | 64 | 64 | 64 | 64 | 64 | 64 |
| MDRST 8009 | 64 | 64 | 64 | 64 | 64 | 64 | 64 |
| B. subtilis | >128 | >128 | >128 | >128 | >128 | >128 | >128 |
| S. epidermidis | >128 | >128 | >128 | >128 | >128 | >128 | >128 |
| S. aureus | >128 | >128 | >128 | >128 | >128 | >128 | >128 |
| MRSA 3114 | >128 | >128 | >128 | >128 | >128 | >128 | >128 |
| MRSA 3126 | >128 | >128 | >128 | >128 | >128 | >128 | >128 |

Antibacterial Activity of PapMA-15 to PapMA-20 Peptides against Gram-Negative Bacteria, Gram-Positive Bacteria and Antibiotic-Resistant Strains Thereof

TABLE 7

| Target strain | Minimal inhibitory concentration MIC (μg/ml) | | | | |
|---|---|---|---|---|---|
| | PapMA-1 SEQ ID No. 1 | PapMA-21 SEQ ID No. 21 | PapMA-22 SEQ ID No. 22 | PapMA-23 SEQ ID No. 23 | PapMA-24 SEQ ID No. 24 |
| E. coli | 64 | 32 | 32 | 32 | 32 |
| MDREC 1229 | 64 | 32 | 32 | 32 | 32 |
| MDREC 1238 | 64 | 32 | 32 | 32 | 32 |
| P. aeruginosa | 16 | 32 | 16 | 64 | 64 |
| MDRPA 2002 | 16 | 32 | 32 | 64 | 64 |
| MDRPA 2003 | 32 | 32 | 32 | 64 | 64 |
| A. baumannii | 64 | 32 | 16 | 32 | 16 |
| MDRAB 12035 | 64 | 32 | 32 | 32 | 32 |
| MDRAB 12036 | 64 | 32 | 32 | 32 | 32 |
| S. typhimurium | 64 | 32 | 32 | 32 | 32 |
| MDRST 8007 | 64 | 64 | 32 | 64 | 32 |
| MDRST 8009 | 64 | 32 | 32 | 32 | 32 |
| B. subtilis | >128 | >128 | >128 | >128 | >128 |
| S. epidermidis | >128 | >128 | >128 | >128 | >128 |
| S. aureus | >128 | >128 | >128 | >128 | >128 |
| MRSA 3114 | >128 | >128 | >128 | >128 | >128 |
| MRSA 3126 | >128 | >128 | >128 | >128 | >128 |

Antibacterial Activity of PapMA-21 to PapMA-24 Peptides against Gram-Negative Bacteria, Gram-Positive Bacteria and Antibiotic-Resistant Strains Thereof <2-2> Identification of Antibacterial Activity of Existing Antibiotics Against Gram-Positive Bacteria and Gram-Negative Bacteria In order to compare the antibacterial activity of the antimicrobial peptide of the present invention with that of an existing antibiotic, the MIC concentration at which the antibiotics exhibited against the same gram-positive bacteria and gram-negative bacteria strains was identified.

Specifically, the MIC of the antibiotics was identified by preparing a target strain in the same manner as in Example <2-1>, and treating the target strain with erythromycin, vancomycin or linezolid.

As a result, as shown in the following [Table 8], it was confirmed that the antibiotics had low antibacterial activity against the gram-negative bacteria by exhibiting an MIC of 32 μg/ml or more as is known, whereas all the antibiotics exhibited very high antibacterial activity against gram-positive bacteria (Table 8).

TABLE 8

| Class-ification | Target strain | Minimal inhibitory concentration MIC (μg/ml) | | |
|---|---|---|---|---|
| | | Erythromycin | Vancomycin | Linezolid |
| Gram-negative bacteria | E. coli | 128 | 1024 | 256 |
| | P. aeruginosa | 256 | >1024 | >1024 |
| | A. baumannii | 32 | 1024 | 256 |
| | S. typhimurium | 64 | 512 | 256 |
| Gram-positive bacteria | B. subtilis | 0.25 | 1 | 1 |
| | S. epidermidis | 1 | 1 | 1 |
| | S. aureus | 0.25 | 1 | 1 |
| Antibiotic-resistant strains | MDREC 1229 | 256 | >1024 | 512 |
| | MDRAB 12035 | 32 | >1024 | 512 |

Antibacterial activity of existing antibiotics against gram-negative bacteria, gram-positive bacteria, and antibiotic-resistant strains thereof <Example 3> Identification of Synergistic Effect During Combined Treatment of Antimicrobial Peptide and Antibiotic <3-1> Identification of Variation in MIC of Antibiotics During Combined Treatment of Antimicrobial Peptide and Antibiotic By confirming that the antimicrobial peptide of the present invention exhibited high antibacterial activity against gram-negative bacteria, it was confirmed whether a significant synergistic activity was exhibited during the combined treatment of antibiotics which exhibit strong antibacterial activity against gram-positive bacteria only and has no significant antibacterial activity against gram-negative bacteria with the synthetic peptide of the present invention.

Specifically, the strains described in [Table 2] were prepared and diluted with an MH medium such that the number of bacteria was $2\times10^6$ colony-forming units (CFUs) per 1 ml, 100 μl of the diluted strains was each aliquoted into a 96-well microtiter plate, and then 50 μl of a peptide solution diluted with the MH medium from the MIC value (solution diluted stepwise at 2: 1) was added to each well. Thereafter, the MIC value of each mixed solution was determined by diluting the antibiotic solution with the MH medium, adding 50 μl of the diluted solution to each well, and performing an experiment even under a reversed condition. Consequently, as shown in the following [Table 9] to [Table 12], as a result of confirming whether it was possible to exhibit a synergistic effect of antibacterial activity by administering erythromycin, vancomycin, or linezolid which are existing antibiotics together with PapMA-1 to PapMA-24 which are the antimicrobial peptides of the present invention, it was confirmed that when the peptides of the present invention were treated at a 1/2 MIC value, the MICs of erythromycin against E. coli and resistant strains thereof and A. baumannii and resistant strains thereof were lowered by up to 1024 times (Tables 9 to 12).

First, it was confirmed that among the peptides of SEQ ID Nos. 2 to 4 which are derivative peptides designed by using the PapMA-1 peptide of SEQ ID No. 1 as a parent, particularly, when the PapMA-2 peptide of SEQ ID No. 2 was each added at the same peptide concentration as that of PapMA-1 to the strains, the MIC value of the antibiotics mixed with PapMA-2 was lowered by twice to four times as compared to the value of PapMA-1.

It was confirmed that for example, when the peptide was mixed at 16 μg/ml which is a 1/4 concentration of the peptide MIC with the antibiotics and *E. coli* was treated with the mixture, the MIC value of each of erythromycin and linezolid was 2 and 16 μg/ml, respectively (1/64 and 1/16 of the MIC of the antibiotic, respectively) in the case where PapMA-1 was mixed with erythromycin or linezolid. In contrast, it was confirmed that in the case where PapMA-2 was mixed with erythromycin or linezolid and *E. coli* was treated with the mixture, the MIC value of each of erythromycin and linezolid was 0.5 and 8 μg/ml, respectively, and thus the MIC of the antibiotics was reduced to 1/256 and 1/32 levels, respectively (Table 9).

Further, it was confirmed that PapMA-7 exhibited an MIC of 32 μg/ml against *E. coli*, and when PapMA-7 was mixed at 16 μg/ml which is a 1/2 concentration of the MIC with erythromycin or linezolid and *E. coli* was treated with the mixture, the MIC value of each of erythromycin and linezolid was 0.125 and 1 μg/ml, respectively, which was reduced to 1/512 and 1/256 levels of the MIC values in the case where *E. coli* was treated with each antibiotics only (Table 9). Through this, it can be seen that the PapMA-7 peptide exhibits a lower MIC concentration than the PapMA-1 peptide even when administered alone, and thus exhibits excellent antibacterial activity, and during the combined treatment with the antibiotic, the MIC values of erythromycin, vancomycin, and linezolid exhibit further reduced levels than those during the combined treatment with the PapMA-1 peptide.

When the MIC values were compared by the method as described above, it was confirmed that during the combined treatment with the existing antibiotic, the PapMA-3, PapMA-4, PapMA-5, PapMA-10, PapMA-11, PapMA-15, PapMA-21, PapMA-22, PapMA-23 and PapMA-24 peptides of the present invention exhibited a synergistic effect of antibacterial activity at a level similar to that of the PapMA-1 peptide against *E. coli* and MDREC1229 which is a multi-drug resistant strain thereof, and the PapMA-2, PapMA-6, PapMA-7, PapMA-8, PapMA-9, PapMA-12, PapMA-13, PapMA-14, PapMA-16, PapMA-17, PapMA-18, PapMA-19 and PapMA-20 peptides exhibited a synergistic effect with the existing antibiotics at a higher level than the PapMA-1 peptide (Tables 9 and 10).

TABLE 9

| Peptide treatment concentration | | *E. coli* Antibiotic MIC (μg/ml) | | |
|---|---|---|---|---|
| (μg/ml) | | Erythromycin | Vancomycin | Linezolid |
| Compound alone | | 128 | 1024 | 256 |
| PapMA-1 concentration (Conc./MIC) | 64 (1) | 0 | 0 | 0 |
| | 32 (1/2) | 0.125 | 4 | 8 |
| | 16 (1/4) | 0.5 | 16 | 16 |
| | 8 (1/8) | 2 | 32 | 16 |
| | 6 (1/11) | 4 | 32 | 16 |
| | 4 (1/16) | 16 | >128 | 64 |
| | 2 (1/32) | 32 | >128 | 128 |
| | 1 (1/64) | 64 | >128 | 128 |
| PapMA-2 concentration (Conc./MIC) | 64 (1) | 0 | 0 | 0 |
| | 32 (1/2) | 0.125 | 4 | 4 |
| | 16 (1/4) | 0.25 | 8 | 8 |
| | 8 (1/8) | 0.5 | 32 | 8 |
| | 6 (1/11) | 2 | 64 | 16 |
| | 4 (1/16) | 16 | >128 | 16 |
| | 2 (1/32) | 32 | >128 | 64 |
| | 1 (1/64) | 64 | >128 | 128 |
| PapMA-3 concentration (Conc./MIC) | 64 (2) | 0 | 0 | 0 |
| | 32 (1) | 0 | 0 | 0 |
| | 16 (1/2) | 0.125 | 8 | 2 |
| | 8 (1/4) | 1 | 32 | 16 |
| | 6 (1/5) | 4 | 128 | 32 |
| | 4 (1/8) | 16 | >128 | 32 |
| | 2 (1/16) | 32 | >128 | 64 |
| | 1 (1/32) | 64 | >128 | 128 |
| PapMA-4 concentration (Conc./MIC) | 64 (4) | 0 | 0 | 0 |
| | 32 (2) | 0 | 0 | 0 |
| | 16 (1) | 0 | 0 | 0 |
| | 8 (1/2) | 8 | 32 | 16 |
| | 6 (1/3) | 8 | 128 | 32 |
| | 4 (1/4) | 16 | >128 | 32 |
| | 2 (1/8) | 32 | >128 | 64 |
| | 1 (1/16) | 64 | >128 | 128 |
| PapMA-5 concentration (Conc./MIC) | 64 (1) | 0 | 0 | 0 |
| | 32 (1/2) | 0.5 | 2 | 2 |
| | 16 (1/4) | 0.5 | 8 | 8 |
| | 8 (1/8) | 2 | 32 | 16 |
| | 6 (1/11) | 8 | 64 | 32 |
| | 4 (1/16) | 32 | 128 | 64 |
| | 2 (1/32) | 64 | >128 | 128 |
| | 1 (1/64) | 128 | >128 | >128 |
| PapMA-6 concentration (Conc./MIC) | 64 (1) | 0 | 0 | 0 |
| | 32 (1/2) | 0.125 | 1 | 2 |
| | 16 (1/4) | 0.25 | 2 | 2 |
| | 8 (1/8) | 0.5 | 8 | 8 |
| | 6 (1/11) | 4 | 16 | 8 |
| | 4 (1/16) | 8 | 32 | 32 |
| | 2 (1/32) | 64 | >128 | >128 |
| | 1 (1/64) | 64 | >128 | >128 |
| PapMA-7 concentration (Conc./MIC) | 64 (2) | 0 | 0 | 0 |
| | 32 (1) | 0 | 0 | 0 |
| | 16 (1/2) | 0.125 | 1 | 1 |
| | 8 (1/4) | 0.25 | 4 | 4 |
| | 6 (1/5) | 2 | 8 | 4 |
| | 4 (1/8) | 4 | 32 | 8 |
| | 2 (1/16) | 32 | 128 | 128 |
| | 1 (1/32) | 64 | >128 | >128 |
| PapMA-8 concentration (Conc./MIC) | 64 (2) | 0 | 0 | 0 |
| | 32 (1) | 0 | 0 | 0 |
| | 16 (1/2) | 0.25 | 2 | 2 |
| | 8 (1/4) | 0.5 | 16 | 8 |
| | 6 (1/5) | 4 | 32 | 32 |
| | 4 (1/8) | 8 | 64 | 128 |
| | 2 (1/16) | 64 | >128 | >128 |
| | 1 (1/32) | 128 | >128 | >128 |
| PapMA-9 concentration (Conc./MIC) | 64 (2) | 0 | 0 | 0 |
| | 32 (1) | 0 | 0 | 0 |
| | 16 (1/2) | 0.125 | 2 | 2 |
| | 8 (1/4) | 0.5 | 8 | 4 |
| | 6 (1/5) | 2 | 16 | 8 |
| | 4 (1/8) | 8 | 64 | 16 |
| | 2 (1/16) | 64 | >128 | >128 |
| | 1 (1/32) | 128 | >128 | >128 |
| PapMA-10 concentration (Conc./MIC) | 64 (2) | 0 | 0 | 0 |
| | 32 (1) | 0 | 0 | 0 |
| | 16 (1/2) | 0.25 | 2 | 4 |
| | 8 (1/4) | 0.5 | 16 | 8 |
| | 6 (1/5) | 8 | 32 | 64 |
| | 4 (1/8) | 32 | 64 | 128 |
| | 2 (1/16) | 64 | >128 | >128 |
| | 1 (1/32) | 128 | >128 | >128 |
| PapMA-11 concentration (Conc./MIC) | 64 (1) | 0 | 0 | 0 |
| | 32 (1/2) | 0.125 | 4 | 8 |
| | 16 (1/4) | 0.25 | 8 | 16 |
| | 8 (1/8) | 1 | 16 | 32 |
| | 6 (1/11) | 4 | 32 | 32 |
| | 4 (1/16) | 16 | >128 | 128 |
| | 2 (1/32) | 64 | >128 | 128 |
| | 1 (1/64) | 64 | >128 | >128 |

TABLE 9-continued

E. coli

| Peptide treatment concentration (µg/ml) | | Antibiotic MIC (µg/ml) | | |
|---|---|---|---|---|
| | | Erythromycin | Vancomycin | Linezolid |
| PapMA-12 concentration (Conc./MIC) | 64 (8) | 0 | 0 | 0 |
| | 32 (4) | 0 | 0 | 0 |
| | 16 (2) | 0 | 0 | 0 |
| | 8 (1) | 0 | 0 | 0 |
| | 6 (3/4) | 1 | 8 | 2 |
| | 4 (1/2) | 2 | 16 | 8 |
| | 2 (1/4) | 32 | 128 | 128 |
| | 1 (1/8) | 64 | >128 | >128 |
| PapMA-13 concentration (Conc./MIC) | 64 (4) | 0 | 0 | 0 |
| | 32 (2) | 0 | 0 | 0 |
| | 16 (1) | 0 | 0 | 0 |
| | 8 (1/2) | 0.25 | 2 | 1 |
| | 6 (1/3) | 1 | 8 | 4 |
| | 4 (1/4) | 2 | 16 | 8 |
| | 2 (1/8) | 16 | 64 | 64 |
| | 1 (1/16) | 64 | >128 | >128 |
| PapMA-14 concentration (Conc./MIC) | 64 (8) | 0 | 0 | 0 |
| | 32 (4) | 0 | 0 | 0 |
| | 16 (2) | 0 | 0 | 0 |
| | 8 (1) | 0 | 0 | 0 |
| | 6 (3/4) | 1 | 8 | 2 |
| | 4 (1/2) | 2 | 16 | 8 |
| | 2 (1/4) | 32 | 128 | 128 |
| | 1 (1/8) | 128 | >128 | >128 |
| PapMA-15 concentration (Conc./MIC) | 64 (2) | 0 | 0 | 0 |
| | 32 (1) | 0 | 0 | 0 |
| | 16 (1/2) | 0.25 | 16 | 8 |
| | 8 (1/4) | 1 | 32 | 16 |
| | 6 (1/5) | 2 | 64 | 16 |
| | 4 (1/8) | 16 | >128 | 32 |
| | 2 (1/16) | 32 | >128 | 128 |
| | 1 (1/32) | 64 | >128 | >128 |
| PapMA-16 concentration (Conc./MIC) | 64 (1) | 0 | 0 | 0 |
| | 32 (1/2) | 0.125 | 4 | 4 |
| | 16 (1/4) | 0.25 | 8 | 8 |
| | 8 (1/8) | 2 | 16 | 16 |
| | 6 (1/11) | 2 | 32 | 16 |
| | 4 (1/16) | 16 | >128 | 32 |
| | 2 (1/32) | 32 | >128 | >128 |
| | 1 (1/64) | 128 | >128 | >128 |
| PapMA-17 concentration (Conc./MIC) | 64 (4) | 0 | 0 | 0 |
| | 32 (2) | 0 | 0 | 0 |
| | 16 (1) | 0 | 0 | 0 |
| | 8 (1/2) | 1 | 16 | 8 |
| | 6 (1/3) | 2 | 32 | 16 |
| | 4 (1/4) | 8 | 128 | 32 |
| | 2 (1/8) | 16 | >128 | >128 |
| | 1 (1/16) | 128 | >128 | >128 |
| PapMA-18 concentration (Conc./MIC) | 64 (1) | 0 | 0 | 0 |
| | 32 (1/2) | 0.125 | 4 | 4 |
| | 16 (1/4) | 0.25 | 8 | 8 |
| | 8 (1/8) | 1 | 16 | 8 |
| | 6 (1/11) | 1 | 32 | 16 |
| | 4 (1/16) | 8 | >128 | 64 |
| | 2 (1/32) | 32 | >128 | >128 |
| | 1 (1/64) | 128 | >128 | >128 |
| PapMA-19 concentration (Conc./MIC) | 64 (2) | 0 | 0 | 0 |
| | 32 (1) | 0 | 0 | 0 |
| | 16 (1/2) | 0.25 | 4 | 4 |
| | 8 (1/4) | 1 | 8 | 8 |
| | 6 (1/5) | 2 | 8 | 8 |
| | 4 (1/8) | 8 | 64 | 32 |
| | 2 (1/16) | 32 | 128 | 64 |
| | 1 (1/32) | 64 | >128 | >128 |
| PapMA-20 concentration (Conc./MIC) | 64 (4) | 0 | 0 | 0 |
| | 32 (2) | 0 | 0 | 0 |
| | 16 (1) | 0 | 0 | 0 |
| | 8 (1/2) | 0.5 | 8 | 4 |
| | 6 (1/3) | 1 | 16 | 8 |
| | 4 (1/4) | 8 | 64 | 16 |
| | 2 (1/8) | 32 | >128 | 64 |
| | 1 (1/16) | 64 | >128 | >128 |
| PapMA-21 concentration (Conc./MIC) | 64 (2) | 0 | 0 | 0 |
| | 32 (1) | 0 | 0 | 0 |
| | 16 (1/2) | 0.25 | 8 | 8 |
| | 8 (1/4) | 1 | 32 | 16 |
| | 6 (1/5) | 2 | 64 | 32 |
| | 4 (1/8) | 8 | >128 | 64 |
| | 2 (1/16) | 32 | >128 | 128 |
| | 1 (1/32) | 64 | >128 | >128 |
| PapMA-22 concentration (Conc./MIC) | 64 (2) | 0 | 0 | 0 |
| | 32 (1) | 0 | 0 | 0 |
| | 16 (1/2) | 1 | 16 | 16 |
| | 8 (1/4) | 2 | 32 | 32 |
| | 6 (1/5) | 8 | 64 | 32 |
| | 4 (1/8) | 16 | 128 | 64 |
| | 2 (1/16) | 32 | >128 | 128 |
| | 1 (1/32) | 128 | >128 | >128 |
| PapMA-23 concentration (Conc./MIC) | 64 (2) | 0 | 0 | 0 |
| | 32 (1) | 0 | 0 | 0 |
| | 16 (1/2) | 0.5 | 8 | 16 |
| | 8 (1/4) | 2 | 16 | 16 |
| | 6 (1/5) | 4 | 64 | 32 |
| | 4 (1/8) | 16 | >128 | 64 |
| | 2 (1/16) | 64 | >128 | 128 |
| | 1 (1/32) | 128 | >128 | >128 |
| PapMA-24 concentration (Conc./MIC) | 64 (2) | 0 | 0 | 0 |
| | 32 (1) | 0 | 0 | 0 |
| | 16 (1/2) | 0.5 | 8 | 8 |
| | 8 (1/4) | 2 | 16 | 32 |
| | 6 (1/5) | 4 | 32 | 32 |
| | 4 (1/8) | 16 | 128 | 64 |
| | 2 (1/16) | 32 | >128 | 128 |
| | 1 (1/32) | 64 | >128 | >128 |

Antibacterial activity of antibiotic against *E. coli* during treatment with PapMA-1 to PapMA-24 antimicrobial peptides

TABLE 10

MDREC 1229

| Peptide treatment concentration (µg/ml) | | Antibiotic MIC (µg/ml) | | |
|---|---|---|---|---|
| | | Erythromycin | Vancomycin | Linezolid |
| Compound alone | | 256 | >1024 | 512 |
| PapMA-1 concentration (Conc./MIC) | 64 (1) | 0 | 0 | 0 |
| | 32 (1/2) | 0.25 | 8 | 8 |
| | 16 (1/4) | 1 | 16 | 16 |
| | 8 (1/8) | 4 | 128 | 32 |
| | 6 (1/11) | 8 | >128 | 64 |
| | 4 (1/16) | 16 | >128 | 64 |
| | 2 (1/32) | 32 | >128 | 128 |
| | 1 (1/64) | 128 | >128 | >128 |
| PapMA-2 concentration (Conc./MIC) | 64 (1) | 0 | 0 | 0 |
| | 32 (1/2) | 0.125 | 8 | 4 |
| | 16 (1/4) | 0.5 | 16 | 8 |
| | 8 (1/8) | 2 | 64 | 16 |
| | 6 (1/11) | 8 | 128 | 32 |
| | 4 (1/16) | 16 | 128 | 32 |
| | 2 (1/32) | 32 | >128 | 64 |
| | 1 (1/64) | 64 | >128 | >128 |
| PapMA-3 concentration (Conc./MIC) | 64 (2) | 0 | 0 | 0 |
| | 32 (1) | 0 | 0 | 0 |
| | 16 (1/2) | 0.25 | 16 | 4 |
| | 8 (1/4) | 4 | 128 | 16 |
| | 6 (1/5) | 16 | >128 | 32 |
| | 4 (1/8) | 32 | >128 | 64 |
| | 2 (1/16) | 32 | >128 | 64 |
| | 1 (1/32) | 128 | >128 | >128 |

TABLE 10-continued

MDREC 1229

| Peptide treatment concentration (µg/ml) | | Antibiotic MIC (µg/ml) | | |
| --- | --- | --- | --- | --- |
| | | Erythromycin | Vancomycin | Linezolid |
| PapMA-4 concentration (Conc./MIC) | 64 (2) | 0 | 0 | 0 |
| | 32 (1) | 0 | 0 | 0 |
| | 16 (1/2) | 0.25 | 32 | 4 |
| | 8 (1/4) | 4 | 128 | 16 |
| | 6 (1/5) | 16 | >128 | 64 |
| | 4 (1/8) | 16 | >128 | 64 |
| | 2 (1/16) | 32 | >128 | 64 |
| | 1 (1/32) | 64 | >128 | >128 |
| PapMA-5 concentration (Conc./MIC) | 64 (1) | 0 | 0 | 0 |
| | 32 (1/2) | 0.25 | 8 | 4 |
| | 16 (1/4) | 1 | 16 | 16 |
| | 8 (1/8) | 4 | 64 | 32 |
| | 6 (1/11) | 8 | >128 | 32 |
| | 4 (1/16) | 16 | >128 | 64 |
| | 2 (1/32) | 64 | >128 | 128 |
| | 1 (1/64) | 128 | >128 | 128 |
| PapMA-6 concentration (Conc./MIC) | 64 (1) | 0 | 0 | 0 |
| | 32 (1/2) | 0.125 | 2 | 1 |
| | 16 (1/4) | 0.25 | 4 | 4 |
| | 8 (1/8) | 1 | 16 | 8 |
| | 6 (1/11) | 2 | 64 | 8 |
| | 4 (1/16) | 8 | >128 | 32 |
| | 2 (1/32) | 32 | >128 | 64 |
| | 1 (1/64) | 64 | >128 | 128 |
| PapMA-7 concentration (Conc./MIC) | 64 (1) | 0 | 0 | 0 |
| | 32 (1/2) | 0.0625 | 1 | 1 |
| | 16 (1/4) | 0.125 | 2 | 2 |
| | 8 (1/8) | 1 | 8 | 4 |
| | 6 (1/11) | 2 | 16 | 8 |
| | 4 (1/16) | 4 | 128 | 16 |
| | 2 (1/32) | 16 | >128 | 32 |
| | 1 (1/64) | 64 | >128 | 128 |
| PapMA-8 concentration (Conc./MIC) | 64 (1) | 0 | 0 | 0 |
| | 32 (1/2) | 0.125 | 8 | 8 |
| | 16 (1/4) | 0.5 | 16 | 16 |
| | 8 (1/8) | 1 | 32 | 32 |
| | 6 (1/11) | 4 | >128 | 32 |
| | 4 (1/16) | 8 | >128 | 128 |
| | 2 (1/32) | 64 | >128 | >128 |
| | 1 (1/64) | >128 | >128 | >128 |
| PapMA-9 concentration (Conc./MIC) | 64 (1) | 0 | 0 | 0 |
| | 32 (1/2) | 0.125 | 2 | 2 |
| | 16 (1/4) | 0.5 | 4 | 4 |
| | 8 (1/8) | 1 | 8 | 8 |
| | 6 (1/11) | 2 | 32 | 16 |
| | 4 (1/16) | 8 | 128 | 32 |
| | 2 (1/32) | 64 | >128 | 64 |
| | 1 (1/64) | 64 | >128 | 128 |
| PapMA-10 concentration (Conc./MIC) | 64 (1) | 0 | 0 | 0 |
| | 32 (1/2) | 0.25 | 16 | 8 |
| | 16 (1/4) | 1 | 32 | 16 |
| | 8 (1/8) | 2 | 128 | 64 |
| | 6 (1/11) | 8 | >128 | 64 |
| | 4 (1/16) | 16 | >128 | 128 |
| | 2 (1/32) | 64 | >128 | >128 |
| | 1 (1/64) | >128 | >128 | >128 |
| PapMA-11 concentration (Conc./MIC) | 64 (1) | 0 | 0 | 0 |
| | 32 (1/2) | 0.5 | 8 | 8 |
| | 16 (1/4) | 1 | 16 | 16 |
| | 8 (1/8) | 4 | 128 | 32 |
| | 6 (1/11) | 8 | >128 | 128 |
| | 4 (1/16) | 16 | >128 | 128 |
| | 2 (1/32) | 64 | >128 | >128 |
| | 1 (1/64) | 128 | >128 | >128 |
| PapMA-12 concentration (Conc./MIC) | 64 (4) | 0 | 0 | 0 |
| | 32 (2) | 0 | 0 | 0 |
| | 16 (1) | 0 | 0 | 0 |
| | 8 (1/2) | 1 | 8 | 16 |
| | 6 (1/3) | 4 | 32 | 16 |
| | 4 (1/4) | 8 | 128 | 32 |
| | 2 (1/8) | 32 | >128 | 128 |
| | 1 (1/16) | 128 | >128 | >128 |
| PapMA-13 concentration (Conc./MIC) | 64 (4) | 0 | 0 | 0 |
| | 32 (2) | 0 | 0 | 0 |
| | 16 (1) | 0 | 0 | 0 |
| | 8 (1/2) | 0.5 | 4 | 4 |
| | 6 (1/3) | 4 | 16 | 8 |
| | 4 (1/4) | 8 | 64 | 64 |
| | 2 (1/8) | 32 | >128 | 128 |
| | 1 (1/16) | >128 | >128 | >128 |
| PapMA-14 concentration (Conc./MIC) | 64 (4) | 0 | 0 | 0 |
| | 32 (2) | 0 | 0 | 0 |
| | 16 (1) | 0 | 0 | 0 |
| | 8 (1/2) | 1 | 8 | 16 |
| | 6 (1/3) | 4 | 32 | 16 |
| | 4 (1/4) | 8 | 128 | 32 |
| | 2 (1/8) | 32 | >128 | 128 |
| | 1 (1/16) | 128 | >128 | >128 |
| PapMA-15 concentration (Conc./MIC) | 64 (2) | 0 | 0 | 0 |
| | 32 (1) | 0 | 0 | 0 |
| | 16 (1/2) | 1 | 16 | 16 |
| | 8 (1/4) | 4 | 32 | 32 |
| | 6 (1/5) | 8 | 64 | 64 |
| | 4 (1/8) | 16 | >128 | 64 |
| | 2 (1/16) | 32 | >128 | 128 |
| | 1 (1/32) | >128 | >128 | >128 |
| PapMA-16 concentration (Conc./MIC) | 64 (1) | 0 | 0 | 0 |
| | 32 (1/2) | 0.5 | 4 | 4 |
| | 16 (1/4) | 1 | 8 | 8 |
| | 8 (1/8) | 2 | 16 | 16 |
| | 6 (1/11) | 4 | 32 | 32 |
| | 4 (1/16) | 32 | 128 | 64 |
| | 2 (1/32) | 64 | >128 | >128 |
| | 1 (1/64) | >128 | >128 | >128 |
| PapMA-17 concentration (Conc./MIC) | 64 (4) | 0 | 0 | 0 |
| | 32 (2) | 0 | 0 | 0 |
| | 16 (1) | 0 | 0 | 0 |
| | 8 (1/2) | 4 | 16 | 16 |
| | 6 (1/3) | 8 | 32 | 16 |
| | 4 (1/4) | 16 | 64 | 64 |
| | 2 (1/8) | 32 | >128 | >128 |
| | 1 (1/16) | >128 | >128 | >128 |
| PapMA-18 concentration (Conc./MIC) | 64 (1) | 0 | 0 | 0 |
| | 32 (1/2) | 0.5 | 4 | 4 |
| | 16 (1/4) | 1 | 8 | 8 |
| | 8 (1/8) | 2 | 16 | 16 |
| | 6 (1/11) | 4 | 32 | 32 |
| | 4 (1/16) | 16 | >128 | 64 |
| | 2 (1/32) | 32 | >128 | 128 |
| | 1 (1/64) | >128 | >128 | >128 |
| PapMA-19 concentration (Conc./MIC) | 64 (2) | 0 | 0 | 0 |
| | 32 (1) | 0 | 0 | 0 |
| | 16 (1/2) | 0.5 | 4 | 4 |
| | 8 (1/4) | 1 | 8 | 16 |
| | 6 (1/5) | 2 | 8 | 16 |
| | 4 (1/8) | 8 | 64 | 32 |
| | 2 (1/16) | 32 | 128 | 128 |
| | 1 (1/32) | 128 | >128 | >128 |
| PapMA-20 concentration (Conc./MIC) | 64 (4) | 0 | 0 | 0 |
| | 32 (2) | 0 | 0 | 0 |
| | 16 (1) | 0 | 0 | 0 |
| | 8 (1/2) | 1 | 8 | 8 |
| | 6 (1/3) | 2 | 16 | 16 |
| | 4 (1/4) | 8 | 64 | 16 |
| | 2 (1/8) | 32 | >128 | 64 |
| | 1 (1/16) | 128 | >128 | >128 |
| PapMA-21 concentration (Conc./MIC) | 64 (2) | 0 | 0 | 0 |
| | 32 (1) | 0 | 0 | 0 |
| | 16 (1/2) | 2 | 16 | 16 |
| | 8 (1/4) | 4 | 128 | 32 |
| | 6 (1/5) | 8 | >128 | 64 |
| | 4 (1/8) | 32 | >128 | 128 |
| | 2 (1/16) | 64 | >128 | >128 |
| | 1 (1/32) | 128 | >128 | >128 |

TABLE 10-continued

MDREC 1229

| Peptide treatment concentration (μg/ml) | | Antibiotic MIC (μg/ml) | | |
|---|---|---|---|---|
| | | Erythromycin | Vancomycin | Linezolid |
| PapMA-22 concentration (Conc./MIC) | 64 (2) | 0 | 0 | 0 |
| | 32 (1) | 0 | 0 | 0 |
| | 16 (1/2) | 2 | 32 | 16 |
| | 8 (1/4) | 4 | 64 | 32 |
| | 6 (1/5) | 16 | >128 | 64 |
| | 4 (1/8) | 32 | >128 | 128 |
| | 2 (1/16) | 32 | >128 | >128 |
| | 1 (1/32) | 128 | >128 | >128 |
| PapMA-23 concentration (Conc./MIC) | 64 (2) | 0 | 0 | 0 |
| | 32 (1) | 0 | 0 | 0 |
| | 16 (1/2) | 1 | 16 | 16 |
| | 8 (1/4) | 4 | 32 | 32 |
| | 6 (1/5) | 8 | 128 | 32 |
| | 4 (1/8) | 32 | >128 | 64 |
| | 2 (1/16) | 64 | >128 | 128 |
| | 1 (1/32) | 128 | >128 | >128 |
| PapMA-24 concentration (Conc./MIC) | 64 (2) | 0 | 0 | 0 |
| | 32 (1) | 0 | 0 | 0 |
| | 16 (1/2) | 1 | 16 | 8 |
| | 8 (1/4) | 2 | 32 | 32 |
| | 6 (1/5) | 8 | 64 | 64 |
| | 4 (1/8) | 32 | >128 | 64 |
| | 2 (1/16) | 64 | >128 | 128 |
| | 1 (1/32) | 128 | >128 | >128 |

Antibacterial activity of antibiotic against MDREC 1229 during treatment with PapMA-1 to PapMA-24 antimicrobial peptides Further, as shown in the following [Table 11] and [Table 12], it was confirmed that PapMA-7 also exhibited a synergistic effect at an increased level against *A. baumannii*. Since PapMA-1 exhibits an MIC of 64 μg/ml against *A. baumannii*, it was confirmed that when PapMA-1 at 8 μg/ml which is a 1/4 concentration of 64 μg/ml was administered in combination with erythromycin, erythromycin had an MIC of 0.5 μg/ml, and thus exhibited an MIC at a 1/64 level lower than during the treatment with erythromycin only, and it was confirmed that when PapMA-1 at 8 μg/ml was administered in combination with linezolid, an MIC exhibited a 1/32 level than when linezolid was administered alone (Table 11). In addition, since PapMA-2 exhibits an MIC of 16 μg/ml against *A. baumannii*, it was confirmed that when PapMA-2 at 8 μg/ml which is a 1/2 concentration of 16 μg/ml was administered in combination with erythromycin, erythromycin had an MIC of 0.125 μg/ml, and thus exhibited an MIC at a 1/256 level lower than during the treatment with erythromycin only, and it was confirmed that when PapMA-1 at 8 μg/ml was administered in combination with linezolid, an MIC was 8, exhibiting a 1/32 level than when linezolid was administered alone (Table 11).

In comparison with this, it was confirmed that when PapMA-7 was subjected to combined treatment with erythromycin through treatment at 8 μg/ml which is the same concentration as PapMA-1 or PapMA-2, the MIC value of erythromycin was reduced to 0.125 μg/ml, and thus was reduced to a 1/256 level lower than the MIC during the single administration (Table 11). Further, when linezolid was administered, the MIC value of linezolid was 1 and exhibited a 1/256 level. For the same aspect as in erythromycin, when the PapMa-7 peptide at 8 μg/ml was also added to vancomycin, the MIC of vancomycin subjected to combined treatment with the PapMA-7 peptide was reduced to 2 μg/ml (1/512). That is, through this, it was confirmed that when the PapMA-7 peptide was treated at the same concentration as that of PapMA-1 or PapMA-2 which is a template peptide, a synergistic effect by the combined treatment with existing antibiotics was significantly increased.

In the same manner, a change in MIC concentration of the antibiotic against *A. baumannii* and MDRAB 12035 which is a multi-drug resistant strain thereof was identified according to the treatment of the antimicrobial peptides PapMA-1 to PapMA-24 in mixture with the antibiotic, and the same aspect as in *E. coli* was exhibited, so that it was confirmed that the PapMA-5, PapMA-10, PapMA-11, PapMA-16, PapMA-17, PapMA-22, PapMA-23 and PapMA-24 peptides of the present invention exhibited a synergistic effect of antibacterial activity at a level similar to that of PapMA-1 peptide during the combined treatment with the existing antibiotic. In addition, it was confirmed that the PapMA-2, PapMA-3, PapMA-6, PapMA-7, PapMA-8, PapMA-9, PapMA-12, PapMA-13, PapMA-14, PapMA-19 and PapMA-20 peptides exhibited a synergistic effect with existing antibiotics at a higher level than the PapMA-1 peptide (Tables 11 and 12).

TABLE 11

*A. baumannii*

| Peptide treatment concentration (μg/ml) | | Antibiotic MIC (μg/ml) | | |
|---|---|---|---|---|
| | | Erythromycin | Vancomycin | Linezolid |
| Compound Alone | | 32 | 1024 | 256 |
| PapMA-1 Concentration (Conc./MIC) | 64 (1) | 0 | 0 | 0 |
| | 32 (1/2) | 0.0625 | 2 | 4 |
| | 16 (1/4) | 0.125 | 8 | 4 |
| | 8 (1/8) | 0.5 | 8 | 8 |
| | 6 (1/11) | 2 | 16 | 32 |
| | 4 (1/16) | 8 | 32 | 32 |
| | 2 (1/32) | 16 | 128 | 128 |
| | 1 (1/64) | 32 | >128 | >128 |
| PapMA-2 Concentration (Conc./MIC) | 64 (4) | 0 | 0 | 0 |
| | 32 (2) | 0 | 0 | 0 |
| | 16 (1) | 0 | 0 | 0 |
| | 8 (1/2) | 0.125 | 8 | 8 |
| | 6 (1/3) | 1 | 16 | 16 |
| | 4 (1/4) | 8 | 32 | 32 |
| | 2 (1/8) | 16 | 128 | 64 |
| | 1 (1/16) | 16 | >128 | >128 |
| PapMA-3 Concentration (Conc./MIC) | 64 (4) | 0 | 0 | 0 |
| | 32 (2) | 0 | 0 | 0 |
| | 16 (1) | 0 | 0 | 0 |
| | 8 (1/2) | 0.125 | 32 | 8 |
| | 6 (1/3) | 1 | 32 | 16 |
| | 4 (1/4) | 8 | 64 | 32 |
| | 2 (1/8) | 16 | 128 | 64 |
| | 1 (1/16) | 32 | >128 | >128 |
| PapMA-4 Concentration (Conc./MIC) | 64 (4) | 0 | 0 | 0 |
| | 32 (2) | 0 | 0 | 0 |
| | 16 (1) | 0 | 0 | 0 |
| | 8 (1/2) | 4 | 32 | 16 |
| | 6 (1/3) | 4 | 64 | 32 |
| | 4 (1/4) | 8 | 64 | 64 |
| | 2 (1/8) | 16 | 128 | 64 |
| | 1 (1/16) | 32 | >128 | >128 |
| PapMA-5 Concentration (Conc./MIC) | 64 (1) | 0 | 0 | 0 |
| | 32 (1/2) | 0.125 | 2 | 2 |
| | 16 (1/4) | 0.25 | 4 | 4 |
| | 8 (1/8) | 0.5 | 8 | 4 |
| | 6 (1/11) | 4 | 16 | 8 |
| | 4 (1/16) | 8 | 32 | 16 |
| | 2 (1/32) | 16 | >128 | 64 |
| | 1 (1/64) | 32 | >128 | 128 |
| PapMA-6 Concentration (Conc./MIC) | 64 (2) | 0 | 0 | 0 |
| | 32 (1) | 0 | 0 | 0 |
| | 16 (1/2) | 0.0625 | 2 | 0.5 |
| | 8 (1/4) | 0.125 | 4 | 2 |
| | 6 (1/5) | 2 | 8 | 4 |
| | 4 (1/8) | 4 | 16 | 8 |
| | 2 (1/16) | 8 | 128 | 64 |
| | 1 (1/32) | 16 | >128 | 128 |

TABLE 11-continued

*A. baumannii*

| Peptide treatment concentration (μg/ml) | | Antibiotic MIC (μg/ml) | | |
|---|---|---|---|---|
| | | Erythromycin | Vancomycin | Linezolid |
| PapMA-7 Concentration (Conc./MIC) | 64 (4) | 0 | 0 | 0 |
| | 32 (2) | 0 | 0 | 0 |
| | 16 (1) | 0 | 0 | 0 |
| | 8 (1/2) | 0.125 | 2 | 1 |
| | 6 (1/3) | 1 | 4 | 2 |
| | 4 (1/4) | 2 | 16 | 8 |
| | 2 (1/8) | 8 | 64 | 32 |
| | 1 (1/16) | 16 | >128 | 128 |
| PapMA-8 Concentration (Conc./MIC) | 64 (2) | 0 | 0 | 0 |
| | 32 (1) | 0 | 0 | 0 |
| | 16 (1/2) | 0.125 | 4 | 1 |
| | 8 (1/4) | 0.25 | 8 | 4 |
| | 6 (1/5) | 4 | 16 | 16 |
| | 4 (1/8) | 4 | 32 | 32 |
| | 2 (1/16) | 8 | >128 | 64 |
| | 1 (1/32) | 32 | >128 | >128 |
| PapMA-9 Concentration (Conc./MIC) | 64 (2) | 0 | 0 | 0 |
| | 32 (1) | 0 | 0 | 0 |
| | 16 (1/2) | 0.125 | 2 | 0.5 |
| | 8 (1/4) | 0.25 | 8 | 2 |
| | 6 (1/5) | 2 | 16 | 8 |
| | 4 (1/8) | 4 | 32 | 8 |
| | 2 (1/16) | 8 | 128 | 128 |
| | 1 (1/32) | 32 | >128 | >128 |
| PapMA-10 Concentration (Conc./MIC) | 64 (4) | 0 | 0 | 0 |
| | 32 (2) | 0 | 0 | 0 |
| | 16 (1) | 0 | 0 | 0 |
| | 8 (1/2) | 0.5 | 4 | 8 |
| | 6 (1/3) | 2 | 16 | 32 |
| | 4 (1/4) | 8 | 16 | 64 |
| | 2 (1/8) | 16 | 64 | 128 |
| | 1 (1/16) | 32 | >128 | >128 |
| PapMA-11 Concentration (Conc./MIC) | 64 (1) | 0 | 0 | 0 |
| | 32 (1/2) | 0.125 | 1 | 2 |
| | 16 (1/4) | 0.25 | 4 | 8 |
| | 8 (1/8) | 0.5 | 8 | 16 |
| | 6 (1/11) | 1 | 16 | 32 |
| | 4 (1/16) | 4 | 32 | 64 |
| | 2 (1/32) | 16 | 128 | 128 |
| | 1 (1/64) | 32 | >128 | 128 |
| PapMA-12 Concentration (Conc./MIC) | 64 (8) | 0 | 0 | 0 |
| | 32 (4) | 0 | 0 | 0 |
| | 16 (2) | 0 | 0 | 0 |
| | 8 (1) | 0 | 0 | 0 |
| | 6 (3/4) | 0.25 | 2 | 1 |
| | 4 (1/2) | 1 | 8 | 4 |
| | 2 (1/4) | 8 | 64 | 32 |
| | 1 (1/8) | 16 | >128 | 128 |
| PapMA-13 Concentration (Conc./MIC) | 64 (4) | 0 | 0 | 0 |
| | 32 (2) | 0 | 0 | 0 |
| | 16 (1) | 0 | 0 | 0 |
| | 8 (1/2) | 0.125 | 0.5 | 1 |
| | 6 (1/3) | 0.5 | 1 | 2 |
| | 4 (1/4) | 1 | 4 | 4 |
| | 2 (1/8) | 8 | 64 | 32 |
| | 1 (1/16) | 16 | 128 | 64 |
| PapMA-14 Concentration (Conc./MIC) | 64 (4) | 0 | 0 | 0 |
| | 32 (2) | 0 | 0 | 0 |
| | 16 (1) | 0 | 0 | 0 |
| | 8 (1/2) | 0.25 | 1 | 0.5 |
| | 6 (1/3) | 0.5 | 2 | 1 |
| | 4 (1/4) | 2 | 8 | 8 |
| | 2 (1/8) | 8 | 64 | 32 |
| | 1 (1/16) | 16 | >128 | 128 |
| PapMA-15 Concentration (Conc./MIC) | 64 (2) | 0 | 0 | 0 |
| | 32 (1) | 0 | 0 | 0 |
| | 16 (1/2) | 0.25 | 8 | 2 |
| | 8 (1/4) | 0.5 | 16 | 16 |
| | 6 (1/5) | 2 | 16 | 32 |
| | 4 (1/8) | 16 | 32 | 64 |
| | 2 (1/16) | 32 | 128 | 128 |
| | 1 (1/32) | 32 | >128 | >128 |
| PapMA-16 Concentration (Conc./MIC) | 64 (2) | 0 | 0 | 0 |
| | 32 (1) | 0 | 0 | 0 |
| | 16 (1/2) | 0.25 | 8 | 8 |
| | 8 (1/4) | 0.5 | 16 | 16 |
| | 6 (1/5) | 1 | 32 | 32 |
| | 4 (1/8) | 8 | 64 | 128 |
| | 2 (1/16) | 16 | 128 | >128 |
| | 1 (1/32) | 32 | >128 | >128 |
| PapMA-17 Concentration (Conc./MIC) | 64 (2) | 0 | 0 | 0 |
| | 32 (1) | 0 | 0 | 0 |
| | 16 (1/2) | 0.125 | 4 | 2 |
| | 8 (1/4) | 0.25 | 16 | 8 |
| | 6 (1/5) | 2 | 32 | 32 |
| | 4 (1/8) | 8 | 64 | 32 |
| | 2 (1/16) | 16 | >128 | 64 |
| | 1 (1/32) | 32 | >128 | >128 |
| PapMA-18 Concentration (Conc./MIC) | 64 (2) | 0 | 0 | 0 |
| | 32 (1) | 0 | 0 | 0 |
| | 16 (1/2) | 0.5 | 16 | 4 |
| | 8 (1/4) | 1 | 16 | 16 |
| | 6 (1/5) | 2 | 32 | 32 |
| | 4 (1/8) | 16 | 128 | 64 |
| | 2 (1/16) | 32 | >128 | 128 |
| | 1 (1/32) | 32 | >128 | >128 |
| PapMA-19 Concentration (Conc./MIC) | 64 (4) | 0 | 0 | 0 |
| | 32 (2) | 0 | 0 | 0 |
| | 16 (1) | 0 | 0 | 0 |
| | 8 (1/2) | 0.25 | 4 | 4 |
| | 6 (1/3) | 2 | 8 | 8 |
| | 4 (1/4) | 4 | 32 | 16 |
| | 2 (1/8) | 16 | 128 | 64 |
| | 1 (1/16) | 32 | >128 | >128 |
| PapMA-20 Concentration (Conc./MIC) | 64 (4) | 0 | 0 | 0 |
| | 32 (2) | 0 | 0 | 0 |
| | 16 (1) | 0 | 0 | 0 |
| | 8 (1/2) | 0.125 | 2 | 2 |
| | 6 (1/3) | 1 | 8 | 8 |
| | 4 (1/4) | 2 | 32 | 16 |
| | 2 (1/8) | 16 | >128 | 64 |
| | 1 (1/16) | 32 | >128 | >128 |
| PapMA-21 Concentration (Conc./MIC) | 64 (2) | 0 | 0 | 0 |
| | 32 (1) | 0 | 0 | 0 |
| | 16 (1/2) | 0.25 | 8 | 2 |
| | 8 (1/4) | 1 | 16 | 16 |
| | 6 (1/5) | 2 | 32 | 16 |
| | 4 (1/8) | 8 | 64 | 32 |
| | 2 (1/16) | 32 | >128 | >128 |
| | 1 (1/32) | 32 | >128 | >128 |
| PapMA-22 Concentration (Conc./MIC) | 64 (4) | 0 | 0 | 0 |
| | 32 (2) | 0 | 0 | 0 |
| | 16 (1) | 0 | 0 | 0 |
| | 8 (1/2) | 1 | 8 | 8 |
| | 6 (1/3) | 2 | 32 | 16 |
| | 4 (1/4) | 8 | 64 | 32 |
| | 2 (1/8) | 32 | 128 | >128 |
| | 1 (1/16) | 32 | >128 | >128 |
| PapMA-23 Concentration (Conc./MIC) | 64 (2) | 0 | 0 | 0 |
| | 32 (1) | 0 | 0 | 0 |
| | 16 (1/2) | 0.25 | 4 | 2 |
| | 8 (1/4) | 0.5 | 8 | 4 |
| | 6 (1/5) | 4 | 32 | 16 |
| | 4 (1/8) | 8 | 64 | 64 |
| | 2 (1/16) | 32 | >128 | >128 |
| | 1 (1/32) | 32 | >128 | >128 |
| PapMA-24 Concentration (Conc./MIC) | 64 (4) | 0 | 0 | 0 |
| | 32 (2) | 0 | 0 | 0 |
| | 16 (1) | 0 | 0 | 0 |
| | 8 (1/2) | 0.5 | 8 | 4 |
| | 6 (1/3) | 2 | 16 | 8 |
| | 4 (1/4) | 8 | 64 | 64 |
| | 2 (1/8) | 32 | 128 | >128 |

Antibacterial activity of antibiotic against *A. baumannii* during treatment with PapMA-1 to PapMA-24 antimicrobial peptides

TABLE 12

| Peptide treatment concentration (µg/ml) | | Antibiotic MIC (µg/ml) | | |
|---|---|---|---|---|
| | | Erythromycin | Vancomycin | Linezolid |
| Compound Alone | | 32 | >1024 | 512 |
| PapMA-1 Concentration (Conc./MIC) | 64 (1) | 0 | 0 | 0 |
| | 32 (1/2) | 0.125 | 8 | 4 |
| | 16 (1/4) | 0.25 | 16 | 8 |
| | 8 (1/8) | 0.5 | 16 | 16 |
| | 6 (1/11) | 4 | 32 | 32 |
| | 4 (1/16) | 16 | 128 | 64 |
| | 2 (1/32) | 32 | >128 | 128 |
| | 1 (1/64) | 32 | >128 | >128 |
| PapMA-2 Concentration (Conc./MIC) | 64 (4) | 0 | 0 | 0 |
| | 32 (2) | 0 | 0 | 0 |
| | 16 (1) | 0 | 0 | 0 |
| | 8 (1/2) | 0.25 | 16 | 8 |
| | 6 (1/3) | 2 | 32 | 32 |
| | 4 (1/4) | 4 | 128 | 32 |
| | 2 (1/8) | 16 | >128 | 64 |
| | 1 (1/16) | 32 | >128 | >128 |
| PapMA-3 Concentration (Conc./MIC) | 64 (4) | 0 | 0 | 0 |
| | 32 (2) | 0 | 0 | 0 |
| | 16 (1) | 0 | 0 | 0 |
| | 8 (1/2) | 0.25 | 16 | 16 |
| | 6 (1/3) | 4 | 32 | 32 |
| | 4 (1/4) | 8 | 128 | 32 |
| | 2 (1/8) | 16 | >128 | 128 |
| | 1 (1/16) | 32 | >128 | >128 |
| PapMA-4 Concentration (Conc./MIC) | 64 (4) | 0 | 0 | 0 |
| | 32 (2) | 0 | 0 | 0 |
| | 16 (1) | 0 | 0 | 0 |
| | 8 (1/2) | 2 | 64 | 32 |
| | 6 (1/3) | 4 | 64 | 64 |
| | 4 (1/4) | 8 | 128 | 64 |
| | 2 (1/8) | 16 | >128 | 128 |
| | 1 (1/16) | 32 | >128 | >128 |
| PapMA-5 Concentration (Conc./MIC) | 64 (1) | 0 | 0 | 0 |
| | 32 (1/2) | 0.125 | 4 | 4 |
| | 16 (1/4) | 0.25 | 8 | 8 |
| | 8 (1/8) | 1 | 16 | 8 |
| | 6 (1/11) | 2 | 32 | 16 |
| | 4 (1/16) | 16 | 128 | 64 |
| | 2 (1/32) | 32 | >128 | 128 |
| | 1 (1/64) | 32 | >128 | >128 |
| PapMA-6 Concentration (Conc./MIC) | 64 (1) | 0 | 0 | 0 |
| | 32 (1/2) | 0.0625 | 2 | 1 |
| | 16 (1/4) | 0.125 | 4 | 2 |
| | 8 (1/8) | 0.25 | 8 | 4 |
| | 6 (1/11) | 0.5 | 8 | 8 |
| | 4 (1/16) | 4 | 64 | 16 |
| | 2 (1/32) | 8 | 128 | 32 |
| | 1 (1/64) | 16 | >128 | 128 |
| PapMA-7 Concentration (Conc./MIC) | 64 (2) | 0 | 0 | 0 |
| | 32 (1) | 0 | 0 | 0 |
| | 16 (1/2) | 0.0625 | 1 | 1 |
| | 8 (1/4) | 0.125 | 2 | 2 |
| | 6 (1/5) | 0.5 | 4 | 4 |
| | 4 (1/8) | 2 | 8 | 8 |
| | 2 (1/16) | 4 | 32 | 32 |
| | 1 (1/32) | 8 | 128 | 64 |
| PapMA-8 Concentration (Conc./MIC) | 64 (1) | 0 | 0 | 0 |
| | 32 (1/2) | 1 | 2 | 2 |
| | 16 (1/4) | 2 | 4 | 4 |
| | 8 (1/8) | 4 | 8 | 16 |
| | 6 (1/11) | 8 | 32 | 32 |
| | 4 (1/16) | 16 | 64 | 64 |
| | 2 (1/32) | 32 | >128 | >128 |
| | 1 (1/64) | 32 | >128 | >128 |
| PapMA-9 Concentration (Conc./MIC) | 64 (1) | 0 | 0 | 0 |
| | 32 (1/2) | 0.125 | 2 | 2 |
| | 16 (1/4) | 0.25 | 8 | 4 |
| | 8 (1/8) | 0.25 | 8 | 4 |
| | 6 (1/11) | 0.5 | 16 | 16 |
| | 4 (1/16) | 4 | 64 | 32 |
| | 2 (1/32) | 16 | 128 | 64 |
| | 1 (1/64) | 16 | >128 | >128 |
| PapMA-10 Concentration (Conc./MIC) | 64 (2) | 0 | 0 | 0 |
| | 32 (1) | 0 | 4 | 2 |
| | 16 (1/2) | 4 | 4 | 8 |
| | 8 (1/4) | 8 | 16 | 16 |
| | 6 (1/5) | 8 | 32 | 32 |
| | 4 (1/8) | 16 | 64 | 64 |
| | 2 (1/16) | 32 | >128 | >128 |
| | 1 (1/32) | 32 | >128 | >128 |
| PapMA-11 Concentration (Conc./MIC) | 64 (1) | 0 | 0 | 0 |
| | 32 (1/2) | 0.125 | 4 | 2 |
| | 16 (1/4) | 0.5 | 16 | 8 |
| | 8 (1/8) | 1 | 32 | 16 |
| | 6 (1/11) | 2 | 32 | 32 |
| | 4 (1/16) | 8 | 64 | 64 |
| | 2 (1/32) | 16 | 128 | 128 |
| | 1 (1/64) | 32 | >128 | >128 |
| PapMA-12 Concentration (Conc./MIC) | 64 (8) | 0 | 0 | 0 |
| | 32 (4) | 0 | 0 | 0 |
| | 16 (2) | 0 | 0 | 0 |
| | 8 (1) | 0 | 0 | 0 |
| | 6 (3/4) | 1 | 4 | 8 |
| | 4 (1/2) | 2 | 16 | 16 |
| | 2 (1/4) | 8 | 64 | 64 |
| | 1 (1/8) | 16 | 128 | 128 |
| PapMA-13 Concentration (Conc./MIC) | 64 (4) | 0 | 0 | 0 |
| | 32 (2) | 0 | 0 | 0 |
| | 16 (1) | 0 | 0 | 0 |
| | 8 (1/2) | 0.5 | 1 | 2 |
| | 6 (1/3) | 1 | 2 | 8 |
| | 4 (1/4) | 4 | 16 | 16 |
| | 2 (1/8) | 8 | 64 | 32 |
| | 1 (1/16) | 16 | 128 | 128 |
| PapMA-14 Concentration (Conc./MIC) | 64 (4) | 0 | 0 | 0 |
| | 32 (2) | 0 | 0 | 0 |
| | 16 (1) | 0 | 0 | 0 |
| | 8 (1/2) | 0.5 | 1 | 1 |
| | 6 (1/3) | 1 | 4 | 4 |
| | 4 (1/4) | 4 | 16 | 16 |
| | 2 (1/8) | 8 | 64 | 64 |
| | 1 (1/16) | 16 | >128 | 128 |
| PapMA-15 Concentration (Conc./MIC) | 64 (2) | 0 | 0 | 0 |
| | 32 (1) | 0 | 0 | 0 |
| | 16 (1/2) | 0.25 | 16 | 4 |
| | 8 (1/4) | 1 | 32 | 32 |
| | 6 (1/5) | 2 | 32 | 64 |
| | 4 (1/8) | 16 | 128 | 64 |
| | 2 (1/16) | 32 | >128 | >128 |
| | 1 (1/32) | 32 | >128 | >128 |

TABLE 12-continued

MDRAB 12035

| Peptide treatment concentration | Antibiotic MIC (µg/ml) | | |
|---|---|---|---|
| (µg/ml) | Erythromycin | Vancomycin | Linezolid |
| PapMA-16 | 64 (2) | 0 | 0 | 0 |
| Concentration | 32 (1) | 0 | 0 | 0 |
| (Conc./MIC) | 16 (1/2) | 0.25 | 8 | 8 |
|  | 8 (1/4) | 1 | 16 | 16 |
|  | 6 (1/5) | 4 | 32 | 32 |
|  | 4 (1/8) | 16 | 64 | 128 |
|  | 2 (1/16) | 32 | >128 | >128 |
|  | 1 (1/32) | 32 | >128 | >128 |
| PapMA-17 | 64 (2) | 0 | 0 | 0 |
| Concentration | 32 (1) | 0 | 0 | 0 |
| (Conc./MIC) | 16 (1/2) | 0.25 | 8 | 4 |
|  | 8 (1/4) | 0.5 | 16 | 16 |
|  | 6 (1/5) | 4 | 32 | 32 |
|  | 4 (1/8) | 8 | 128 | 32 |
|  | 2 (1/16) | 16 | >128 | 128 |
|  | 1 (1/32) | 32 | >128 | >128 |
| PapMA-18 | 64 (2) | 0 | 0 | 0 |
| Concentration | 32 (1) | 0 | 0 | 0 |
| (Conc./MIC) | 16 (1/2) | 0.5 | 16 | 8 |
|  | 8 (1/4) | 2 | 16 | 16 |
|  | 6 (1/5) | 4 | 32 | 32 |
|  | 4 (1/8) | 16 | 128 | 64 |
|  | 2 (1/16) | 32 | >128 | >128 |
|  | 1 (1/32) | 32 | >128 | >128 |
| PapMA-19 | 64 (2) | 0 | 0 | 0 |
| Concentration | 32 (1) | 0 | 0 | 0 |
| (Conc./MIC) | 16 (1/2) | 0.125 | 8 | 4 |
|  | 8 (1/4) | 0.5 | 16 | 8 |
|  | 6 (1/5) | 2 | 32 | 16 |
|  | 4 (1/8) | 8 | 64 | 64 |
|  | 2 (1/16) | 16 | 128 | 128 |
|  | 1 (1/32) | 32 | >128 | >128 |
| PapMA-20 | 64 (4) | 0 | 0 | 0 |
| Concentration | 32 (2) | 0 | 0 | 0 |
| (Conc./MIC) | 16 (1) | 0 | 0 | 0 |
|  | 8 (1/2) | 0.5 | 4 | 4 |
|  | 6 (1/3) | 4 | 16 | 16 |
|  | 4 (1/4) | 8 | 64 | 32 |
|  | 2 (1/8) | 16 | >128 | 128 |
|  | 1 (1/16) | 32 | >128 | >128 |
| PapMA-21 | 64 (2) | 0 | 0 | 0 |
| Concentration | 32 (1) | 0 | 0 | 0 |
| (Conc./MIC) | 16 (1/2) | 0.5 | 16 | 8 |
|  | 8 (1/4) | 1 | 32 | 16 |
|  | 6 (1/5) | 4 | 64 | 32 |
|  | 4 (1/8) | 16 | 128 | 64 |
|  | 2 (1/16) | 32 | >128 | >128 |
|  | 1 (1/32) | 32 | >128 | >128 |
| PapMA-22 | 64 (2) | 0 | 0 | 0 |
| Concentration | 32 (1) | 0 | 0 | 0 |
| (Conc./MIC) | 16 (1/2) | 0.25 | 8 | 8 |
|  | 8 (1/4) | 1 | 16 | 16 |
|  | 6 (1/5) | 2 | 32 | 16 |
|  | 4 (1/8) | 16 | 128 | 64 |
|  | 2 (1/16) | 32 | >128 | >128 |
|  | 1 (1/32) | 32 | >128 | >128 |
| PapMA-23 | 64 (2) | 0 | 0 | 0 |
| Concentration | 32 (1) | 0 | 0 | 0 |
| (Conc./MIC) | 16 (1/2) | 0.25 | 8 | 4 |
|  | 8 (1/4) | 1 | 16 | 16 |
|  | 6 (1/5) | 4 | 32 | 32 |
|  | 4 (1/8) | 16 | 128 | 64 |
|  | 2 (1/16) | 32 | >128 | >128 |
|  | 1 (1/32) | 32 | >128 | >128 |
| PapMA-24 | 64 (2) | 0 | 0 | 0 |
| Concentration | 32 (1) | 0 | 0 | 0 |
| (Conc./MIC) | 16 (1/2) | 0.25 | 8 | 4 |
|  | 8 (1/4) | 1 | 16 | 8 |
|  | 6 (1/5) | 2 | 32 | 16 |
|  | 4 (1/8) | 16 | 64 | 64 |
|  | 2 (1/16) | 32 | >128 | >128 |
|  | 1 (1/32) | 32 | >128 | >128 |

Antibacterial activity of antibiotic against MDRAB 12035 during treatment with PapMA-1 to PapMA-24 antimicrobial peptides Further, as a result of identifying the antibacterial activity of the antibiotics against *E. coli* and *A. baumannii* by mixing the antibiotics with papiliocin as a comparative control as confirmed in the following [Table 13], it can be seen that papiliocin itself has very excellent antibacterial activity, but the antibacterial activity of the combination of papiliocin with the antibiotics does not have a great synergistic effect as compared to the peptides of the present invention.

TABLE 13

| MIC Concentration (µg/ml) | | | | | | | |
|---|---|---|---|---|---|---|---|
| Peptide treatment concentration | | *E. coli* | | | *A. baumannii* | | |
| (µg/ml) | | Erythromycin | Vancomycin | Linezolid | Erythromycin | Vancomycin | Linezolid |
| Compound alone | | 128 | 1024 | 256 | 32 | 1024 | 256 |
| Papiliocin | 8 (1) | 0 | 0 | 0 | 0 | 0 | 0 |
| concentration | 4 (1/2) | 64 | 256 | 128 | 16 | 256 | 64 |
| (Conc./MIC) | 2 (1/4) | 64 | 256 | 128 | 16 | 256 | 64 |
|  | 1 (1/8) | 64 | 512 | 128 | 32 | 512 | 128 |

Antibacterial activity of antibiotics against *E. coli* and *A. baumannii* during treatment with papiliocin as comparative control <3-2> Identification of Variation in MIC of Antimicrobial Peptide During Combined Treatment of Antimicrobial Peptide and Antibiotic Since it was confirmed that during the combined treatment of the antimicrobial peptide and the antibiotic, the MIC of the antibiotics could be significantly reduced due to the synergistic effect, it was confirmed whether the MIC concentration of the antimicrobial peptide was changed during the combined treatment of the antimicrobial peptide and the antibiotic.

As a result, as shown in the following [Table 14] to [Table 33], as a result of measuring the antibacterial activity of the antibacterial peptide when the was antibiotics were added, it was confirmed that when the antibiotics were added to *E. coli* and a resistant strain thereof (MDREC 1229) and *A. baumannii* and a resistant strain thereof (MDRAB 12035), the MIC of the antibacterial peptide was lowered by 256 times (Tables 14 to 33).

For example, as identified in the present invention, the MIC value of erythromycin against MDRAB 12035 which is a multi-drug resistant strain of *A. baumannii* is 32 μg/ml. Based on erythromycin, a synergistic effect due to the combined treatment of the antimicrobial peptide and existing antibiotics can be identified. It was confirmed that when MDRAB 12035 was treated during the combined treatment of the PapMA-1 peptide at 8 μg/ml which is a 1/4 concentration of the MIC of erythromycin, the MIC value of PapMA-1 was reduced to 4 μg/ml which is a 1/16 level than the MIC value during the single treatment with the antimicrobial peptide. In contrast, by confirming that when the derivative peptide of the present invention was applied, the MICs of PapMA-2 to PapMA-24 were reduced to 1 to 8 μg/ml during the treatment with erythromycin at a concentration of 8 μg/ml, and thus was reduced to 1/4 to 1/32 levels of the MIC value during the treatment with the derivative peptide alone, it was confirmed that a synergistic effect at antibacterial activity was exhibited during the combined treatment of the antimicrobial peptide of the present invention with the antibiotics (Tables 29 to 33).

When compared with the same method, by confirming that during the combined treatment of the PapMA-1 to PapMA-24 peptides while the existing antibiotics of the present invention were treated at a 1/4 concentration of the MIC, even when the antimicrobial peptide was treated at a 1/2 to 1/128 level concentration, significant antibacterial activity was exhibited against *E. coli* and a resistant strain thereof (MDREC 1229) and *A. baumannii* and a resistant strain thereof (MDRAB 12035), it was confirmed that synergistic antibacterial activity at a level similar to or increased more than that of PapMA-1 was exhibited (Tables 14 to 33).

TABLE 14

*E. coli*

| Antibiotic treatment concentration (μg/ml) | | PapMA-1 | PapMA-2 | PapMA-3 | PapMA-4 |
|---|---|---|---|---|---|
| Peptide alone | | 64 | 64 | 32 | 16 |
| Erythromycin | 128 (1) | 0 | 0 | 0 | 0 |
| concentration | 64 (1/2) | 1 | 1 | 1 | 1 |
| (Conc./MIC) | 32 (1/4) | 2 | 2 | 2 | 2 |
| | 16 (1/8) | 4 | 4 | 2 | 4 |
| Vancomycin | 1024 (1) | 0 | 0 | 0 | 0 |
| concentration | 512 (1/2) | 2 | 2 | 2 | 2 |
| (Conc./MIC) | 256 (1/4) | 4 | 4 | 4 | 4 |
| | 128 (1/8) | 8 | 8 | 8 | 8 |
| Linezolid | 256 (1) | 0 | 0 | 0 | 0 |
| concentration | 128 (1/2) | 1 | 1 | 1 | 1 |
| (Conc./MIC) | 64 (1/4) | 4 | 2 | 2 | 2 |
| | 32 (1/8) | 4 | 4 | 4 | 4 |

Antibacterial activity of PapMA-1 to PapMA-4 peptides against *E. coli* during treatment with antibiotic

TABLE 15

*E. coli*

| Antibiotic treatment concentration (μg/ml) | | PapMA-1 | PapMA-5 | PapMA-6 | PapMA-7 | PapMA-8 | PapMA-9 | PapMA-10 |
|---|---|---|---|---|---|---|---|---|
| Peptide alone | | 64 | 64 | 64 | 32 | 32 | 32 | 32 |
| Erythromycin | 128 (1) | 0 | 0 | 0 | 0 | 0 | 0 | 0 |
| concentration | 64 (1/2) | 1 | 2 | 1 | 2 | 2 | 2 | 2 |
| (Conc./MIC) | 32 (1/4) | 2 | 4 | 2 | 2 | 4 | 4 | 4 |
| | 16 (1/8) | 4 | 8 | 2 | 4 | 4 | 4 | 8 |
| Vancomycin | 1024 (1) | 0 | 0 | 0 | 0 | 0 | 0 | 0 |
| concentration | 512 (1/2) | 2 | 2 | 2 | 2 | 2 | 2 | 2 |
| (Conc./MIC) | 256 (1/4) | 4 | 4 | 2 | 2 | 2 | 4 | 4 |
| | 128 (1/8) | 8 | 4 | 2 | 2 | 4 | 4 | 4 |
| Linezolid | 256 (1) | 0 | 0 | 0 | 0 | 0 | 0 | 0 |
| concentration | 128 (1/2) | 1 | 2 | 4 | 2 | 4 | 4 | 4 |
| (Conc./MIC) | 64 (1/4) | 4 | 4 | 4 | 4 | 4 | 4 | 4 |
| | 32 (1/8) | 4 | 8 | 4 | 4 | 4 | 4 | 8 |

Antibacterial activity of PapMA-5 to PapMA-10 peptides against *E. coli* during treatment with antibiotic

TABLE 16

*E. coli*

| Antibiotic treatment concentration (μg/ml) | | PapMA-1 | PapMA-11 | PapMA-12 | PapMA-13 | PapMA-14 |
|---|---|---|---|---|---|---|
| Peptide alone | | 64 | 64 | 8 | 16 | 8 |
| Erythromycin | 128 (1) | 0 | 0 | 0 | 0 | 0 |
| concentration | 64 (1/2) | 1 | 1 | 1 | 1 | 1 |

TABLE 16-continued

E. coli

| Antibiotic treatment concentration (μg/ml) | | Peptide MIC (μg/ml) | | | | |
|---|---|---|---|---|---|---|
| | | PapMA-1 | PapMA-11 | PapMA-12 | PapMA-13 | PapMA-14 |
| (Conc./MIC) | 32 (1/4) | 2 | 4 | 2 | 2 | 2 |
| | 16 (1/8) | 4 | 4 | 4 | 2 | 4 |
| Vancomycin concentration (Conc./MIC) | 1024 (1) | 0 | 0 | 0 | 0 | 0 |
| | 512 (1/2) | 2 | 2 | 1 | 1 | 1 |
| | 256 (1/4) | 4 | 2 | 2 | 2 | 2 |
| | 128 (1/8) | 8 | 8 | 2 | 2 | 2 |
| Linezolid concentration (Conc./MIC) | 256 (1) | 0 | 0 | 0 | 0 | 0 |
| | 128 (1/2) | 1 | 2 | 2 | 2 | 2 |
| | 64 (1/4) | 4 | 8 | 4 | 2 | 4 |
| | 32 (1/8) | 4 | 8 | 4 | 4 | 4 |

Antibacterial activity of PapMA-11 to PapMA-14 peptides against E. coli during treatment with antibiotic

TABLE 17

E. coli

| Antibiotic treatment concentration (μg/ml) | | PapMA-1 | PapMA-15 | PapMA-16 | PapMA-17 | PapMA-18 | PapMA-19 | PapMA-20 |
|---|---|---|---|---|---|---|---|---|
| Peptide alone | | 64 | 32 | 64 | 16 | 64 | 32 | 16 |
| Erythromycin concentration (Conc./MIC) | 128 (1) | 0 | 0 | 0 | 0 | 0 | 0 | 0 |
| | 64 (1/2) | 1 | 1 | 2 | 2 | 2 | 1 | 1 |
| | 32 (1/4) | 2 | 2 | 2 | 2 | 2 | 2 | 2 |
| | 16 (1/8) | 4 | 4 | 4 | 4 | 4 | 4 | 4 |
| Vancomycin concentration (Conc./MIC) | 1024 (1) | 0 | 0 | 0 | 0 | 0 | 0 | 0 |
| | 512 (1/2) | 2 | 2 | 2 | 2 | 2 | 2 | 2 |
| | 256 (1/4) | 4 | 4 | 4 | 4 | 4 | 2 | 2 |
| | 128 (1/8) | 8 | 8 | 4 | 4 | 4 | 2 | 4 |
| Linezolid concentration (Conc./MIC) | 256 (1) | 0 | 0 | 0 | 0 | 0 | 0 | 0 |
| | 128 (1/2) | 1 | 2 | 4 | 4 | 4 | 2 | 2 |
| | 64 (1/4) | 4 | 4 | 4 | 4 | 4 | 2 | 2 |
| | 32 (1/8) | 4 | 4 | 4 | 4 | 8 | 4 | 4 |

Antibacterial activity of PapMA-15 to PapMA-20 peptides against E. coli during treatment with antibiotic

TABLE 18

E. coli

| Antibiotic treatment concentration (μg/ml) | | Peptide MIC (μg/ml) | | | | |
|---|---|---|---|---|---|---|
| | | PapMA-1 | PapMA-21 | PapMA-22 | PapMA-23 | PapMA-24 |
| Peptide alone | | 64 | 32 | 32 | 32 | 32 |
| Erythromycin concentration (Conc./MIC) | 128 (1) | 0 | 0 | 0 | 0 | 0 |
| | 64 (1/2) | 1 | 1 | 2 | 2 | 1 |
| | 32 (1/4) | 2 | 2 | 2 | 4 | 2 |
| | 16 (1/8) | 4 | 4 | 4 | 4 | 4 |
| Vancomycin concentration (Conc./MIC) | 1024 (1) | 0 | 0 | 0 | 0 | 0 |
| | 512 (1/2) | 2 | 2 | 2 | 2 | 2 |
| | 256 (1/4) | 4 | 4 | 4 | 4 | 4 |
| | 128 (1/8) | 8 | 8 | 4 | 8 | 4 |
| Linezolid concentration (Conc./MIC) | 256 (1) | 0 | 0 | 0 | 0 | 0 |
| | 128 (1/2) | 1 | 2 | 2 | 2 | 2 |
| | 64 (1/4) | 4 | 4 | 4 | 4 | 4 |
| | 32 (1/8) | 4 | 8 | 8 | 8 | 8 |

Antibacterial activity of PapMA-21 to PapMA-24 peptides against E. coli during treatment with antibiotic

TABLE 19

MDREC 1229

| Antibiotic treatment concentration (μg/ml) | | Peptide MIC (μg/ml) | | | |
|---|---|---|---|---|---|
| | | PapMA-1 | PapMA-2 | PapMA-3 | PapMA-4 |
| Peptide alone | | 64 | 64 | 32 | 32 |
| Erythromycin concentration (Conc./MIC) | 256 (1) | 0 | 0 | 0 | 0 |
| | 128 (1/2) | 1 | 1 | 0.5 | 0.5 |
| | 64 (1/4) | 1 | 1 | 1 | 1 |
| | 32 (1/8) | 2 | 2 | 2 | 2 |
| Vancomycin concentration (Conc./MIC) | 1024 (1) | 1 | 1 | 1 | 1 |
| | 512 (1/2) | 2 | 2 | 2 | 2 |
| | 256 (1/4) | 4 | 4 | 4 | 4 |
| | 128 (1/8) | 8 | 8 | 8 | 8 |

TABLE 19-continued

MDREC 1229

| Antibiotic treatment concentration (μg/ml) | | Peptide MIC (μg/ml) | | | |
|---|---|---|---|---|---|
| | | PapMA-1 | PapMA-2 | PapMA-3 | PapMA-4 |
| Linezolid concentration (Conc./MIC) | 512 (1) | 0 | 0 | 0 | 0 |
| | 256 (1/2) | 1 | 1 | 1 | 1 |
| | 128 (1/4) | 2 | 1 | 2 | 2 |
| | 64 (1/8) | 2 | 2 | 1 | 2 |

Antibacterial activity of PapMA-1 to PapMA-4 peptides against MDREC 1229 during treatment with antibiotic

TABLE 20

MDREC 1229

| Antibiotic treatment concentration (μg/ml) | Peptide MIC (μg/ml) | | | | | | |
|---|---|---|---|---|---|---|---|
| | PapMA-1 | PapMA-5 | PapMA-6 | PapMA-7 | PapMA-8 | PapMA-9 | PapMA-10 |
| Peptide alone | 64 | 64 | 64 | 64 | 64 | 64 | 64 |
| Erythromycin 256 (1) | 0 | 0 | 0 | 0 | 0 | 0 | 0 |
| concentration 128 (1/2) | 1 | 1 | 0.5 | 0.5 | 2 | 1 | 2 |
| (Conc./MIC) 64 (1/4) | 1 | 2 | 1 | 1 | 2 | 1 | 2 |
| 32 (1/8) | 2 | 4 | 2 | 2 | 4 | 2 | 4 |
| Vancomycin 1024 (1) | 1 | 2 | 1 | 1 | 2 | 2 | 4 |
| concentration 512 (1/2) | 2 | 2 | 2 | 2 | 2 | 4 | 4 |
| (Conc./MIC) 256 (1/4) | 4 | 4 | 4 | 4 | 8 | 4 | 4 |
| 128 (1/8) | 8 | 8 | 8 | 4 | 8 | 4 | 8 |
| Linezolid 512 (1) | 0 | 0 | 0 | 0 | 0 | 0 | 0 |
| concentration 256 (1/2) | 1 | 1 | 0.5 | 0.5 | 2 | 1 | 2 |
| (Conc./MIC) 128 (1/4) | 2 | 1 | 1 | 1 | 4 | 1 | 4 |
| 64 (1/8) | 2 | 4 | 2 | 2 | 8 | 2 | 8 |

Antibacterial activity of PapMA-5 to PapMA-10 peptides against MDREC 1229 during treatment with antibiotic

TABLE 21

MDREC 1229

| Antibiotic treatment concentration (μg/ml) | Peptide MIC (μg/ml) | | | | |
|---|---|---|---|---|---|
| | PapMA-1 | PapMA-11 | PapMA-12 | PapMA-13 | PapMA-14 |
| Peptide alone | 64 | 64 | 16 | 16 | 16 |
| Erythromycin 256 (1) | 0 | 0 | 0 | 0 | 0 |
| concentration 128 (1/2) | 1 | 1 | 1 | 2 | 1 |
| (Conc./MIC) 64 (1/4) | 1 | 2 | 2 | 2 | 2 |
| 32 (1/8) | 2 | 4 | 2 | 2 | 2 |
| Vancomycin 1024 (1) | 1 | 1 | 1 | 1 | 1 |
| concentration 512 (1/2) | 2 | 2 | 2 | 2 | 2 |
| (Conc./MIC) 256 (1/4) | 4 | 4 | 4 | 4 | 4 |
| 128 (1/8) | 8 | 8 | 4 | 8 | 4 |
| Linezolid 512 (1) | 0 | 0 | 0 | 0 | 0 |
| concentration 256 (1/2) | 1 | 2 | 1 | 2 | 1 |
| (Conc./MIC) 128 (1/4) | 2 | 4 | 2 | 2 | 2 |
| 64 (1/8) | 2 | 8 | 4 | 4 | 4 |

Antibacterial activity of PapMA-11 to PapMA-14 peptides against MDREC 1229 during treatment with antibiotic

TABLE 23

MDREC 1229

| Antibiotic treatment concentration (μg/ml) | Peptide MIC (μg/ml) | | | | |
|---|---|---|---|---|---|
| | PapMA-1 | PapMA-21 | PapMA-22 | PapMA-23 | PapMA-24 |
| Peptide alone | 64 | 32 | 32 | 32 | 32 |
| Erythromycin 256 (1) | 0 | 0 | 0 | 0 | 0 |
| concentration 128 (1/2) | 1 | 1 | 1 | 1 | 1 |
| (Conc./MIC) 64 (1/4) | 1 | 2 | 2 | 2 | 2 |
| 32 (1/8) | 2 | 2 | 2 | 4 | 4 |
| Vancomycin 1024 (1) | 1 | 2 | 2 | 1 | 1 |
| concentration 512 (1/2) | 2 | 2 | 2 | 2 | 2 |
| (Conc./MIC) 256 (1/4) | 4 | 4 | 4 | 4 | 4 |
| 128 (1/8) | 8 | 8 | 8 | 8 | 8 |
| Linezolid 512 (1) | 0 | 0 | 0 | 0 | 0 |
| concentration 256 (1/2) | 1 | 1 | 1 | 1 | 1 |
| (Conc./MIC) 128 (1/4) | 2 | 4 | 4 | 2 | 2 |
| 64 (1/8) | 2 | 8 | 8 | 4 | 4 |

Antibacterial activity of PapMA-21 to PapMA-24 peptides against MDREC 1229 during treatment with antibiotic

TABLE 22

MDREC 1229

| Antibiotic treatment concentration (μg/ml) | Peptide MIC (μg/ml) | | | | | | |
|---|---|---|---|---|---|---|---|
| | PapMA-1 | PapMA-15 | PapMA-16 | PapMA-17 | PapMA-18 | PapMA-19 | PapMA-20 |
| Peptide alone | 64 | 32 | 64 | 16 | 64 | 32 | 16 |
| Erythromycin 256 (1) | 0 | 0 | 0 | 0 | 0 | 0 | 0 |
| concentration 128 (1/2) | 1 | 2 | 2 | 2 | 2 | 1 | 1 |
| (Conc./MIC) 64 (1/4) | 2 | 2 | 2 | 2 | 2 | 2 | 2 |
| 32 (1/8) | 2 | 2 | 4 | 2 | 2 | 2 | 2 |
| Vancomycin 1024 (1) | 1 | 1 | 1 | 1 | 1 | 1 | 1 |
| concentration 512 (1/2) | 2 | 2 | 2 | 2 | 2 | 2 | 2 |
| (Conc./MIC) 256 (1/4) | 4 | 4 | 4 | 4 | 4 | 4 | 4 |
| 128 (1/8) | 8 | 8 | 8 | 8 | 8 | 4 | 4 |
| Linezolid 512 (1) | 0 | 0 | 0 | 0 | 0 | 0 | 0 |
| concentration 256 (1/2) | 1 | 1 | 1 | 1 | 1 | 1 | 1 |
| (Conc./MIC) 128 (1/4) | 2 | 2 | 2 | 4 | 4 | 2 | 2 |
| 64 (1/8) | 4 | 4 | 4 | 4 | 4 | 4 | 2 |

Antibacterial activity of PapMA-15 to PapMA-20 peptides against MDREC 1229 during treatment with antibiotic

TABLE 24

A. baumannii

| Antibiotic treatment concentration (µg/ml) | Peptide MIC (µg/ml) | | | |
|---|---|---|---|---|
| | PapMA-1 | PapMA-2 | PapMA-3 | PapMA-4 |
| Peptide alone | 64 | 16 | 16 | 16 |
| Erythromycin 32 (1) | 0 | 0 | 0 | 0 |
| concentration 16 (1/2) | 2 | 1 | 2 | 2 |
| (Conc./MIC) 8 (1/4) | 4 | 4 | 4 | 4 |
| 4 (1/8) | 4 | 4 | 4 | 8 |
| Vancomycin 1024 (1) | 0 | 0 | 0 | 0 |
| concentration 512 (1/2) | 0.25 | 0.25 | 0.25 | 0.25 |
| (Conc./MIC) 256 (1/4) | 0.5 | 0.5 | 0.25 | 0.25 |
| 128 (1/8) | 4 | 2 | 2 | 2 |
| Linezolid 256 (1) | 0 | 0 | 0 | 0 |
| concentration 128 (1/2) | 0.5 | 0.5 | 1 | 1 |
| (Conc./MIC) 64 (1/4) | 4 | 4 | 2 | 4 |
| 32 (1/8) | 4 | 4 | 4 | 4 |

Antibacterial activity of PapMA-1 to PapMA-4 peptides against *A. baumannii* during treatment with antibiotic

TABLE 25

A. baumannii

| Antibiotic treatment concentration (µg/ml) | Peptide MIC (µg/ml) | | | | | | |
|---|---|---|---|---|---|---|---|
| | PapMA-1 | PapMA-5 | PapMA-6 | PapMA-7 | PapMA-8 | PapMA-9 | PapMA-10 |
| Peptide alone | 64 | 64 | 32 | 16 | 32 | 32 | 16 |
| Erythromycin 32 (1) | 0 | 0 | 0 | 0 | 0 | 0 | 0 |
| concentration 16 (1/2) | 2 | 2 | 1 | 1 | 2 | 2 | 2 |
| (Conc./MIC) 8 (1/4) | 4 | 4 | 2 | 2 | 4 | 2 | 4 |
| 4 (1/8) | 4 | 8 | 4 | 2 | 4 | 4 | 8 |
| Vancomycin 1024 (1) | 0 | 0 | 0 | 0 | 0 | 0 | 0 |
| concentration 512 (1/2) | 0.25 | 0.5 | 0.25 | 0.25 | 1 | 0.25 | 1 |
| (Conc./MIC) 256 (1/4) | 0.5 | 1 | 0.5 | 0.25 | 1 | 0.5 | 1 |
| 128 (1/8) | 4 | 4 | 2 | 2 | 4 | 2 | 4 |
| Linezolid 256 (1) | 0 | 0 | 0 | 0 | 0 | 0 | 0 |
| concentration 128 (1/2) | 0.5 | 1 | 1 | 1 | 2 | 2 | 4 |
| (Conc./MIC) 64 (1/4) | 4 | 2 | 2 | 2 | 2 | 4 | 4 |
| 32 (1/8) | 4 | 4 | 4 | 2 | 4 | 4 | 8 |

Antibacterial activity of PapMA-5 to PapMA-10 peptides against *A. baumannii* during treatment with antibiotic

TABLE 26

A. baumannii

| Antibiotic treatment concentration (µg/ml) | Peptide MIC (µg/ml) | | | | |
|---|---|---|---|---|---|
| | PapMA-1 | PapMA-11 | Pap-MA-12 | PapMA-13 | PapMA-14 |
| Peptide alone | 64 | 64 | 8 | 16 | 16 |
| Erythromycin 32 (1) | 0 | 0 | 0 | 0 | 0 |
| concentration 16 (1/2) | 2 | 2 | 1 | 1 | 1 |
| (Conc./MIC) 8 (1/4) | 4 | 4 | 2 | 2 | 2 |
| 4 (1/8) | 4 | 4 | 4 | 4 | 4 |
| Vancomycin 1024 (1) | 0 | 0 | 0 | 0 | 0 |
| concentration 512 (1/2) | 0.25 | 0.25 | 0.25 | 0.25 | 0.25 |
| (Conc./MIC) 256 (1/4) | 0.5 | 0.5 | 0.25 | 0.25 | 0.5 |
| 128 (1/8) | 4 | 2 | 2 | 1 | 2 |
| Linezolid 256 (1) | 0 | 0 | 0 | 0 | 0 |
| concentration 128 (1/2) | 0.5 | 2 | 1 | 1 | 1 |
| (Conc./MIC) 64 (1/4) | 4 | 4 | 2 | 2 | 2 |
| 32 (1/8) | 4 | 8 | 2 | 2 | 2 |

Antibacterial activity of PapMA-11 to PapMA-14 peptides against *A. baumannii* during treatment with antibiotic

TABLE 27

*A. baumannii*

| Antibiotic treatment concentration (μg/ml) | | Peptide MIC (μg/ml) | | | | | | |
|---|---|---|---|---|---|---|---|---|
| | | PapMA-1 | PapMA-15 | PapMA-16 | PapMA-17 | PapMA-18 | PapMA-19 | PapMA-20 |
| Peptide alone | | 64 | 32 | 32 | 32 | 32 | 16 | 16 |
| Erythromycin concentration (Conc./MIC) | 32 (1) | 0 | 0 | 0 | 0 | 0 | 0 | 0 |
| | 16 (1/2) | 2 | 4 | 2 | 2 | 4 | 2 | 2 |
| | 8 (1/4) | 4 | 4 | 4 | 4 | 4 | 4 | 4 |
| | 4 (1/8) | 4 | 4 | 4 | 4 | 4 | 4 | 4 |
| Vancomycin concentration (Conc./MIC) | 1024 (1) | 0 | 0 | 0 | 0 | 0 | 0 | 0 |
| | 512 (1/2) | 0.25 | 0.25 | 0.25 | 0.25 | 0.25 | 0.25 | 0.25 |
| | 256 (1/4) | 0.5 | 0.5 | 0.5 | 0.5 | 0.5 | 0.5 | 0.5 |
| | 128 (1/8) | 4 | 2 | 2 | 4 | 4 | 2 | 4 |
| Linezolid concentration (Conc./MIC) | 256 (1) | 0 | 0 | 0 | 0 | 0 | 0 | 0 |
| | 128 (1/2) | 0.5 | 2 | 4 | 2 | 2 | 1 | 1 |
| | 64 (1/4) | 4 | 4 | 8 | 2 | 4 | 2 | 2 |
| | 32 (1/8) | 4 | 8 | 8 | 4 | 8 | 4 | 4 |

Antibacterial activity of PapMA-15 to PapMA-20 peptides against *A. baumannii* during treatment with antibiotic

TABLE 28

*A. baumannii*

| Antibiotic treatment concentration (μg/ml) | | Peptide MIC (μg/ml) | | | | |
|---|---|---|---|---|---|---|
| | | PapMA-1 | PapMA-21 | PapMA-22 | PapMA-23 | PapMA-24 |
| Peptide alone | | 64 | 32 | 16 | 32 | 16 |
| Erythromycin concentration (Conc./MIC) | 32 (1) | 0 | 0 | 0 | 0 | 0 |
| | 16 (1/2) | 2 | 2 | 4 | 4 | 4 |
| | 8 (1/4) | 4 | 4 | 4 | 4 | 4 |
| | 4 (1/8) | 4 | 8 | 8 | 8 | 8 |
| Vancomycin concentration (Conc./MIC) | 1024 (1) | 0 | 0 | 0 | 0 | 0 |
| | 512 (1/2) | 0.25 | 0.25 | 0.25 | 0.25 | 0.25 |
| | 256 (1/4) | 0.5 | 0.5 | 0.5 | 0.5 | 0.5 |
| | 128 (1/8) | 4 | 4 | 2 | 4 | 2 |
| Linezolid concentration (Conc./MIC) | 256 (1) | 0 | 0 | 0 | 0 | 0 |
| | 128 (1/2) | 0.5 | 1 | 1 | 1 | 1 |
| | 64 (1/4) | 4 | 4 | 4 | 4 | 4 |
| | 32 (1/8) | 4 | 4 | 4 | 8 | 8 |

Antibacterial activity of PapMA-21 to PapMA-24 peptides against *A. baumannii* during treatment with antibiotic

TABLE 29

MDRAB 12035

| Antibiotic treatment concentration (μg/ml) | | Peptide MIC (μg/ml) | | | |
|---|---|---|---|---|---|
| | | PapMA-1 | PapMA-2 | PapMA-3 | PapMA-4 |
| Peptide alone | | 64 | 16 | 16 | 16 |
| Erythromycin concentration (Conc./MIC) | 32 (1) | 0 | 0 | 0 | 0 |
| | 16 (1/2) | 4 | 2 | 2 | 2 |
| | 8 (1/4) | 4 | 4 | 4 | 4 |
| | 4 (1/8) | 4 | 4 | 4 | 4 |
| Vancomycin concentration (Conc./MIC) | 1024 (1) | 1 | 0.25 | 0.25 | 0.25 |
| | 512 (1/2) | 2 | 1 | 2 | 2 |
| | 256 (1/4) | 4 | 2 | 2 | 2 |
| | 128 (1/8) | 4 | 4 | 4 | 4 |
| Linezolid concentration (Conc./MIC) | 512 (1) | 0 | 0 | 0 | 0 |
| | 256 (1/2) | 1 | 1 | 1 | 1 |
| | 128 (1/4) | 4 | 2 | 2 | 2 |
| | 64 (1/8) | 4 | 4 | 4 | 4 |

Antibacterial activity of PapMA-1 to PapMA-4 peptides against MDRAB 12035 during treatment with antibiotic

TABLE 30

MDRAB 12035

| Antibiotic treatment concentration (μg/ml) | | Peptide MIC (μg/ml) | | | | | | |
|---|---|---|---|---|---|---|---|---|
| | | PapMA-1 | PapMA-5 | PapMA-6 | PapMA-7 | PapMA-8 | PapMA-9 | PapMA-10 |
| Peptide alone | | 64 | 64 | 64 | 32 | 64 | 64 | 32 |
| Erythromycin concentration (Conc./MIC) | 32 (1) | 0 | 0 | 0 | 0 | 0 | 0 | 0 |
| | 16 (1/2) | 4 | 4 | 1 | 1 | 4 | 1 | 4 |
| | 8 (1/4) | 4 | 4 | 2 | 1 | 8 | 4 | 8 |
| | 4 (1/8) | 4 | 4 | 4 | 2 | 8 | 4 | 16 |
| Vancomycin concentration (Conc./MIC) | 1024 (1) | 1 | 1 | 0.25 | 0.25 | 1 | 0.25 | 1 |
| | 512 (1/2) | 2 | 2 | 1 | 0.5 | 2 | 1 | 2 |
| | 256 (1/4) | 4 | 4 | 2 | 1 | 2 | 1 | 4 |
| | 128 (1/8) | 4 | 4 | 2 | 1 | 4 | 2 | 4 |
| Linezolid concentration (Conc./MIC) | 512 (1) | 0 | 0 | 0 | 0 | 0 | 0 | 0 |
| | 256 (1/2) | 1 | 1 | 1 | 1 | 1 | 1 | 2 |
| | 128 (1/4) | 4 | 4 | 1 | 1 | 2 | 2 | 2 |
| | 64 (1/8) | 4 | 4 | 2 | 1 | 4 | 2 | 4 |

Antibacterial activity of PapMA-5 to PapMA-10 peptides against MDRAB 12035 during treatment with antibiotics

TABLE 31

MDRAB 12035

| Antibiotic treatment concentration (µg/ml) | | Peptide MIC (µg/ml) | | | | |
|---|---|---|---|---|---|---|
| | | PapMA-1 | PapMA-11 | PapMA-12 | PapMA-13 | PapMA-14 |
| Peptide alone | | 64 | 64 | 8 | 16 | 16 |
| Erythromycin concentration (Conc./MIC) | 32 (1) | 0 | 0 | 0 | 0 | 0 |
| | 16 (1/2) | 4 | 2 | 1 | 1 | 1 |
| | 8 (1/4) | 4 | 4 | 2 | 2 | 2 |
| | 4 (1/8) | 4 | 4 | 4 | 4 | 4 |
| Vancomycin concentration (Conc./MIC) | 1024 (1) | 1 | 1 | 1 | 1 | 1 |
| | 512 (1/2) | 2 | 1 | 2 | 1 | 1 |
| | 256 (1/4) | 4 | 2 | 2 | 1 | 2 |
| | 128 (1/8) | 4 | 2 | 2 | 2 | 2 |
| Linezolid concentration (Conc./MIC) | 512 (1) | 0 | 0 | 0 | 0 | 0 |
| | 256 (1/2) | 1 | 2 | 1 | 1 | 1 |
| | 128 (1/4) | 4 | 2 | 1 | 1 | 1 |
| | 64 (1/8) | 4 | 4 | 2 | 2 | 2 |

Antibacterial activity of PapMA-11 to PapMA-14 peptides against MDRAB 12035 during treatment with antibiotic

TABLE 32

MDRAB 12035

| Antibiotic treatment concentration (µg/ml) | | Peptide MIC (µg/ml) | | | | | | |
|---|---|---|---|---|---|---|---|---|
| | | PapMA-1 | PapMA-15 | PapMA-16 | PapMA-17 | PapMA-18 | PapMA-19 | PapMA-20 |
| Peptide alone | | 64 | 32 | 32 | 32 | 32 | 32 | 16 |
| Erythromycin concentration (Conc./MIC) | 32 (1) | 0 | 0 | 0 | 0 | 0 | 0 | 0 |
| | 16 (1/2) | 4 | 4 | 4 | 2 | 4 | 2 | 2 |
| | 8 (1/4) | 4 | 4 | 4 | 4 | 4 | 4 | 4 |
| | 4 (1/8) | 4 | 4 | 4 | 4 | 4 | 4 | 4 |
| Vancomycin concentration (Conc./MIC) | 1024 (1) | 1 | 1 | 1 | 1 | 1 | 1 | 1 |
| | 512 (1/2) | 2 | 2 | 2 | 2 | 2 | 2 | 2 |
| | 256 (1/4) | 4 | 2 | 4 | 4 | 4 | 2 | 2 |
| | 128 (1/8) | 4 | 4 | 8 | 4 | 4 | 2 | 4 |
| Linezolid concentration (Conc./MIC) | 512 (1) | 0 | 0 | 0 | 0 | 0 | 0 | 0 |
| | 256 (1/2) | 1 | 1 | 1 | 1 | 1 | 1 | 1 |
| | 128 (1/4) | 4 | 4 | 4 | 2 | 4 | 2 | 2 |
| | 64 (1/8) | 4 | 4 | 4 | 4 | 4 | 4 | 4 |

Antibacterial activity of PapMA-15 to PapMA-20 peptides against MDRAB 12035 during treatment with antibiotic

TABLE 33

MDRAB 12035

| Antibiotic treatment concentration (µg/ml) | | Peptide MIC (µg/ml) | | | | |
|---|---|---|---|---|---|---|
| | | PapMA-1 | PapMA-21 | PapMA-22 | PapMA-23 | PapMA-24 |
| Peptide alone | | 64 | 32 | 32 | 32 | 32 |
| Erythromycin concentration (Conc./MIC) | 32 (1) | 0 | 0 | 0 | 0 | 0 |
| | 16 (1/2) | 4 | 4 | 4 | 4 | 4 |
| | 8 (1/4) | 4 | 8 | 8 | 8 | 8 |
| | 4 (1/8) | 4 | 8 | 8 | 8 | 8 |
| Vancomycin concentration (Conc./MIC) | 1024 (1) | 1 | 1 | 1 | 1 | 1 |
| | 512 (1/2) | 2 | 2 | 4 | 2 | 2 |
| | 256 (1/4) | 4 | 4 | 4 | 4 | 4 |
| | 128 (1/8) | 4 | 4 | 4 | 4 | 4 |
| Linezolid concentration (Conc./MIC) | 512 (1) | 0 | 0 | 0 | 0 | 0 |
| | 256 (1/2) | 1 | 1 | 1 | 1 | 1 |
| | 128 (1/4) | 4 | 4 | 4 | 4 | 4 |
| | 64 (1/8) | 4 | 4 | 4 | 4 | 4 |

Antibacterial activity of PapMA-21 to PapMA-24 peptides against MDRAB 12035 during treatment with antibiotic Further, as identified in the following [Table 34], as a result of identifying the antibacterial activity of papiliocin by mixing the peptides of the present invention with papiliocin which is a comparative control, it can be seen that the antibacterial activity does not have a synergistic effect as compared to the peptides of the present invention (Table 34).

TABLE 34

| | | Peptide MIC (µg/ml) | |
|---|---|---|---|
| Bacteria | Antibiotic single treatment concentration | | Papiliocin 8 |
| E. coli | Erythromycin concentration (Conc./MIC) | 128 (1) | 0 |
| | | 64 (1/2) | 4 |
| | | 32 (1/4) | 4 |
| | | 16 (1/8) | 4 |
| | Vancomycin concentration (Conc./MIC) | 1024 (1) | 0 |
| | | 512 (1/2) | 2 |
| | | 256 (1/4) | 2 |
| | | 128 (1/8) | 4 |
| | Linezolid concentration (Conc./MIC) | 256 (1) | 0 |
| | | 128 (1/2) | 4 |
| | | 64 (1/4) | 4 |
| | | 32 (1/8) | 8 |

TABLE 34-continued

| | | Peptide MIC (µg/ml) | |
|---|---|---|---|
| Bacteria | Antibiotic single treatment concentration | | Papiliocin 8 |
| A. baumannii | Erythromycin concentration (Conc./MIC) | 32 (1) | 0 |
| | | 16 (1/2) | 4 |
| | | 8 (1/4) | 4 |
| | | 4 (1/8) | 8 |
| | Vancomycin concentration (Conc./MIC) | 1024 (1) | 0 |
| | | 512 (1/2) | 2 |
| | | 256 (1/4) | 2 |
| | | 128 (1/8) | 4 |
| | Linezolid concentration (Conc./MIC) | 256 (1) | 0 |
| | | 128 (1/2) | 4 |
| | | 64 (1/4) | 4 |
| | | 32 (1/8) | 8 |

Antibacterial activity of papiliocin as a comparative control against E. coli and A. baumannii during treatment with antibiotic <3-3> Identification of Synergistic Effect of Antibacterial Activity Using MIC Value During Combined Treatment of Antimicrobial Peptide and Antibiotic A synergistic effect of a peptide and antibiotics was evaluated at antibacterial activity against a strain by using an MIC value determined for each mixed solution. For the evaluation, a fractional inhibitory concentration (FIC) value was used (Elion, Gertrude B., Samuel Singer, and George H. Hitchings. *Journal of Biological Chemistry* 208.2 (1954): 477-488.).

Specifically, an FIC value was calculated by the following [Equation 1] using the MIC values calculated in Examples <3-1> and <3-2>, and according to the calculated FIC values, the synergistic effect was evaluated as follows: <0.5, Synergy effect; 0.5 to 1, Partial synergy effect; 1.0, Additive effect; 2.0 to 4.0, Indifference; >4.0, Antagonism.

$$FIC\ index = \frac{MIC_A\ comb}{MIC_A\ alone} + \frac{MIC_B\ comb}{MIC_B\ alone} \quad [\text{Equation 1}]$$

A method generally used to decide the synergistic effect by using the FIC values is a checkerboard assay, and is a method that selects the lowest FIC index value in a well in which the growth of bacteria is suppressed. However, the selection of one FIC index in the method has a problem in that when the antibacterial activity of the antibiotics is lower, the FIC index is calculated so as to have a big synergistic effect, and is not accurate and has many experimental errors. Thus, with respect to the FIC index calculated by [Equation 1], an average FIC index was again calculated by using the following [Equation 2] (He, Jing, Charles G. Starr, and William C. Wimley. Biochimica et Biophysica Acta (BBA)-Biomembranes 1848.1 (2015): 8-15.).

$$Average\ FIC\ index = \frac{Total\ sum\ of\ FIC\ index}{Number\ sum\ of\ FIC\ index} \quad [\text{Equation 2}]$$

As a result of identifying a synergistic effect of the antibacterial activity in which erythromycin, vancomycin or linezolid which are existing antibiotics was administered in combination with PapMA-1 to PapMA-24 which are antimicrobial peptides of the present invention as shown in the following [Table 35] to [Table 38], it was confirmed that when the antimicrobial peptide of the present invention was administered in combination with antibiotics which have high antibacterial activity against gram-positive bacteria only and have no activity against gram-negative bacteria, the synergistic effect was excellent because all the antibiotics had an FIC index of less than 0.5 or a similar level 0.09 to 0.51 against *E. coli* which is a gram-negative bacterium. Further, it was confirmed that the synergistic effect was very excellent because all the antibiotics had an FIC index within a range of 0.06 to 0.31 which is much lower than 0.5 against a multi-drug resistant *E. coli* (MDREC 1229).

It was confirmed that the synergistic effect was very excellent because all the antibiotics had an FIC index of 0.05 to 0.54 which is much lower than 0.5 against *A. baumannii*, and it was confirmed that the synergistic effect was very excellent because all the antibiotics had an FIC index of 0.04 to 0.61 which is much lower than 0.5 against a resistant strain thereof (MDRAB 12035).

Accordingly, it was confirmed that when the antimicrobial peptide of the present invention was used as a complex with existing antibiotics against gram-negative bacteria which have been a social issue due to the recent severe resistance problem, a high synergistic effect could be obtained (Tables 35 to 38, and FIGS. 1 to 4).

TABLE 35

*E. coli*

| Name of peptide | Average FIC index | | |
|---|---|---|---|
| | Erythromycin | Vancomycin | Linezolid |
| PapMA-1 | 0.14 | 0.16 | 0.22 |
| PapMA-2 | 0.14 | 0.16 | 0.14 |
| PapMA-3 | 0.15 | 0.22 | 0.20 |
| PapMA-4 | 0.23 | 0.33 | 0.24 |
| PapMA-5 | 0.28 | 0.13 | 0.30 |
| PapMA-6 | 0.16 | 0.09 | 0.32 |
| PapMA-7 | 0.16 | 0.09 | 0.27 |
| PapMA-8 | 0.28 | 0.14 | 0.43 |
| PapMA-9 | 0.28 | 0.15 | 0.34 |
| PapMA-10 | 0.34 | 0.15 | 0.47 |
| PapMA-11 | 0.18 | 0.15 | 0.36 |
| PapMA-12 | 0.32 | 0.21 | 0.51 |
| PapMA-13 | 0.16 | 0.12 | 0.30 |
| PapMA-14 | 0.38 | 0.21 | 0.51 |
| PapMA-15 | 0.17 | 0.22 | 0.30 |
| PapMA-16 | 0.21 | 0.22 | 0.33 |
| PapMA-17 | 0.28 | 0.23 | 0.46 |
| PapMA-18 | 0.19 | 0.20 | 0.36 |
| PapMA-19 | 0.16 | 0.10 | 0.23 |
| PapMA-20 | 0.21 | 0.20 | 0.29 |
| PapMA-21 | 0.15 | 0.21 | 0.35 |
| PapMA-22 | 0.24 | 0.17 | 0.36 |
| PapMA-23 | 0.28 | 0.21 | 0.35 |
| PapMA-24 | 0.23 | 0.16 | 0.36 |

Comparison of FIC indices exhibiting synergistic effect of antibacterial activity against *E. coli* during combined treatment of antimicrobial peptide and antibiotic

TABLE 36

MDREC 1229

| Name of peptide | Average FIC index | | |
|---|---|---|---|
| | Erythromycin | Vancomycin | Linezolid |
| PapMA-1 | 0.11 | 0.20 | 0.16 |
| PapMA-2 | 0.08 | 0.16 | 0.12 |
| PapMA-3 | 0.13 | 0.26 | 0.14 |
| PapMA-4 | 0.09 | 0.26 | 0.15 |
| PapMA-5 | 0.14 | 0.20 | 0.12 |
| PapMA-6 | 0.07 | 0.16 | 0.07 |
| PapMA-7 | 0.06 | 0.12 | 0.06 |
| PapMA-8 | 0.19 | 0.21 | 0.23 |
| PapMA-9 | 0.08 | 0.14 | 0.08 |
| PapMA-10 | 0.20 | 0.22 | 0.25 |
| PapMA-11 | 0.14 | 0.22 | 0.30 |
| PapMA-12 | 0.16 | 0.24 | 0.22 |
| PapMA-13 | 0.24 | 0.29 | 0.24 |
| PapMA-14 | 0.16 | 0.24 | 0.22 |
| PapMA-15 | 0.20 | 0.22 | 0.19 |
| PapMA-16 | 0.21 | 0.14 | 0.18 |
| PapMA-17 | 0.25 | 0.31 | 0.28 |
| PapMA-18 | 0.17 | 0.16 | 0.19 |
| PapMA-19 | 0.12 | 0.14 | 0.16 |
| PapMA-20 | 0.16 | 0.24 | 0.17 |
| PapMA-21 | 0.15 | 0.26 | 0.28 |
| PapMA-22 | 0.14 | 0.26 | 0.28 |
| PapMA-23 | 0.17 | 0.23 | 0.18 |
| PapMA-24 | 0.16 | 0.22 | 0.18 |

Comparison of FIC indices exhibiting synergistic effect of antibacterial activity against MDREC 1229 as multi-drug resistant strain during combined treatment of antimicrobial peptide and antibiotic

TABLE 37

A. baumannii

| Name of peptide | Average FIC index | | |
|---|---|---|---|
| | Erythromycin | Vancomycin | Linezolid |
| PapMA-1 | 0.27 | 0.07 | 0.26 |
| PapMA-2 | 0.30 | 0.10 | 0.32 |
| PapMA-3 | 0.38 | 0.10 | 0.29 |
| PapMA-4 | 0.47 | 0.11 | 0.35 |
| PapMA-5 | 0.19 | 0.09 | 0.14 |
| PapMA-6 | 0.17 | 0.07 | 0.16 |
| PapMA-7 | 0.18 | 0.07 | 0.16 |
| PapMA-8 | 0.27 | 0.12 | 0.24 |
| PapMA-9 | 0.24 | 0.08 | 0.27 |
| PapMA-10 | 0.45 | 0.14 | 0.49 |
| PapMA-11 | 0.25 | 0.07 | 0.25 |
| PapMA-12 | 0.32 | 0.12 | 0.24 |
| PapMA-13 | 0.21 | 0.05 | 0.13 |
| PapMA-14 | 0.21 | 0.08 | 0.156 |
| PapMA-15 | 0.42 | 0.08 | 0.35 |
| PapMA-16 | 0.30 | 0.08 | 0.39 |
| PapMA-17 | 0.31 | 0.11 | 0.25 |
| PapMA-18 | 0.42 | 0.12 | 0.35 |
| PapMA-19 | 0.39 | 0.09 | 0.27 |
| PapMA-20 | 0.35 | 0.14 | 0.27 |
| PapMA-21 | 0.40 | 0.11 | 0.35 |
| PapMA-22 | 0.54 | 0.10 | 0.41 |
| PapMA-23 | 0.42 | 0.11 | 0.39 |
| PapMA-24 | 0.54 | 0.10 | 0.49 |

Comparison of FIC indices exhibiting synergistic effect of antibacterial activity against *A. baumannii* during combined treatment of antimicrobial peptide and antibiotic

TABLE 38

MDRAB 12035

| Name of peptide | Average FIC index | | |
|---|---|---|---|
| | Erythromycin | Vancomycin | Linezolid |
| PapMA-1 | 0.38 | 0.13 | 0.16 |
| PapMA-2 | 0.37 | 0.20 | 0.21 |
| PapMA-3 | 0.39 | 0.21 | 0.22 |
| PapMA-4 | 0.40 | 0.22 | 0.24 |
| PapMA-5 | 0.37 | 0.13 | 0.15 |
| PapMA-6 | 0.14 | 0.08 | 0.06 |
| PapMA-7 | 0.09 | 0.04 | 0.05 |
| PapMA-8 | 0.45 | 0.11 | 0.18 |
| PapMA-9 | 0.18 | 0.08 | 0.11 |
| PapMA-10 | 0.61 | 0.16 | 0.22 |
| PapMA-11 | 0.28 | 0.09 | 0.16 |
| PapMA-12 | 0.33 | 0.16 | 0.18 |
| PapMA-13 | 0.23 | 0.10 | 0.11 |
| PapMA-14 | 0.23 | 0.14 | 0.12 |
| PapMA-15 | 0.42 | 0.15 | 0.23 |
| PapMA-16 | 0.43 | 0.19 | 0.24 |
| PapMA-17 | 0.32 | 0.17 | 0.17 |
| PapMA-18 | 0.43 | 0.17 | 0.22 |
| PapMA-19 | 0.31 | 0.12 | 0.17 |
| PapMA-20 | 0.39 | 0.21 | 0.21 |
| PapMA-21 | 0.49 | 0.17 | 0.22 |
| PapMA-22 | 0.48 | 0.18 | 0.22 |
| PapMA-23 | 0.48 | 0.17 | 0.22 |
| PapMA-24 | 0.48 | 0.16 | 0.21 |

Comparison of FIC indices exhibiting synergistic effect of antibacterial activity against MDREC 1229 as multi-drug resistant strain during combined treatment of antimicrobial peptide and antibiotic Hereinafter, Preparation Examples of a medicine containing the antimicrobial peptide according to the present invention as an active ingredient will be described, but the present invention intends not to limit the same, but to only specifically describe the same. A medicine in Preparation Example 1 was prepared by a typical method according to the composition ingredient and composition ratio as follows using the antimicrobial peptide exhibiting antibacterial activity against gram-negative bacteria and gram-positive bacteria according to the present invention.

<Preparation Example 1> Preparation of Pharmaceutical Preparation

<1-1> Preparation of Powder

| | |
|---|---|
| A complex of the peptide of the present invention and an antibiotic | 2 g |
| Lactose | 1 g |

A powder was prepared by mixing the ingredients and filling an airtight pack with the ingredients.

<1-2> Preparation of Tablets

| | |
|---|---|
| A complex of the peptide of the present invention and an antibiotic | 100 mg |
| Corn starch | 100 mg |
| Lactose | 100 mg |
| Magnesium stearate | 2 mg |

After the ingredients were mixed, tablets were prepared by tableting the mixture according to a typical tablet preparation method.

<1-3> Preparation of Capsules

| | |
|---|---|
| A complex of the peptide of the present invention and an antibiotic | 100 mg |
| Corn starch | 100 mg |
| Lactose | 100 mg |
| Magnesium stearate | 2 mg |

After the aforementioned ingredients were mixed, capsules were prepared by filling gelatin capsules with the ingredients according to a typical capsule preparation method.

<1-4> Preparation of Pills

| | |
|---|---|
| A complex of the peptide of the present invention and an antibiotic | 1 g |
| Lactose | 1.5 g |
| Glycerin | 1 g |
| Xylitol | 0.5 g |

After the ingredients were mixed, pills were prepared so as to be 4 g per pill according to a typical method.

<1-5> Preparation of Granules

| | |
|---|---|
| A complex of the peptide of the present invention and an antibiotic | 150 mg |
| Soybean extract | 50 mg |
| Glucose | 200 mg |
| Starch | 600 mg |

After the ingredients were mixed, granules were formed by adding 100 mg of 30% ethanol to the mixture and drying the resulting product at 60° C., and cloth was then filled with the granules.

<1-6> Preparation of Injection

| A complex of the peptide of the present invention and an antibiotic | 500 ng |
| Mannitol | 180 mg |
| Na2HPO4H2O | 26 mg |
| Distilled water | 2974 mg |

According to a typical injection preparation method, an injection was prepared by containing the ingredients in a proposed content.

The invention claimed is:

1. An antimicrobial peptide consisting of the amino acid sequence obtained by modifying the amino acid sequence of SEQ ID No. 1, wherein the amino acid sequence of SEQ ID No. 1 is modified with one or more substitutions selected from the group consisting of the following (i) to (v):
   (i) substitution of proline (P) which is the 9th amino acid with D-lysine (k) or D-leucine (l), and substitution of phenylalanine (F) which is the 11th amino acid with leucine (L);
   (ii) substitution of phenylalanine (F) which is the 11th amino acid with leucine (L);
   (iii) substitution of serine (S) which is the 14th amino acid with glutamic acid (E) or L-lysine (K);
   (iv) substitution of alanine (A) which is the 15th amino acid with tryptophan (W), phenylalanine (F), or leucine (L); and
   (v) substitution of phenylalanine (F) which is the 18th amino acid with tryptophan (W).

2. The antimicrobial peptide of claim 1, wherein the antimicrobial peptide consists of any one amino acid sequence selected from the group consisting of SEQ ID Nos. 2 to 24.

3. An antimicrobial composition comprising the antimicrobial peptide of claim 1 as an active ingredient.

4. The antimicrobial composition of claim 3 further comprising antibiotics as active ingredients.

5. The antimicrobial composition of claim 3, wherein the antimicrobial peptide consists of any one amino acid sequence selected from the group consisting of SEQ ID Nos. 2 to 24.

6. The antimicrobial composition of claim 3, wherein the antimicrobial composition has antibacterial activity against gram-positive bacteria, gram-negative bacteria, and antibiotic-resistant strains thereof.

7. The antimicrobial composition of claim 6, wherein the gram-positive bacteria are one or more selected from the group consisting of Bacillus subtilis, Staphylococcus aureus and Staphylococcus epidermis, and wherein the gram-negative bacteria are one or more selected from the group consisting of Escherichia coli, Pseudomonas aeruginosa, Acinetobacter baumannii and Salmonella typhimurium.

8. The antimicrobial composition of claim 4, wherein the antibiotics are one or more selected from the group consisting of erythromycin, ampicillin, vancomycin, linezolid, methicillin, oxacillin, cefotaxime, rifampicin, amikacin, gentamicin, amikacin, kanamycin, tobramycin, neomycin, ertapenem, doripenem, imipenem/cilastatin, meropenem, ceftazidime, cefepime, ceftaroline, ceftobiprole, aztreonam, piperacillin, polymyxin b, colistin, ciprofloxacin, levofloxacin, moxifloxacin, gatifloxacin, tigecycline, a conjugate thereof, and derivatives thereof.

9. The antimicrobial composition of claim 3, wherein the antimicrobial composition is any one selected from the group consisting of a pharmaceutical composition, a food additive, a feed additive, an antiseptic composition, and a quasi-drug composition.

10. The antimicrobial peptide of claim 1, wherein the antimicrobial peptide is administered in combination with an antibiotic.

11. The antimicrobial peptide of claim 10, wherein the antibiotic is at least one or more of erythromycin, ampicillin, vancomycin, linezolid, methicillin, oxacillin, cefotaxime, rifampicin, amikacin, gentamicin, amikacin, kanamycin, tobramycin, neomycin, ertapenem, doripenem, imipenem/cilastatin, meropenem, ceftazidime, cefepime, ceftaroline, ceftobiprole, aztreonam, piperacillin, polymyxin b, colistin, ciprofloxacin, levofloxacin, moxifloxacin, gatifloxacin, tigecycline, or a conjugate thereof, or a derivative thereof.

12. The antimicrobial peptide of claim 10, wherein the antimicrobial peptide in combination with the antibiotic has antibacterial activity against gram-positive bacteria, gram-negative bacteria, and antibiotic-resistant strains thereof.

13. The antimicrobial peptide of claim 12, wherein the gram-positive bacteria is at least one or more of Bacillus subtilis, Staphylococcus aureus, or Staphylococcus epidermidis, and wherein the gram-negative bacteria is at least one or more of Escherichia coli, Pseudomonas aeruginosa, Acinetobacter baumannii, or Salmonella typhimurium.

* * * * *

SEQUENCE LISTING

```
<160> NUMBER OF SEQ ID NOS: 27

<210> SEQ ID NO 1
<211> LENGTH: 18
<212> TYPE: PRT
<213> ORGANISM: Artificial Sequence
<220> FEATURE:
<223> OTHER INFORMATION: PapMA-1

<400> SEQUENCE: 1

Arg Trp Lys Ile Phe Lys Lys Ile Pro Lys Phe Leu His Ser Ala Lys
1               5                   10                  15

Lys Phe

<210> SEQ ID NO 2
<211> LENGTH: 18
<212> TYPE: PRT
<213> ORGANISM: Artificial Sequence
<220> FEATURE:
<223> OTHER INFORMATION: PapMA-2

<400> SEQUENCE: 2

Arg Trp Lys Ile Phe Lys Lys Ile Pro Lys Phe Leu His Ser Ala Lys
1               5                   10                  15

Lys Trp

<210> SEQ ID NO 3
<211> LENGTH: 18
<212> TYPE: PRT
<213> ORGANISM: Artificial Sequence
<220> FEATURE:
<223> OTHER INFORMATION: PapMA-3

<400> SEQUENCE: 3

Arg Trp Lys Ile Phe Lys Lys Ile Pro Lys Phe Leu His Ser Trp Lys
1               5                   10                  15

Lys Phe

<210> SEQ ID NO 4
<211> LENGTH: 18
<212> TYPE: PRT
<213> ORGANISM: Artificial Sequence
<220> FEATURE:
<223> OTHER INFORMATION: PapMA-4

<400> SEQUENCE: 4

Arg Trp Lys Ile Phe Lys Lys Ile Pro Lys Phe Leu His Ser Trp Lys
1               5                   10                  15

Lys Trp

<210> SEQ ID NO 5
<211> LENGTH: 18
<212> TYPE: PRT
<213> ORGANISM: Artificial Sequence
<220> FEATURE:
```

<223> OTHER INFORMATION: PapMA-5

<400> SEQUENCE: 5

Arg Trp Lys Ile Phe Lys Lys Ile Pro Lys Phe Leu His Ser Phe Lys
1               5                   10                  15

Lys Phe

<210> SEQ ID NO 6
<211> LENGTH: 18
<212> TYPE: PRT
<213> ORGANISM: Artificial Sequence
<220> FEATURE:
<223> OTHER INFORMATION: PapMA-6

<400> SEQUENCE: 6

Arg Trp Lys Ile Phe Lys Lys Ile Pro Lys Phe Leu His Ser Leu Lys
1               5                   10                  15

Lys Phe

<210> SEQ ID NO 7
<211> LENGTH: 18
<212> TYPE: PRT
<213> ORGANISM: Artificial Sequence
<220> FEATURE:
<223> OTHER INFORMATION: PapMA-7

<400> SEQUENCE: 7

Arg Trp Lys Ile Phe Lys Lys Ile Pro Lys Leu Leu His Ser Phe Lys
1               5                   10                  15

Lys Phe

<210> SEQ ID NO 8
<211> LENGTH: 18
<212> TYPE: PRT
<213> ORGANISM: Artificial Sequence
<220> FEATURE:
<223> OTHER INFORMATION: PapMA-8

<400> SEQUENCE: 8

Arg Trp Lys Ile Phe Lys Lys Ile Pro Lys Leu Leu His Ser Leu Lys
1               5                   10                  15

Lys Phe

<210> SEQ ID NO 9
<211> LENGTH: 18
<212> TYPE: PRT
<213> ORGANISM: Artificial Sequence
<220> FEATURE:
<223> OTHER INFORMATION: PapMA-9

<400> SEQUENCE: 9

Arg Trp Lys Ile Phe Lys Lys Ile Pro Lys Leu Leu His Ser Ala Lys
1               5                   10                  15

Lys Trp

<210> SEQ ID NO 10
<211> LENGTH: 18
<212> TYPE: PRT
<213> ORGANISM: Artificial Sequence
<220> FEATURE:
<223> OTHER INFORMATION: PapMA-10

<400> SEQUENCE: 10

```
Arg Trp Lys Ile Phe Lys Lys Ile Pro Lys Leu Leu His Ser Leu Lys
1               5                   10                  15

Lys Trp

<210> SEQ ID NO 11
<211> LENGTH: 18
<212> TYPE: PRT
<213> ORGANISM: Artificial Sequence
<220> FEATURE:
<223> OTHER INFORMATION: PapMA-11

<400> SEQUENCE: 11

Arg Trp Lys Ile Phe Lys Lys Ile Pro Lys Phe Leu His Glu Ala Lys
1               5                   10                  15

Lys Phe

<210> SEQ ID NO 12
<211> LENGTH: 18
<212> TYPE: PRT
<213> ORGANISM: Artificial Sequence
<220> FEATURE:
<223> OTHER INFORMATION: PapMA-12

<400> SEQUENCE: 12

Arg Trp Lys Ile Phe Lys Lys Ile Pro Lys Leu Leu His Glu Phe Lys
1               5                   10                  15

Lys Phe

<210> SEQ ID NO 13
<211> LENGTH: 18
<212> TYPE: PRT
<213> ORGANISM: Artificial Sequence
<220> FEATURE:
<223> OTHER INFORMATION: PapMA-13

<400> SEQUENCE: 13

Arg Trp Lys Ile Phe Lys Lys Ile Pro Lys Leu Leu His Glu Ala Lys
1               5                   10                  15

Lys Trp

<210> SEQ ID NO 14
<211> LENGTH: 18
<212> TYPE: PRT
<213> ORGANISM: Artificial Sequence
<220> FEATURE:
<223> OTHER INFORMATION: PapMA-14

<400> SEQUENCE: 14

Arg Trp Lys Ile Phe Lys Lys Ile Pro Lys Phe Leu His Glu Ala Lys
1               5                   10                  15

Lys Trp

<210> SEQ ID NO 15
<211> LENGTH: 18
<212> TYPE: PRT
<213> ORGANISM: Artificial Sequence
<220> FEATURE:
<223> OTHER INFORMATION: PapMA-15

<400> SEQUENCE: 15

Arg Trp Lys Ile Phe Lys Lys Ile Lys Lys Leu Leu His Ser Phe Lys
1               5                   10                  15

Lys Phe
```

<210> SEQ ID NO 16
<211> LENGTH: 18
<212> TYPE: PRT
<213> ORGANISM: Artificial Sequence
<220> FEATURE:
<223> OTHER INFORMATION: PapMA-16

<400> SEQUENCE: 16

Arg Trp Lys Ile Phe Lys Lys Ile Lys Lys Leu Leu His Ser Ala Lys
1               5                   10                  15

Lys Trp

<210> SEQ ID NO 17
<211> LENGTH: 18
<212> TYPE: PRT
<213> ORGANISM: Artificial Sequence
<220> FEATURE:
<223> OTHER INFORMATION: PapMA-17

<400> SEQUENCE: 17

Arg Trp Lys Ile Phe Lys Lys Ile Lys Lys Leu Leu His Lys Phe Lys
1               5                   10                  15

Lys Phe

<210> SEQ ID NO 18
<211> LENGTH: 18
<212> TYPE: PRT
<213> ORGANISM: Artificial Sequence
<220> FEATURE:
<223> OTHER INFORMATION: PapMA-18

<400> SEQUENCE: 18

Arg Trp Lys Ile Phe Lys Lys Ile Lys Lys Leu Leu His Lys Ala Lys
1               5                   10                  15

Lys Trp

<210> SEQ ID NO 19
<211> LENGTH: 18
<212> TYPE: PRT
<213> ORGANISM: Artificial Sequence
<220> FEATURE:
<223> OTHER INFORMATION: PapMA-19

<400> SEQUENCE: 19

Arg Trp Lys Ile Phe Lys Lys Ile Lys Lys Leu Leu His Glu Phe Lys
1               5                   10                  15

Lys Phe

<210> SEQ ID NO 20
<211> LENGTH: 18
<212> TYPE: PRT
<213> ORGANISM: Artificial Sequence
<220> FEATURE:
<223> OTHER INFORMATION: PapMA-20

<400> SEQUENCE: 20

Arg Trp Lys Ile Phe Lys Lys Ile Lys Lys Leu Leu His Glu Ala Lys
1               5                   10                  15

Lys Trp

<210> SEQ ID NO 21
<211> LENGTH: 18

```
<212> TYPE: PRT
<213> ORGANISM: Artificial Sequence
<220> FEATURE:
<223> OTHER INFORMATION: PapMA-21

<400> SEQUENCE: 21

Arg Trp Lys Ile Phe Lys Lys Ile Leu Lys Leu Leu His Lys Phe Lys
1               5                   10                  15

Lys Phe

<210> SEQ ID NO 22
<211> LENGTH: 18
<212> TYPE: PRT
<213> ORGANISM: Artificial Sequence
<220> FEATURE:
<223> OTHER INFORMATION: PapMA-22

<400> SEQUENCE: 22

Arg Trp Lys Ile Phe Lys Lys Ile Leu Lys Leu Leu His Lys Ala Lys
1               5                   10                  15

Lys Trp

<210> SEQ ID NO 23
<211> LENGTH: 18
<212> TYPE: PRT
<213> ORGANISM: Artificial Sequence
<220> FEATURE:
<223> OTHER INFORMATION: PapMA-23

<400> SEQUENCE: 23

Arg Trp Lys Ile Phe Lys Lys Ile Leu Lys Leu Leu His Glu Phe Lys
1               5                   10                  15

Lys Phe

<210> SEQ ID NO 24
<211> LENGTH: 18
<212> TYPE: PRT
<213> ORGANISM: Artificial Sequence
<220> FEATURE:
<223> OTHER INFORMATION: PapMA-24

<400> SEQUENCE: 24

Arg Trp Lys Ile Phe Lys Lys Ile Leu Lys Leu Leu His Glu Ala Lys
1               5                   10                  15

Lys Trp

<210> SEQ ID NO 25
<211> LENGTH: 37
<212> TYPE: PRT
<213> ORGANISM: Artificial Sequence
<220> FEATURE:
<223> OTHER INFORMATION: Papiliocin

<400> SEQUENCE: 25

Arg Trp Lys Ile Phe Lys Lys Ile Glu Lys Val Gly Arg Asn Val Arg
1               5                   10                  15

Asp Gly Ile Ile Lys Ala Gly Pro Ala Val Ala Val Val Gly Gln Ala
            20                  25                  30

Ala Thr Val Val Lys
        35

<210> SEQ ID NO 26
<211> LENGTH: 23
```

```
<212> TYPE: PRT
<213> ORGANISM: Artificial Sequence
<220> FEATURE:
<223> OTHER INFORMATION: Magainin

<400> SEQUENCE: 26

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 27
<211> LENGTH: 26
<212> TYPE: PRT
<213> ORGANISM: Artificial Sequence
<220> FEATURE:
<223> OTHER INFORMATION: Melittin

<400> SEQUENCE: 27

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25
```